(12) United States Patent
Bolli et al.

(10) Patent No.: US 8,299,086 B2
(45) Date of Patent: Oct. 30, 2012

(54) PYRIMIDINE DERIVATIVES

(75) Inventors: Martin Bolli, Allschwil (CH); Cyrille Lescop, Kembs (FR); Boris Mathys, Pratteln (CH); Claus Mueller, Weil am Rhein (DE); Oliver Nayler, Arlesheim (CH); Beat Steiner, Dornach (CH)

(73) Assignee: Actelion Pharmaceuticals Ltd., Allschwill (CH)

( * ) Notice: Subject to any disclaimer, the term of this patent is extended or adjusted under 35 U.S.C. 154(b) by 256 days.

(21) Appl. No.: 12/738,110

(22) PCT Filed: Oct. 31, 2008

(86) PCT No.: PCT/IB2008/054543
§ 371 (c)(1),
(2), (4) Date: Apr. 15, 2010

(87) PCT Pub. No.: WO2009/057079
PCT Pub. Date: May 7, 2009

(65) Prior Publication Data
US 2010/0234346 A1    Sep. 16, 2010

(30) Foreign Application Priority Data

Nov. 1, 2007    (WO) .................. PCT/IB2007/054437

(51) Int. Cl.
*C07D 413/04*    (2006.01)
*A61K 31/506*    (2006.01)
(52) U.S. Cl. ........ 514/274; 514/275; 544/315; 544/316; 544/331
(58) Field of Classification Search .................. 544/315, 544/316, 331; 514/274, 275
See application file for complete search history.

(56) References Cited

U.S. PATENT DOCUMENTS

| | | |
|---|---|---|
| 2007/0043014 A1 | 2/2007 | Doherty et al. |
| 2010/0063108 A1 | 3/2010 | Bolli et al. |
| 2010/0087417 A1 | 4/2010 | Bolli et al. |
| 2010/0087495 A1 | 4/2010 | Bolli et al. |
| 2010/0168005 A1 | 7/2010 | Bolli et al. |
| 2010/0331372 A1 | 12/2010 | Bolli et al. |
| 2011/0028448 A1 | 2/2011 | Bolli et al. |
| 2011/0028449 A1 | 2/2011 | Bolli et al. |
| 2012/0108638 A1 | 5/2012 | Bolli et al. |

FOREIGN PATENT DOCUMENTS
WO    WO 91/15583    10/1991
(Continued)

OTHER PUBLICATIONS

Gura, Systems for identifying New Drugs Are Often Faulty, Cancer Models, Science, vol. 278, No. 5340, pp. 1041-1042, Nov. 1997.*

(Continued)

*Primary Examiner* — Deepak Rao

(74) *Attorney, Agent, or Firm* — Hoxie & Associates LLC

(57) ABSTRACT

The invention relates to novel pyrimidine derivatives, their preparation and their use as pharmaceutically active compounds. Said compounds particularly act as immunomodulating agents. Formula (I) wherein A represents Formula (II), Formula (III), Formula (IV), Formula (V), Formula (VI), Formula (VII), Formula (VIII) or Formula (IX)

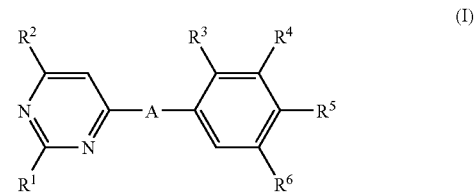

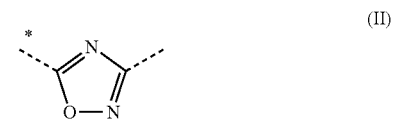

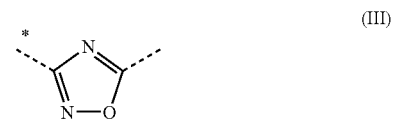

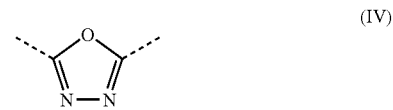

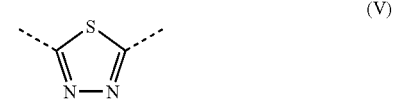

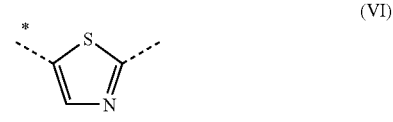

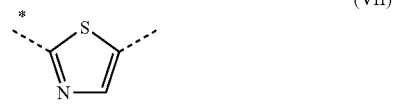

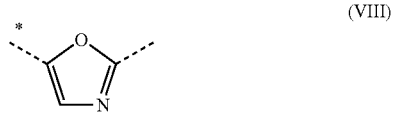

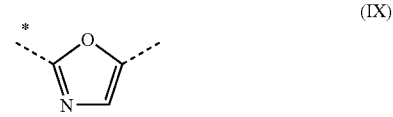

13 Claims, No Drawings

FOREIGN PATENT DOCUMENTS

| | | |
|---|---|---|
| WO | WO 99/46277 | 9/1999 |
| WO | WO 01/12627 | 2/2001 |
| WO | WO 03/062248 | 7/2003 |
| WO | WO 03/062252 | 7/2003 |
| WO | WO 2004/035538 | 4/2004 |
| WO | WO 2004/103279 | 12/2004 |
| WO | WO 2005/032465 | 4/2005 |
| WO | WO 2005/058848 | 6/2005 |
| WO | WO 2005/115382 | 12/2005 |
| WO | WO 2006/047195 | 5/2006 |
| WO | WO 2006/131336 | 12/2006 |
| WO | WO 2007/001973 | 1/2007 |
| WO | WO 2007/080542 | 7/2007 |
| WO | WO 2007/085451 | 8/2007 |
| WO | WO 2007/098474 | 8/2007 |
| WO | WO 2008/076356 | 6/2008 |
| WO | WO 2008/091967 | 7/2008 |
| WO | WO 2009/151529 | 12/2009 |

OTHER PUBLICATIONS

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20<sup>th</sup> Edition, vol. 1, pp. 1004-1010, 1996.*

Robinson, Medical Therapy of Inflammatory Bowel Disease for the 21st century, Eur. J. Surg. 164, Suppl. 582, pp. 90-98, (1998).*

Spiegel et al., Nature Reviews Immunology, vol. 11, No. 6, pp. 403-15, Jun. 2011.*

U.S. Appl. No. 12/673,918, Bolli, et al.

Battistuzzi, G., et al., "3-Arylpropanoate Esters through the Palladium-Catalyzed Reaction of Aryl Halides with Acrolein Diethyl Acetal", Synlett, vol. 8, pp. 1133-1136 (2003).

Benkeser, R.A., et al., "Additivity of Electrical Effects in Aromatic Electrophilic Substitutions as Determined by Desilylation Reactions", Am. Chem. Soc., vol. 80, pp. 5289-5293, (1958).

Brain, C.T., et al., "Novel procedure for the synthesis of 1,3,4-oxadiazoles from 1,2-diacylhydrazines using polymer-supported Burgess reagent under microwave conditions", Tetrahedron Lett., vol. 40, pp. 3275-3278, (1999).

Budensinsky, F., et al., "Reaktion Der Acylbrenztraubensaure-Methylester Mit Verbindungen Vom Harnstoff-Typus", Collection Czechoslov. Chem. Commun., vol. 26, pp. 2871-2885, (1961).

Chakraborti, G., et al., "One-Pot Synthesis of Nitriles from Aldehydes Under Microwave Irradiation: Influence of the Medium and Mode of Microwave Irradiation on Product Formation", Tetrahedron, vol. 55, pp. 13265-13268, (1999).

Cui, J., et al., "Design and Synthesis of Highly Constrained Factor Xa Inhibitors: Amidine-Substituted Bis(benzoyl)-[3]-diazepan-2-ones and Bis(benzylidene)-bis(gem-dimethyl)cycloketones", Biorg. Med. Chem., vol. 11, pp. 3379-3392 (2003).

Doyle, M.P., et al., "Alkyl Nitrite-Metal Halide Deamination Reactions. 2. Substitutive Deamination of Arylamines by Alkyl Nitrites and Copper(I1) Halides. A Direct and Remarkably Efficient Conversion of Arylamines to Aryl Halides", J. Org. Chem., vol. 42, pp. 2426-2429, (1977).

Gangloff, A.R., et al., "Synthesis of 3,5-disubstituted-1,2,4-oxadiazoles using tetrabutylammonium fluoride as a mild and efficient catalyst", Tetrahedron Lett., vol. 42, pp. 1441-1443, (2001).

Garcia, M.A., et al., "Synthesis, Biological Evaluation, and Three-Dimensional Quantitative Structure-Activity Relationship Study of Small-Molecule Positive Modulators of Adrenomedullin", J. Med. Chem., vol. 48, pp. 4068-4075, (2005).

Gould, P.L., "Salt Selection for Basic Drugs", International Journal of Pharmaceutics, vol. 33, pp. 201-217, (1986).

Greene, T.W., et al., Protective Groups in Organic Synthesis, 3<sup>rd</sup> Edition, Viley New York, (1999), J. Kocienski, Protecting Groups, Thieme Stuttgart, (1994).

Hamze, A., et al., "Synthesis of Various 3-Substituted 1,2,4-Oxadiazole-Containing Chiral â3- and r-Amino Acids from Fmoc-Protected Aspartic Acid", J. Org. Chem., vol. 68, pp. 7316-7321, (2003).

Hla, T., et al., "An Abundant Transcript Induced in Differentiating Human Endothelial Cells Encodes a Polypeptide with Structural Similarities to G-protein-coupled Receptors", Biol. Chem., vol. 265, pp. 9308-9313, (1990).

Holub, J.M., et al., "Lipid-Lowering Effects of Ethyl 2-Phenacyl-3-aryl-1H-pyrrole-4-carboxylates in Rodents", Molecules, vol. 9, pp. 135-157, (2004).

John, E.O., et al., "Reactions of (Difluoroamino)difluoroacetonitrile and (Difluoroamino) difluoroacetamidoxime", Inorganic Chemistry, vol. 27, pp. 3100-3104, (1988).

Kaboudin, B., et al., "One-Pot Synthesis of 1,2,4-Oxadiazoles Mediated by Microwave Irradiation Under Solvent-Free Condition", Heterocycles, vol. 60, No. 10, pp. 2287-2292, (2003).

Kerins, F., et al., "Generation of Substituted Styrenes via Suzuki Cross-Coupling of Aryl Halides with 2,4,6-Trivinylcyclotriboroxane", vol. 67, pp. 4968-4971, (2002).

Kiryanov, P., et al., "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis", J. Org. Chem. vol. 66, pp. 7925-7929, (2001).

Lamattina, J.L., "The Synthesis of 2-Amino-4-(4-Imidazolyl) pyridines", J. Heterocyclic Chem., vol. 20, pp. 533-538, (1983).

Loughlin, W.A., et al., "Investigations into the Parallel Synthesis of Novel Pyrrole-Oxazole Analogues of the Insecticide Pirate", Synthesis, pp. 1975-1980, (2006).

Meyer, E., et al., "Synthesis of New 1,2,4- and 1,3,4-Oxadiazole Derivatives", Synthesis, pp. 899-905, (2003).

Miltschitzky, S., et al., "Synthesis of Substituted Pyrimidine Hydrazine Acids (PHA) and their Use in Peptide Recognition", Heterocycles, vol. 67, pp. 135-160, (2006).

Palanki, M.S.S., et al., "Inhibitors of NF-KB and AP-1 Gene Expression: SAR Studies on the Pyrimidine Portion of 2-Chloro-4-trifluoromethylpyrimidine-54[N-(3',5'-bis(trifluoromethyl)-phenyl)carboxamide]", J. Med. Chem., vol. 43, pp. 3995-4004, (2000).

Pesson, M., et al., Antibacteriens de Synthese—Derives de l'acide pipemidique, Eur. J. Med. Chem., vol. 15, pp. 263-268, (1980).

Poulain, R.F., et al. "Parallel synthesis of 1,2,4-oxadiazoles from carboxylic acids using an improved, uronium-based, activation", Tetrahedron Lett., vol. 42, pp. 1495-1498, (2001).

Srivastava, R.M., et al., Synthesis of 3-Aryl-5-[Thien-3-YlMethyl]-1,2,4-Oxadiazoles, Synthetic Commun., vol. 29, pp. 1437-1450, (1999).

Suzuki, T., et al., "Synthesis of the Selective 5-Hydroxytryptamine4 (5-HT$_4$) Receptor Agonist (+)-(S)-2-Chloro-5-methoxy-4-[5-(2-piperidylmethyl)-1,2,4-oxadiazol-3-yl]aniline", Chem. Pharm. Bull., vol. 47, No. 1, pp. 120-122, (1999).

Trapani, G., et al., "Propofol Analogues. Synthesis, Relationships between Structure and Affinity at GABAA Receptor in Rat Brain, and Differential Electrophysiological Profile at Recombinant Human GABAA Receptors", J. Med. Chem., vol. 41, pp. 1846-1854, (1998).

Widler, L., et al., 7-Alkyl- and 7-Cycloalkyl-5-aryl-pyrrolo[2,3-d]pyrimidines—Potent Inhibitors of the Tyrosine Kinase c-Src, Bioorganic and Med. Chem. Lett., vol. 11, pp. 849-852, (2001).

Xu, B., et al., "Acyclic Analogues of Adenosine Bisphosphates as P2Y Receptor Antagonists: Phosphate Substitution Leads to Multiple Pathways of Inhibition of Platelet Aggregation", J. Med. Chem., vol. 45, pp. 5694-5709, (2002).

Yan, L., et al., "Discovery of 3-arylpropionic acids as potent agonists of sphingosine-1-phosphate receptor-1 (S1P1) with high selectivity against all other known S1P receptor subtypes", Bioorganic & Med. Chem. Lett., vol. 16, pp. 3679-3683, (2006).

Zanon, J., et al., "Copper-Catalyzed Domino Halide Exchange-Cyanation of Aryl Bromides", J. Am. Chem. Soc., vol. 125, pp. 2890-2891, (2003).

Sato, N. et al., "Synthesis and evaluation of substituted 4-alkoxy-2-aminopyridines as novel neuropeptide Y1 receptor antagonists", Bioorganic & Medicinal Chemistry Letters 14 (2004) 1761-1764.

Remington, The Science and Practice of Pharmacy, 21st Edition, 2005.

* cited by examiner

PYRIMIDINE DERIVATIVES

CROSS REFERENCE TO RELATED APPLICATIONS

This application is a United States Application under 35 U.S.C. 371 claiming benefit of PCT Application No. PCT/IB2008/054543, filed on Oct. 31, 2008, which claims the benefit of PCT Application No. PCT/IB2007/054437, filed on Nov. 1, 2007.

FIELD OF THE INVENTION

The present invention relates to S1P1/EDG1 receptor agonists of formula (I) and their use as active ingredients in the preparation of pharmaceutical compositions. The invention also concerns related aspects including processes for the preparation of the compounds, pharmaceutical compositions containing a compound of the formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of formula (I) are assessed using a GTPγS assay to determine $EC_{50}$ values and by measuring the circulating lymphocytes in the rat after oral administration, respectively (see in Examples).

i) The invention relates to novel pyrimidine compounds of the formula (I)

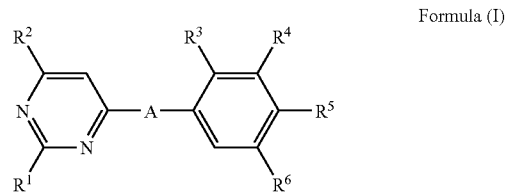

Formula (I)

wherein

A represents

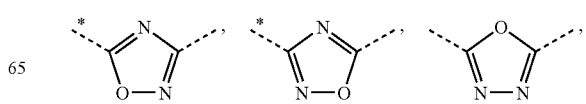

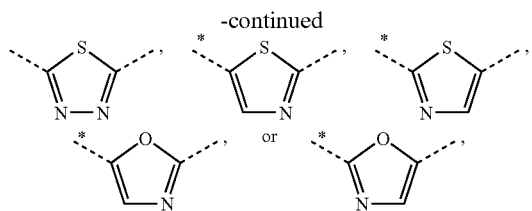

wherein the asterisks indicate the bond that is linked to the pyrimidine group of formula (I);

$R^1$ represents $C_{1-4}$-alkoxy, $C_{1-4}$-alkylamino, N—$C_{1-4}$-alkyl-N—$C_{1-3}$-alkylamino, $C_{3-5}$-cycloalkylamino, $C_{3-5}$-cycloalkylmethylamino, pyrrolidine (such as pyrrolidin-1-yl), or piperidine;

$R^2$ represents $C_{1-2}$-alkyl or $C_{3-4}$-alkyl;

$R^3$ represents hydrogen, $C_{1-4}$-alkyl, or $C_{1-3}$-alkoxy;

$R^4$ represents hydrogen, $C_{1-4}$-alkyl, or $C_{1-3}$-alkoxy;

$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy (such as preferably (S)-2,3-dihydroxy-propoxy), 2-hydroxy-3-methoxy-propoxy, —$OCH_2$—$(CH_2)_m$—$NR^{51}R^{52}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—$CH(OH)$—$CH_2$—$NR^{51}R^{52}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$ (wherein the carbon atom to which the hydroxy group is attached is preferably in the S-configuration);

$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, ($C_{1-5}$-alkylcarboxy)methyl, 2-carboxyethyl, 2-($C_{1-5}$-alkylcarboxy)ethyl, or 2-aminoethyl;

$R^{52}$ represents hydrogen, methyl, or ethyl;

$R^{53}$ represents $C_{1-3}$-alkyl, methylamino, ethylamino, or dimethylamino;

$R^{54}$ represents hydroxy-$C_{1-2}$-alkyl or $R^{55}R^{56}N$—$C_{1-2}$-alkyl;

$R^{55}$ and $R^{56}$ independently represent hydrogen or methyl;

k represents the integer 1, 2, or 3;

m represents the integer 1 or 2;

n represents 0, 1, or 2; and $R^6$ represents hydrogen, $C_{1-4}$-alkyl, or halogen.

The general terms used hereinbefore and hereinafter preferably have, within this disclosure, the following meanings, unless otherwise indicated:

The term $C_{x-y}$-alkyl, x and y being an integer, means saturated, branched or straight chain alkyl groups with x to y carbon atoms. Likewise, the term $C_{1-4}$-alkyl means saturated, branched or straight chain alkyl groups with one to four carbon atoms. Examples of $C_{1-4}$-alkyl groups are methyl, ethyl, n-propyl, iso-propyl, n-butyl, and iso-butyl (preferably methyl, ethyl, n-propyl, iso-propyl, or iso-butyl). Likewise, the term $C_{1-3}$-alkyl means saturated, branched or straight chain alkyl groups with one to three carbon atoms. Examples of $C_{1-3}$-alkyl groups are methyl, ethyl, n-propyl, and iso-propyl (preferably methyl, or ethyl).

The term $C_{x-y}$-alkoxy means a R—O group, wherein R is a $C_{x-y}$-alkyl. Examples of $C_{1-4}$-alkoxy groups are methoxy, ethoxy, n-propoxy, iso-propoxy, and iso-butoxy.

The term $C_{3-5}$-cycloalkyl refers to a saturated cyclic hydrocarbon ring system with 3 to 5 carbon atoms, i.e. cyclopropyl, cyclobutyl, or cyclopentyl.

The term halogen means fluoro, chloro, bromo or iodo (preferably fluoro or chloro; especially preferred chloro).

ii) A further embodiment of the invention relates to pyrimidine derivatives according to embodiment i), wherein A represents

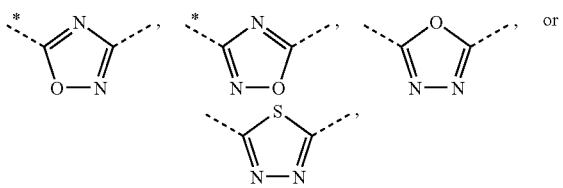

wherein the asterisks indicate the bond that is linked to the pyrimidine group of formula (I).

iii) Another embodiment of the invention relates to pyrimidine derivatives according to embodiment i), wherein A represents

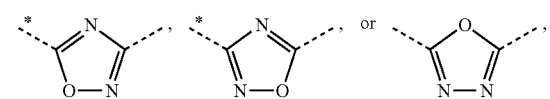

wherein the asterisks indicate the bond that is linked to the pyrimidine group of formula (I).

iv) Another embodiment of the invention relates to pyrimidine derivatives according to embodiment i), wherein A represents

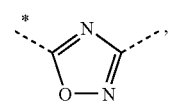

wherein the asterisk indicates the bond that is linked to the pyrimidine group of formula (I).

v) Another embodiment of the invention relates to pyrimidine derivatives according to embodiment i), wherein A represents

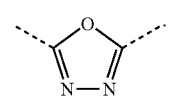

vi) Another embodiment of the invention relates to pyrimidine derivatives according to any one of the embodiments i) to v), wherein $R^1$ represents $C_{1-4}$-alkylamino or N—$C_{1-4}$-alkyl-N—$C_{1-3}$-alkylamino.

vii) Another embodiment of the invention relates to pyrimidine derivatives according to any one of the embodiments i) to v), wherein $R^1$ represents $C_{1-4}$-alkylamino.

viii) Another embodiment of the invention relates to pyrimidine derivatives according to any one of the embodiments i) to vii), wherein $R^2$ represents $C_{1-2}$-alkyl.

ix) Another embodiment of the invention relates to pyrimidine derivatives according to any one of the embodiments i) to vii), wherein $R^2$ represents methyl.

x) Another embodiment of the invention relates to pyrimidine derivatives according to any one of the embodiments i) to ix), wherein $R^3$ represents hydrogen.

xi) Another embodiment of the invention relates to pyrimidine derivatives according to any one of the embodiments i) to ix), wherein $R^3$ represents methoxy, and $R^4$ and $R^6$ represent hydrogen.

xii) Another embodiment of the invention relates to pyrimidine derivatives according to any one of the embodiments i) to ix), wherein $R^3$ represents hydrogen, $R^4$ represents $C_{1-3}$-alkyl or methoxy, and $R^6$ represents $C_{1-2}$-alkyl or chloro.

xiii) Another embodiment of the invention relates to pyrimidine derivatives according to any one of the embodiments i) to ix), wherein $R^3$ represents hydrogen, $R^4$ represents methyl or ethyl, and $R^6$ represents methyl.

xiv) Another embodiment of the invention relates to pyrimidine derivatives according to any one of the embodiments i) to ix), wherein $R^3$ represents hydrogen, $R^4$ represents methoxy or methyl, and $R^6$ represents chloro.

xv) Another embodiment of the invention relates to pyrimidine derivatives according to any one of the embodiments i) to xiv), wherein $R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$.

xvi) Another embodiment of the invention relates to pyrimidine derivatives according to any one of the embodiments i) to xiv), wherein $R^5$ represents 2,3-dihydroxypropyl, —$(CH_2)_n CH(OH)$—$CH_2$—$NHSO_2R^{53}$, —$CH_2$—$(CH_2)_k$—$NHCOR^{54}$, —$CH_2$—$(CH_2)_k$—$NHSO_2R^{53}$, —$(CH_2)_n CH(OH)$—$CH_2$—$NHCOR^{54}$, —$CH_2$—$(CH_2)_n$—$CONR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$.

xvii) Another embodiment of the invention relates to pyrimidine derivatives according to any one of the embodiments i) to xiv), wherein $R^5$ represents —$CH_2$—$(CH_2)_n$—$CONR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$.

xviii) Another embodiment of the invention relates to pyrimidine derivatives according to any one of the embodiments i) to xiv), wherein $R^5$ represents hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$.

xix) Another embodiment of the invention relates to pyrimidine derivatives according to any one of the embodiments i) to xiv), wherein $R^5$ represents 2,3-dihydroxy-propoxy or —$OCH_2$—$CH(OH)$—$CH_2$—$NHCOR^{54}$.

xx) Another embodiment of the invention relates to pyrimidine derivatives according to any one of the embodiments i) to xviii), wherein $R^{51}$ represents 2-hydroxyethyl or 2-carboxyethyl.

xxi) Another embodiment of the invention relates to pyrimidine derivatives according to any one of the embodiments i) to xviii), wherein $R^{52}$ represents hydrogen.

xxii) Another embodiment of the invention relates to pyrimidine derivatives according to any one of the embodiments i) to xviii), wherein $R^{53}$ represents methyl or methylamino.

xxiii) Another embodiment of the invention relates to pyrimidine derivatives according to any one of the embodiments i) to xix), wherein $R^{54}$ represents hydroxymethyl.

xxiv) Another embodiment of the invention relates to pyrimidine derivatives according to any one of the embodiments i) to xvii), wherein n represents the integer 1.

xxv) Another embodiment of the invention relates to pyrimidine derivatives according to any one of the embodiments i) to xvi), wherein k represents the integer 1 or 2.

xxvi) A further embodiment of the invention relates to pyrimidine derivatives according to embodiment i), wherein A represents

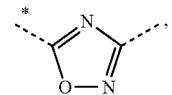

wherein the asterisk indicates the bond that is linked to the pyrimidine group of formula (I);
$R^1$ represents $C_{1-4}$-alkoxy, $C_{1-4}$-alkylamino, or N—$C_{1-4}$-alkyl-N—$C_{1-3}$-alkylamino;
$R^2$ represents $C_{1-2}$-alkyl;
$R^3$ represents hydrogen;
$R^4$ represents $C_{1-2}$-alkyl;
$R^5$ represents 2,3-dihydroxy-propoxy or —$OCH_2$—$CH(OH)$—$CH_2$—$NHCOR^{54}$;
$R^{54}$ represents hydroxy-$C_{1-2}$-alkyl; and
$R^6$ represents $C_{1-3}$-alkyl.

xxvii) A further embodiment of the invention relates to pyrimidine derivatives according to embodiment xxvi), wherein $R^1$ represents $C_{1-4}$-alkylamino or N—$C_{1-4}$-alkyl-N—$C_{1-3}$-alkylamino.

xxviii) A further embodiment of the invention relates to novel pyrimidine derivatives according to any one of embodiments i) to v) and viii) to xxvi), wherein $R^1$ represents $C_{1-4}$-alkoxy.

xxix) A further embodiment of the invention relates to novel pyrimidine derivatives according to embodiment i), wherein A represents

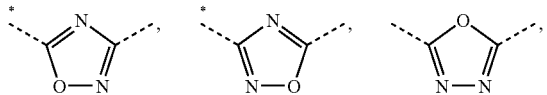

-continued

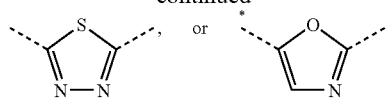

wherein the asterisks indicate the bond that is linked to the pyrimidine group of formula (I);
$R^1$ represents $C_{1-4}$-alkoxy, $C_{1-4}$-alkylamino, N—$C_{1-4}$-alkyl-N—$C_{1-3}$-alkylamino, $C_{3-5}$-cycloalkylamino, $C_{3-5}$-cycloalkylmethylamino, or pyrrolidine (such as pyrrolidin-1-yl);
$R^2$ represents $C_{1-2}$-alkyl or $C_{3-4}$-alkyl;
$R^3$ represents hydrogen, $C_{1-4}$-alkyl, or $C_{1-3}$-alkoxy;
$R^4$ represents hydrogen, $C_{1-4}$-alkyl, or $C_{1-3}$-alkoxy;
$R^5$ represents 2,3-dihydroxypropyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy (such as preferably (S)-2,3-dihydroxy-propoxy), 2-hydroxy-3-methoxy-propoxy, —$OCH_2$—$(CH_2)_m$—$NR^{51}R^{52}$, 2-[(azetidine-3-carboxylic acid)-1-yl]-ethoxy, 2-[(azetidine-3-carboxylic acid $C_{1-5}$-alkylester)-1-yl]ethoxy, 2-[(pyrrolidine-3-carboxylic acid)-1-yl]-ethoxy, 2-[(pyrrolidine-3-carboxylic acid $C_{1-5}$-alkylester)-1-yl]ethoxy, —$OCH_2$—$CH(OH)$—$CH_2$—$NR^{51}R^{52}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$ (wherein the carbon atom to which the hydroxy group is attached is preferably in the S-configuration);
$R^{51}$ represents hydrogen, $C_{1-3}$-alkyl, 2-hydroxyethyl, 2-hydroxy-1-hydroxymethyl-ethyl, 2,3-dihydroxypropyl, 2-carboxyethyl, 2-($C_{1-5}$-alkylcarboxy)ethyl, or 2-aminoethyl;
$R^{52}$ represents hydrogen;
$R^{53}$ represents $C_{1-3}$-alkyl or dimethylamino;
$R^{54}$ represents hydroxy-$C_{1-2}$-alkyl or $R^{55}R^{56}N$—$C_{1-2}$-alkyl;
$R^{55}$ and $R^{56}$ both represent hydrogen;
k and m represent the integer 1;
n represents 0 or 1; and
$R^6$ represents hydrogen, $C_{1-4}$-alkyl, or halogen.
xxx) A further embodiment of the invention relates to novel pyrimidine derivatives according to embodiment i), wherein A represents

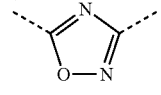

wherein the asterisk indicates the bond that is linked to the pyrimidine group of formula (I);
$R^1$ represents $C_{1-4}$-alkoxy;
$R^2$ represents $C_{1-2}$-alkyl or $C_{3-4}$-alkyl;

$R^3$ represents hydrogen;
$R^4$ represents $C_{1-4}$-alkyl, or $C_{1-3}$-alkoxy;
$R^5$ represents —$(CH_2)_n CH(OH)$—$CH_2$—$NHCOR^{54}$, —$CH_2$—$(CH_2)_n$—$CONR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$(CH_2)_m$—$NR^{51}R^{52}$, 2-[(azetidine-3-carboxylic acid)-1-yl]-ethoxy, 2-[(pyrrolidine-3-carboxylic acid)-1-yl]-ethoxy, —$OCH_2$—$CH(OH)$—$CH_2$—$NR^{51}R^{52}$, 3-[(azetidine-3-carboxylic acid)-1-yl]-2-hydroxypropoxy, 2-hydroxy-3-[(pyrrolidine-3-carboxylic acid)-1-yl]propoxy, 2-hydroxy-3-[(pyrrolidine-2-carboxylic acid)-1-yl]propoxy, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$;
$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, ($C_{1-5}$-alkylcarboxy)methyl, 2-carboxyethyl, 2-($C_{1-5}$-alkylcarboxy)ethyl, or 2-aminoethyl;
$R^{52}$ represents hydrogen, methyl, or ethyl;
$R^{53}$ represents $C_{1-3}$-alkyl, methylamino, ethylamino, or dimethylamino;
$R^{54}$ represents hydroxy-$C_{1-2}$-alkyl or $R^{55}R^{56}N$—$C_{1-2}$-alkyl;
$R^{55}$ and $R^{56}$ independently represent hydrogen or methyl;
m represents the integer 1 or 2;
n represents 0, 1, or 2; and
$R^6$ represents hydrogen, $C_{1-4}$-alkyl, or halogen.

The compounds of formula (I) may contain one or more stereogenic or asymmetric centers, such as one or more asymmetric carbon atoms. Substituents at a double bond may be present in the Z- or E-configuration unless indicated otherwise. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of formula (I) is to be understood as referring also to salts, especially pharmaceutically acceptable salts, of a compound of formula (I), as appropriate and expedient.

Salts are preferably the pharmaceutically acceptable salts of the compounds of formula (I).

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Examples of preferred compounds are selected from the group consisting of:
N-(3-{2,6-dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide;
N-(3-{4-[5-(2-ethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide;
N-(3-{2,6-dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide;
N-(3-{4-[5-(2-isopropylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{2-ethyl-4-[5-(2-isobutylamino-6-methyl-pyrimidin-4-yl)-[1,2,4]oxadiazol-3-yl]-6-methyl-phenoxy}-2-hydroxy-propyl)-2-hydroxy-acetamide;

N-(3-{4-[5-(2-isobutylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{4-[5-(2-diethylamino-6-methyl-pyrimidin-4-yl)-[1,2,4]oxadiazol-3-yl]-2-ethyl-6-methyl-phenoxy}-2-hydroxy-propyl)-2-hydroxy-acetamide;
N-(3-{4-[5-(2-diethylamino-6-methyl-pyrimidin-4-yl)-[1,2,4]oxadiazol-3-yl]-2,6-dimethyl-phenoxy}-2-hydroxy-propyl)-2-hydroxy-acetamide;
N-(3-{4-[5-(2-dimethylamino-6-methyl-pyrimidin-4-yl)-[1,2,4]oxadiazol-3-yl]-2,6-dimethyl-phenoxy}-2-hydroxy-propyl)-2-hydroxy-acetamide;
N-(3-{4-[5-(2-(ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide;
N-(3-{4-[5-(2-isopropoxy-6-methyl-pyrimidin-4-yl)-[1,2,4]oxadiazol-3-yl]-2,6-dimethyl-phenoxy}-2-hydroxy-propyl)-2-hydroxy-acetamide;
3-{4-[5-(2-ethylamino-6-methyl-pyrimidin-4-yl)-[1,2,4]oxadiazol-3-yl]-2,6-dimethyl-phenoxy}-propane-1,2-diol;
3-{2,6-dimethyl-4-[5-(6-methyl-2-propylamino-pyrimidin-4-yl)-[1,2,4]oxadiazol-3-yl]-phenoxy}-propane-1,2-diol;
3-{4-[5-(2-isopropylamino-6-methyl-pyrimidin-4-yl)-[1,2,4]oxadiazol-3-yl]-2,6-dimethyl-phenoxy}-propane-1,2-diol;
3-{4-[5-(2-isobutylamino-6-methyl-pyrimidin-4-yl)-[1,2,4]oxadiazol-3-yl]-2,6-dimethyl-phenoxy}-propane-1,2-diol;
3-{4-[5-(2-diethylamino-6-methyl-pyrimidin-4-yl)-[1,2,4]oxadiazol-3-yl]-2,6-dimethyl-phenoxy}-propane-1,2-diol; and
3-{4-[5-(2-(ethyl-methylamino)-6-methyl-pyrimidin-4-yl)-[1,2,4]oxadiazol-3-yl]-2,6-dimethyl-phenoxy}-propane-1,2-diol.

Examples of preferred compounds are further selected from the group consisting of:
N—((S)-3-{2,6-dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide;
N—((R)-3-{2,6-dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide;
N—((S)-3-{4-[5-(2-ethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-ethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide;
N—((S)-3-{2,6-dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide;
N—((R)-3-{2,6-dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide;
N—((S)-3-{4-[5-(2-isopropylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-isopropylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{2-ethyl-4-[5-(2-isobutylamino-6-methyl-pyrimidin-4-yl)-[1,2,4]oxadiazol-3-yl]-6-methyl-phenoxy}-2-hydroxy-propyl)-2-hydroxy-acetamide;
N—((S)-3-{4-[5-(2-isobutylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-isobutylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{4-[5-(2-diethylamino-6-methyl-pyrimidin-4-yl)-[1,2,4]oxadiazol-3-yl]-2-ethyl-6-methyl-phenoxy}-2-hydroxy-propyl)-2-hydroxy-acetamide;
N—((S)-3-{4-[5-(2-diethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-diethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{4-[5-(2-dimethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-dimethylamino-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{4-[5-(2-(ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-(ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide;
N—((S)-3-{4-[5-(2-isopropoxy-6-methyl-pyrimidin-4-yl)-[1,2,4]oxadiazol-3-yl]-2,6-dimethyl-phenoxy}-2-hydroxy-propyl)-2-hydroxy-acetamide;
N—((R)-3-{4-[5-(2-isopropoxy-6-methyl-pyrimidin-4-yl)-[1,2,4]oxadiazol-3-yl]-2,6-dimethyl-phenoxy}-2-hydroxy-propyl)-2-hydroxy-acetamide;
(S)-3-{4-[5-(2-ethylamino-6-methyl-pyrimidin-4-yl)-[1,2,4]oxadiazol-3-yl]-2,6-dimethyl-phenoxy}-propane-1,2-diol;
(R)-3-{4-[5-(2-ethylamino-6-methyl-pyrimidin-4-yl)-[1,2,4]oxadiazol-3-yl]-2,6-dimethyl-phenoxy}-propane-1,2-diol;
(S)-3-{2,6-dimethyl-4-[5-(6-methyl-2-propylamino-pyrimidin-4-yl)-[1,2,4]oxadiazol-3-yl]-phenoxy}-propane-1,2-diol;
(R)-3-{2,6-dimethyl-4-[5-(6-methyl-2-propylamino-pyrimidin-4-yl)-[1,2,4]oxadiazol-3-yl]-phenoxy}-propane-1,2-diol;
(S)-3-{4-[5-(2-isopropylamino-6-methyl-pyrimidin-4-yl)-[1,2,4]oxadiazol-3-yl]-2,6-dimethyl-phenoxy}-propane-1,2-diol;
(R)-3-{4-[5-(2-isopropylamino-6-methyl-pyrimidin-4-yl)-[1,2,4]oxadiazol-3-yl]-2,6-dimethyl-phenoxy}-propane-1,2-diol;
(S)-3-{4-[5-(2-isobutylamino-6-methyl-pyrimidin-4-yl)-[1,2,4]oxadiazol-3-yl]-2,6-dimethyl-phenoxy}-propane-1,2-diol;
(R)-3-{4-[5-(2-isobutylamino-6-methyl-pyrimidin-4-yl)-[1,2,4]oxadiazol-3-yl]-2,6-dimethyl-phenoxy}-propane-1,2-diol;
(S)-3-{4-[5-(2-diethylamino-6-methyl-pyrimidin-4-yl)-[1,2,4]oxadiazol-3-yl]-2,6-dimethyl-phenoxy}-propane-1,2-diol;
(R)-3-{4-[5-(2-diethylamino-6-methyl-pyrimidin-4-yl)-[1,2,4]oxadiazol-3-yl]-2,6-dimethyl-phenoxy}-propane-1,2-diol;
(S)-3-{4-[5-(2-(ethyl-methylamino)-6-methyl-pyrimidin-4-yl)-[1,2,4]oxadiazol-3-yl]-2,6-dimethyl-phenoxy}-propane-1,2-diol; and (R)-3-{4-[5-(2-(ethyl-methylamino)-6-methyl-pyrimidin-4-yl)-[1,2,4]oxadiazol-3-yl]-2,6-dimethyl-phenoxy}-propane-1,2-diol.

Further Examples of preferred compounds are selected from the group consisting of:

N-(3-{2-ethyl-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;

N-[3-(2-ethyl-4-{5-[2-(isobutyl-methyl-amino)-6-methyl-pyrimidin-4-yl]-[1,2,4]oxadiazol-3-yl}-6-methyl-phenoxy)-2-hydroxy-propyl]-2-hydroxy-acetamide;

N-(3-{4-[5-(2-cyclopropylamino-6-methyl-pyrimidin-4-yl)-[1,2,4]oxadiazol-3-yl]-2-ethyl-6-methyl-phenoxy}-2-hydroxy-propyl)-2-hydroxy-acetamide;

N-[3-(4-{5-[2-(cyclopropylmethyl-amino)-6-methyl-pyrimidin-4-yl]-[1,2,4]oxadiazol-3-yl}-2-ethyl-6-methyl-phenoxy)-2-hydroxy-propyl]-2-hydroxy-acetamide;

N-(3-{2-ethyl-4-[5-(6-ethyl-2-ethylamino-pyrimidin-4-yl)-[1,2,4]oxadiazol-3-yl]-6-methyl-phenoxy}-2-hydroxy-propyl)-2-hydroxy-acetamide;

N-(3-{2-ethyl-6-methyl-4-[5-(2-methylamino-6-propyl-pyrimidin-4-yl)-[1,2,4]oxadiazol-3-yl]-phenoxy}-2-hydroxy-propyl)-2-hydroxy-acetamide;

N—((S)-3-{2-ethyl-4-[5-(6-isobutyl-2-methylamino-pyrimidin-4-yl)-[1,2,4]oxadiazol-3-yl]-6-methyl-phenoxy}-2-hydroxy-propyl)-2-hydroxy-acetamide;

N-(3-{2-ethyl-4-[5-(2-isopropoxy-6-methyl-pyrimidin-4-yl)-[1,2,4]oxadiazol-3-yl]-6-methyl-phenoxy}-2-hydroxy-propyl)-2-hydroxy-acetamide;

N-(3-{2-ethyl-4-[5-(2-isobutoxy-6-methyl-pyrimidin-4-yl)-[1,2,4]oxadiazol-3-yl]-6-methyl-phenoxy}-2-hydroxy-propyl)-2-hydroxy-acetamide;

N-(3-{4-[5-(2-ethoxy-6-ethyl-pyrimidin-4-yl)-[1,2,4]oxadiazol-3-yl]-2-ethyl-6-methyl-phenoxy}-2-hydroxy-propyl)-2-hydroxy-acetamide;

N-(3-{2-ethyl-4-[5-(2-methoxy-6-propyl-pyrimidin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(6-isobutyl-2-methoxy-pyrimidin-4-yl)-[1,2,4]oxadiazol-3-yl]-6-methyl-phenoxy}-2-hydroxy-propyl)-2-hydroxy-acetamide;

N-(3-{2-chloro-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;

2-hydroxy-N-(2-hydroxy-3-{4-[5-(2-isopropylamino-6-methyl-pyrimidin-4-yl)-[1,2,4]oxadiazol-3-yl]-2-methoxy-6-methyl-phenoxy}-propyl)-acetamide;

N-(3-{2-chloro-4-[5-(2-isopropoxy-6-methyl-pyrimidin-4-yl)-[1,2,4]oxadiazol-3-yl]-6-methyl-phenoxy}-2-hydroxy-propyl)-2-hydroxy-acetamide;

3-{2-ethyl-4-[5-(2-isopropylamino-6-methyl-pyrimidin-4-yl)-[1,2,4]oxadiazol-3-yl]-6-methyl-phenoxy}-propane-1,2-diol;

3-{2-ethyl-4-[5-(2-isobutylamino-6-methyl-pyrimidin-4-yl)-[1,2,4]oxadiazol-3-yl]-6-methyl-phenoxy}-propane-1,2-diol;

3-{4-[5-(2-cyclopropylamino-6-methyl-pyrimidin-4-yl)-[1,2,4]oxadiazol-3-yl]-2-ethyl-6-methyl-phenoxy}-propane-1,2-diol;

3-{2-ethyl-4-[5-(6-ethyl-2-ethylamino-pyrimidin-4-yl)-[1,2,4]oxadiazol-3-yl]-6-methyl-phenoxy}-propane-1,2-diol;

3-{2-ethyl-4-[5-(6-ethyl-2-ethylamino-pyrimidin-4-yl)-[1,2,4]oxadiazol-3-yl]-6-methyl-phenoxy}-propane-1,2-diol;

3-{2-ethyl-4-[5-(6-isobutyl-2-methoxy-pyrimidin-4-yl)-[1,2,4]oxadiazol-3-yl]-6-methyl-phenoxy}-propane-1,2-diol;

3-{4-[5-(6-ethyl-2-ethylamino-pyrimidin-4-yl)-[1,2,4]oxadiazol-3-yl]-2,6-dimethyl-phenoxy}-propane-1,2-diol;

3-{4-[5-(6-ethyl-2-ethylamino-pyrimidin-4-yl)-[1,2,4]oxadiazol-3-yl]-2,6-dimethyl-phenoxy}-propane-1,2-diol;

3-{2-chloro-4-[5-(2-isopropylamino-6-methyl-pyrimidin-4-yl)-[1,2,4]oxadiazol-3-yl]-6-methyl-phenoxy}-propane-1,2-diol;

3-{4-[5-(2-isopropylamino-6-methyl-pyrimidin-4-yl)-[1,2,4]oxadiazol-3-yl]-2-methoxy-6-methyl-phenoxy}-propane-1,2-diol;

3-{2-chloro-4-[5-(2-isopropoxy-6-methyl-pyrimidin-4-yl)-[1,2,4]oxadiazol-3-yl]-6-methyl-phenoxy}-propane-1,2-diol;

N—((S)-3-{2-ethyl-4-[3-(2-isopropylamino-6-methyl-pyrimidin-4-yl)-[1,2,4]oxadiazol-5-yl]-6-methyl-phenoxy}-2-hydroxy-propyl)-2-hydroxy-acetamide;

3-(3-{4-[5-(2-diethylamino-6-methyl-pyrimidin-4-yl)-[1,2,4]oxadiazol-3-yl]-2-ethyl-6-methyl-phenoxy}-2-hydroxy-propylamino)-propionic acid; and 3-{2-ethyl-4-[5-(2-isopropylamino-6-methyl-pyrimidin-4-yl)-[1,2,4]oxadiazol-3-yl]-6-methyl-phenyl}-N-(2-hydroxy-ethyl)propionamide.

Further Examples of preferred compounds are further selected from the group consisting of:

N—((S)-3-{2-ethyl-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;

N—[(S)-3-(2-ethyl-4-{5-[2-(isobutyl-methyl-amino)-6-methyl-pyrimidin-4-yl]-[1,2,4]oxadiazol-3-yl}-6-methyl-phenoxy)-2-hydroxy-propyl]-2-hydroxy-acetamide;

N—((S)-3-{4-[5-(2-cyclopropylamino-6-methyl-pyrimidin-4-yl)-[1,2,4]oxadiazol-3-yl]-2-ethyl-6-methyl-phenoxy}-2-hydroxy-propyl)-2-hydroxy-acetamide;

N—[(S)-3-(4-{5-[2-(cyclopropylmethyl-amino)-6-methyl-pyrimidin-4-yl]-[1,2,4]oxadiazol-3-yl}-2-ethyl-6-methyl-phenoxy)-2-hydroxy-propyl]-2-hydroxy-acetamide;

N—((S)-3-{2-ethyl-4-[5-(6-ethyl-2-ethylamino-pyrimidin-4-yl)-[1,2,4]oxadiazol-3-yl]-6-methyl-phenoxy}-2-hydroxy-propyl)-2-hydroxy-acetamide;

N—((S)-3-{2-ethyl-6-methyl-4-[5-(2-methylamino-6-propyl-pyrimidin-4-yl)-[1,2,4]oxadiazol-3-yl]-phenoxy}-2-hydroxy-propyl)-2-hydroxy-acetamide;

N—((S)-3-{2-ethyl-4-[5-(6-isobutyl-2-methylamino-pyrimidin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(2-isopropoxy-6-methyl-pyrimidin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(2-isobutoxy-6-methyl-pyrimidin-4-yl)-[1,2,4]oxadiazol-3-yl]-6-methyl-phenoxy}-2-hydroxy-propyl)-2-hydroxy-acetamide;

N—((S)-3-{4-[5-(2-ethoxy-6-ethyl-pyrimidin-4-yl)-[1,2,4]oxadiazol-3-yl]-2-ethyl-6-methyl-phenoxy}-2-hydroxy-propyl)-2-hydroxy-acetamide;

N—((S)-3-{2-ethyl-4-[5-(2-methoxy-6-propyl-pyrimidin-4-yl)-[1,2,4]oxadiazol-3-yl]-6-methyl-phenoxy}-2-hydroxy-propyl)-2-hydroxy-acetamide;

N—((S)-3-{2-ethyl-4-[5-(6-isobutyl-2-methoxy-pyrimidin-4-yl)-[1,2,4]oxadiazol-3-yl]-6-methyl-phenoxy}-2-hydroxy-propyl)-2-hydroxy-acetamide;

N—((S)-3-{2-chloro-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;

2-hydroxy-N—((S)-2-hydroxy-3-{4-[5-(2-isopropylamino-6-methyl-pyrimidin-4-yl)-[1,2,4]oxadiazol-3-yl]-2-methoxy-6-methyl-phenoxy}-propyl)-acetamide;

N—((S)-3-{2-chloro-4-[5-(2-isopropoxy-6-methyl-pyrimidin-4-yl)-[1,2,4]oxadiazol-3-yl]-6-methyl-phenoxy}-2-hydroxy-propyl)-2-hydroxy-acetamide;

(S)-3-{2-ethyl-4-[5-(2-isopropylamino-6-methyl-pyrimidin-4-yl)-[1,2,4]oxadiazol-3-yl]-6-methyl-phenoxy}-propane-1,2-diol;

(S)-3-{2-ethyl-4-[5-(2-isobutylamino-6-methyl-pyrimidin-4-yl)-[1,2,4]oxadiazol-3-yl]-6-methyl-phenoxy}-propane-1,2-diol;

(S)-3-{4-[5-(2-cyclopropylamino-6-methyl-pyrimidin-4-yl)-[1,2,4]oxadiazol-3-yl]-2-ethyl-6-methyl-phenoxy}-propane-1,2-diol;

(S)-3-{2-ethyl-4-[5-(6-ethyl-2-ethylamino-pyrimidin-4-yl)-[1,2,4]oxadiazol-3-yl]-6-methyl-phenoxy}-propane-1,2-diol;

(R)-3-{2-ethyl-4-[5-(6-ethyl-2-ethylamino-pyrimidin-4-yl)-[1,2,4]oxadiazol-3-yl]-6-methyl-phenoxy}-propane-1,2-diol;

(S)-3-{2-ethyl-4-[5-(6-isobutyl-2-methoxy-pyrimidin-4-yl)-[1,2,4]oxadiazol-3-yl]-6-methyl-phenoxy}-propane-1,2-diol;

(S)-3-{4-[5-(6-ethyl-2-ethylamino-pyrimidin-4-yl)-[1,2,4]oxadiazol-3-yl]-2,6-dimethyl-phenoxy}-propane-1,2-diol;

(R)-3-{4-[5-(6-ethyl-2-ethylamino-pyrimidin-4-yl)-[1,2,4]oxadiazol-3-yl]-2,6-dimethyl-phenoxy}-propane-1,2-diol;

(S)-3-{2-chloro-4-[5-(2-isopropylamino-6-methyl-pyrimidin-4-yl)-[1,2,4]oxadiazol-3-yl]-6-methyl-phenoxy}-propane-1,2-diol;

(S)-3-{4-[5-(2-isopropylamino-6-methyl-pyrimidin-4-yl)-[1,2,4]oxadiazol-3-yl]-2-methoxy-6-methyl-phenoxy}-propane-1,2-diol;

(S)-3-{2-chloro-4-[5-(2-isopropoxy-6-methyl-pyrimidin-4-yl)-[1,2,4]oxadiazol-3-yl]-6-methyl-phenoxy}-propane-1,2-diol;

N—((S)-3-{2-ethyl-4-[3-(2-isopropylamino-6-methyl-pyrimidin-4-yl)-[1,2,4]oxadiazol-5-yl]-6-methyl-phenoxy}-2-hydroxy-propyl)-2-hydroxy-acetamide;

3-((S)-3-{4-[5-(2-diethylamino-6-methyl-pyrimidin-4-yl)-[1,2,4]oxadiazol-3-yl]-2-ethyl-6-methyl-phenoxy}-2-hydroxy-propylamino)-propionic acid; and 3-{2-ethyl-4-[5-(2-isopropylamino-6-methyl-pyrimidin-4-yl)-[1,2,4]oxadiazol-3-yl]-6-methyl-phenyl}-N-(2-hydroxy-ethyl)-propionamide.

The compounds of formula (I) and their pharmaceutically acceptable salts, can be used as a medicament, e.g. in the form of pharmaceutical compositions for enteral or parenteral administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

Diseases or disorders associated with an activated immune system which can be treated and/or prevented with the compounds of formula (I) include rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of formula (I) are selected from multiple sclerosis and psoriasis.

The present invention also relates to a method for the prevention or treatment of a disease or disorder mentioned herein comprising administering to a subject a pharmaceutically active amount of a compound of formula (I).

Furthermore, compounds of the formula (I) are also useful in combination with one or several immunomodulating agents for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of formula (I) for the preparation of a pharmaceutical composition, optionally for use in combination with one or several immunomodulating agents, for the prevention or treatment of the diseases and disorders mentioned herein.

The compounds of formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the formula (I) of the present invention can be prepared according to the general sequence of reactions outlined below. Only a few of the synthetic possibilities leading to compounds of formula (I) are described.

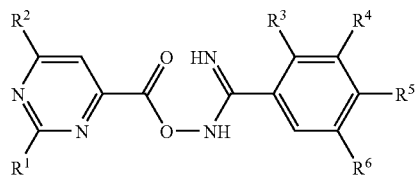

Structure 1

Compounds of formula (I) which represent a 5-pyrimidin-4-yl-[1,2,4]oxadiazole derivative, are prepared by reacting a compound of Structure 1 in a solvent such as dioxane, THF, dimethoxyethane, xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, methoxycarbonylsulfamoyl triethylammonium hydroxide (Burgess reagent), etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

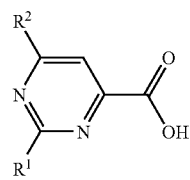

Structure 2

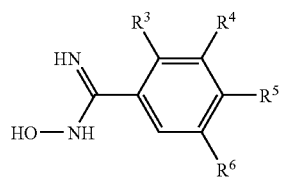

Structure 3

Compounds of Structure 1 may be prepared by reacting a compound of Structure 2 with a compound of Structure 3 in a solvent such as DMF, THF, DCM, etc. in the presence or absence of one or more coupling agents such as TBTU, DCC, EDC, HBTU, HOBt, CDI, PyBOP, etc. and in the presence or absence of a base such as triethylamine, DIPEA, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

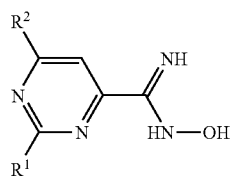

Structure 4

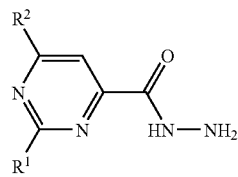

Structure 8

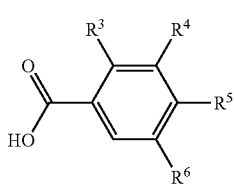

Structure 5

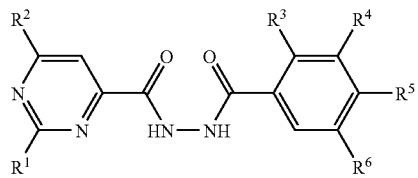

Structure 9

Compounds of formula (I) which represent a 3-pyrimidin-4-yl-[1,2,4]oxadiazole derivative are prepared in an analogous fashion (Lit.: e.g. C. T. Brain, J. M. Paul, Y. Loong, P. J. Oakley, *Tetrahedron Lett.* 40 (1999) 3275-3278) by reacting a compound of Structure 4 with a compound of Structure 5 and subsequent cyclisation of the corresponding hydroxyamidine ester intermediate. Compounds of Structure 5 are either commercially available or are prepared according to procedures described herein or according to procedures known to a person skilled in the art.

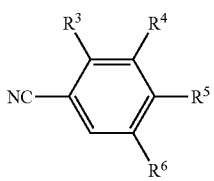

Structure 6

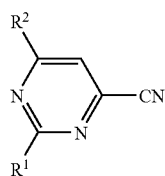

Structure 7

Compounds of Structure 3 and 4 may be prepared by reacting a compound of Structure 6 and 7, respectively, with hydroxylamine or one of its salts in a solvent such as methanol, ethanol, pyridine, etc. in the presence or absence of a base such as Na$_2$CO$_3$, K$_2$CO$_3$, triethylamine, KOtBu, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292). Compounds of Structure 6 are either commercially available or are prepared according to procedures described herein or according to procedures known to a person skilled in the art.

Methods that effect the transformation of a compound of Structure 2 into a compound of Structure 7, or the opposite, are known to a person skilled in the art.

Compounds of formula (I) which represent a 2-pyrimidin-4-yl-[1,3,4]oxadiazole or a 2-pyrimidin-4-yl-[1,3,4]thiadiazole derivative are prepared similarly by reacting a compound of Structure 2 with hydrazine (by using a coupling reagent such as TBTU, DCC, EDC, HBTU, PyBOP, HOBt, CDI, etc.) to form a compound of Structure 8 which is then coupled with a compound of Structure 5 to give a compound of Structure 9. A compound of Structure 9 can also be prepared by following the reverse reaction order, i.e. by first coupling a compound of Structure 5 with hydrazine followed by reacting the corresponding hydrazide intermediate with a compound of Structure 2. Dehydration of a compound of Structure 9 to form the desired 2-pyrimidin-4-yl-[1,3,4]oxadiazole derivative is affected by treating a compound of Structure 9 with a reagent such as POCl$_3$, CCl$_4$ or CBr$_4$ in combination with triphenylphosphine, P$_2$O$_5$, Burgess reagent, etc. in a solvent such as toluene, acetonitrile, dioxane, THF, CHCl$_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278). Likewise, 2-pyrimidin-4-yl-[1,3,4]thiadiazole derivatives are obtained by cyclizing a compound of Structure 9 with Lawesson's reagent optionally in combination with P$_2$S$_5$ in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, *J. Org. Chem.* 66 (2001) 7925-7929).

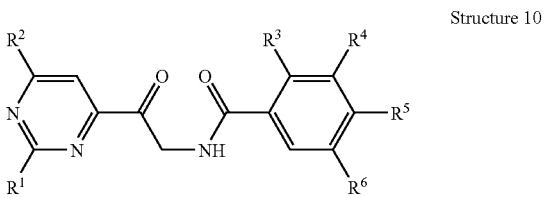

Structure 10

Compounds of formula (I) which represent a 5-pyrimidin-4-yl-oxazole or a 5-pyrimidin-4-yl-thiazole derivative are prepared by treating a compound of Structure 10 either with POCl$_3$, PCl$_5$, I$_2$ in combination with triphenylphosphine and triethylamine, trifluoroacetic anhydride, Burgess reagent, etc. in a solvent such as toluene, benzene, dioxane, THF, etc. at temperatures between 20 and 120° C., or with Lawesson's reagent, optionally in combination with $P_2S_5$, in the presence or absence of a solvent such as pyridine, toluene, THF, acetonitrile, etc. at elevated temperatures with or without microwave irradiation as mentioned above (Lit.: e.g. N. Sato, T. Shibata, M. Jitsuoka, T. Ohno, T. Takahashi, T. Hirohashi, T. Kanno, H. Iwaasa, A. Kanatani, T. Fukami, Takehiro, *Bioorg. & Med. Chem. Lett.* 14 (2004) 1761-1764). The compounds of Structure 10 are prepared by reacting a compound of Structure 11 with a compound of Structure 5. The aminoketone of Structure 11 can be prepared from a compound of Structure 2 by procedures given in the literature (e.g. J. L. LaMattina, *J. Heterocyclic Chem.* 20 (1983) 533-538; M. Pesson, M. Antoine, P. Girard, J. L. Benichon, S. Chabassier, P. De Lajudie, S. Patte, F. Roquet, G. Montay, *Eur. J. Med. Chem.* 15 (1980) 263-268). Compounds of formula (I) which represent a 2-pyrimidin-4-yl-oxazole or a 2-pyrimidin-4-yl-thiazole derivative are prepared in an analogous fashion from a compound of Structure 12 and a compound of Structure 2. The compounds of Structure 12 are prepared in analogy to literature procedures (e.g. W. A. Loughlin, L. C. Henderson, K. E. Elson, M. E. Murphy, Synthesis 2006, 1975-1980; L. Widler, J. Green, M. Missbach, M. Susa, E. Altmann, *Bioorganic & Medicinal Chemistry Letters* 11 (2001) 849-852; J. M. Holub et al., *Molecules* 9 (2004) 135-157).

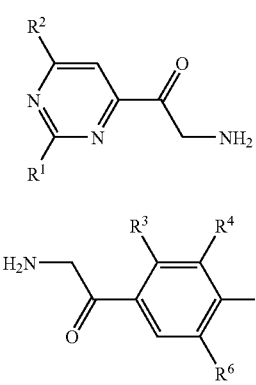

Structure 11

Structure 12

Depending on the nature of the functionalities present in the residues $R^3$ to $R^6$ in Structures 1, 3, 5, 6, 9, 10, and 12, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1999; P. J. Kocienski, Protecting Groups, Thieme Stuttgart, 1994). Alternatively, the desired residues $R^3$ to $R^6$, in particular $R^5$, may also be introduced in later steps that follow the A-ring formation between the pyrimidine and the phenyl rings according to procedures described herein or according to procedures known to a person skilled in the art.

Alternatively, the bonds between the pyrimidine or the phenyl ring and the central 5-membered heteroaromatic ring can also be formed by applying palladium catalysed cross coupling reactions.

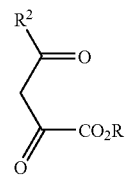

Structure 13

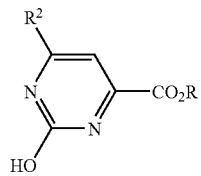

Structure 14

Compounds of Structure 2 may be prepared by reacting a 2,4-dioxo-alkanoic ester (Structure 13, wherein $R^2$ represents preferably a methyl or an ethyl) with urea in acidic medium in the presence or absence of an additional solvent such as methanol, ethanol, dioxane, etc., preferably at temperatures above 50° C. to give a compound of Structure 14. The compounds of Structure 14 can then be reacted with $POCl_3$ (Lit.: e.g. Palanki, M. S. S., Erdman, P. E., Gayo-Fung, L. M., Shelvin, G. I., Sullivan, R. W., Suto, M. J., Goldman, M. E., Ransone, L. J., Bennett, B. L., Manning, A. M., *J. Med. Chem.* 43 (2000) 3995-4004) to give a compound of Structure 15, which can be hydrolysed to a compound of Structure 16. The compounds of Structure 16 can be reacted with the appropriate amine or alcohol in combination with a base such as Hünig's base, in the presence or absence of an additional solvent such as THF, dioxane etc., preferably at temperatures above 50° C. to give a compound of Structure 2.

Compounds of Structure 13 are either commercially available or are prepared according to procedures known to a person skilled in the art.

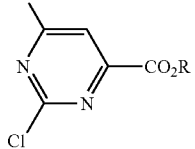

Structure 15

Structure 16

Alternatively, the compounds of Structure 2 may also be prepared by reacting a compound of Structure 17 with an alkenyl boron derivative (e.g. 2,4,6-trivinyl-cyclotriboroxane) under Suzuki conditions (Lit.: e.g. F. Kerins, D. F. O'Shea, *J. Org. Chem.* 67 (2002) 4968-4971). The obtained 2-chloro-6-alkenyl-pyrimidine carboxylate derivative is reacted with the appropriate amine or alcohol, then hydrogenated and finally hydrolyzed to the corresponding compound of Structure 2.

Structure 17

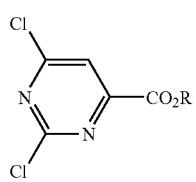

Compounds of Structure 17 are either commercially available or may be prepared by reacting the methyl ester of orotic acid with $POCl_3$ (Lit.: e.g. S. Miltschitzky, V. Michlova, S. Stadbauer, B. Koenig, *Heterocycles* 67 (2006) 135-160).

In case $R^1$ represents a monoalkylamino group, the corresponding monoalkylamino-pyrimidine derivatives that may occur in the course of the synthesis of compounds of formula (I), may require temporary protection at the secondary amine function.

Structure 18

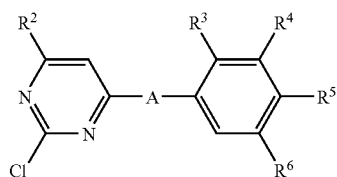

The above described reaction sequences that allow the introduction of the two residues $R^1$ and $R^2$ may also be applied to a compound in which the scaffold has already been further elaborated. For instance, the desired residue $R^1$ may also be introduced in a later step from a compound of Structure 18 which can be synthesised by methods analogous to those described herein, e.g. by the coupling-cyclisation sequence of the pyrimidine compounds of Structure 16 with the phenyl compounds of Structure 3.

Alternatively, the compounds of Structure 2 may also be prepared by reacting a compound of Structure 13 with S-methylisothiourea sulphate in the presence or absence of an additional solvent such as methanol, ethanol, dioxane, etc., preferably at temperatures above 50° C. to give a compound of Structure 19. The compounds of Structure 19 can then be hydrolysed under basic conditions to the corresponding carboxylic acid derivatives which are reacted with oxidative agent such as mCPBA to give the compounds of Structure 20 (Lit.: e.g. Z. Budesinsky, F. Roubinek, *Collection Czechoslov. Chem. Commun.* 26 (1961), 2871-2885). The compounds of Structure 20 can be reacted with the appropriate amine or alcohol in combination with a base such as Hünig's base or NaOH, in the presence or absence of an additional solvent such as THF, dioxane etc., preferably at temperatures above 50° C. to give a compound of Structure 2. Compounds of Structure 2 with $R^1=C_{1-4}$ alkoxy can also be accessible by reacting compounds of Structure 19 with mCPBA followed by nucleophilic displacement with the appropriate alkoholate.

Structure 19

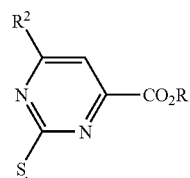

Structure 20

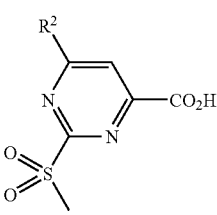

EXAMPLES

The following examples illustrate the invention but do not at all limit the scope thereof.

All temperatures are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; retention times or LC-MS marked with * refer to an LC run under basic conditions, i.e. eluting with a gradient of MeCN in water containing 13 mM of ammonium hydroxide, otherwise identical conditions; by TLC (TLC-plates from Merck, Silica gel 60 $F_{254}$); or by melting point. Compounds are purified by preparative HPLC (column: X-Bridge PrepC18, 30×75 mm, 5 µm; gradient: 10-95% acetonitrile in water containing 0.5% of formic acid) or by MPLC (Labomatic MD-80-100 pump, Linear UVIS-201 detector, column: 350× 18 mm, Labogel-RP-18-5s-100, gradient: 10% methanol in water to 100% methanol). Racemates can be separated into their enantiomers by preparative HPLC (column: ChiralPaK AD 20×250 mm, 5 µm, 15% ethanol in hexane).

ABBREVIATIONS

As Used Herein

| | |
|---|---|
| AcOH | acetic acid |
| aq. | aqueous |
| Boc | tert-butoxycarbonyl |
| BSA | bovine serum albumin |
| CC | column chromatography |
| CDI | carbonyl diimidazole |
| DCC | dicyclohexyl carbodiimide |
| DCM | dichloromethane |
| DEAD | diethyl azodicarboxylate |
| DIPEA | diisopropyl-ethylamine, Hünig's base, ethyl-diisopropylamine |
| DMF | dimethylformamide |
| DMSO | dimethylsulfoxide |
| EA | ethyl acetate |

-continued

| | |
|---|---|
| EDC | N-(3-dimethylaminopropyl)-N'-ethyl-carbodiimide |
| eq. | equivalent(s) |
| Et | ethyl |
| EtOAc | ethyl acetate |
| Ex. | Example(s) |
| h | hour(s) |
| HBTU | O-(benzotriazol-1-yl)-N,N,N',N'-tetramethyluronium hexafluorophosphate |
| HOBt | 1-hydroxybenzotriazole |
| HPLC | high performance liquid chromatography |
| iBu | isobutyl |
| iPr | isopropyl |
| KOtBu | potassium tert-butoxide |
| LC-MS | liquid chromatography-mass spectrometry |
| Lit. | Literature |
| mCPBA | meta-chloroperbenzoic acid |
| Me | methyl |
| MeOH | methanol |
| min | minute(s) |
| MPLC | medium pressure liquid chromatography |
| NaOAc | sodium acetate |
| nPr | n-propyl |
| org. | organic |
| Ph | phenyl |
| prep. | preparative |
| PyBOP | benzotriazol-1-yl-oxy-tris-pyrrolidino-phosphonium-hexafluoro-phosphate |
| rt | room temperature |
| sat. | saturated |
| S1P | sphingosine 1-phosphate |
| TBTU | 2-(1H-benzotriazole-1-yl)-1,2,3,3-tetramethyluronium tetrafluoroborate |
| TFA | trifluoroacetic acid |
| TFFA | trifluoroacetic anhydride |
| THF | tetrahydrofuran |
| TLC | thin layer chromatography |
| $t_R$ | retention time |

6-Methyl-2-propylamino-pyrimidine-4-carboxylic acid a) To a solution of commercially available methyl-2-chloro-6-methylpyrimidine-4-carboxylate (6.00 g, 32.15 mmol) in acetonitrile (500 mL), 1M aq. solution of NaOH (48.2 mL) is added at 0° C. The mixture is stirred at 0° C. for 1 h then acidified with 25% aq. HCl (7 mL). Volatiles are evaporated and the aq. solution is extracted with ethylacetate, washed with brine, dried over $Na_2SO_4$, filtered and concentrated to give 2-chloro-6-methylpyrimidine-4-carboxylic acid (4.22 g) as a yellow crystalline solid; LC-MS: $t_R$=0.42 min, $[M+H]^+$=172.96; $^1$H NMR ($D_6$-DMSO): δ 2.58 (s, 3H), 7.95 (s, 1H), 14.1 (s br, 1H).

b) A solution of 2-chloro-6-methylpyrimidine-4-carboxylic acid (100 mg, 0.58 mmol) and propylamine (0.48 mL) in dioxane (1 mL) is stirred at 70° C. for 18 h. The reaction mixture is concentrated and purified by prep. HPLC (X-Bridge) to give 6-methyl-2-propylamino-pyrimidine-4-carboxylic acid (81 mg) as a yellow crystalline solid; LC-MS: $t_R$=0.56 min, $[M+H]^+$=196.08; $^1$H NMR ($D_6$-DMSO): δ 0.89 (t, J=7.3 Hz, 3H), 1.53 (m, 2H), 2.32 (s, 3H), 3.25 (m, 2H), 6.92 (s, 1H), 7.36 (s br, 1H), 13.2 (s br, 1H).

6-Methyl-2-methylamino-pyrimidine-4-carboxylic acid

The title compound is obtained as a yellow solid (230 mg) in analogy to 6-methyl-2-propylamino-pyrimidine-4-carboxylic acid starting from 2-chloro-6-methylpyrimidine-4-carboxylic acid (265 mg, 1.54 mmol) and 41% methylamine in water; LC-MS: $t_R$=0.32 min, $[M+H]^+$=168.04.

2-Ethylamino-6-methyl-pyrimidine-4-carboxylic acid

The title compound is obtained as a yellow solid (233 mg) in analogy to 6-methyl-2-propylamino-pyrimidine-4-carboxylic acid starting from 2-chloro-6-methylpyrimidine-4-carboxylic acid (265 mg, 1.54 mmol) and 2M ethylamine in THF; LC-MS: $t_R$=0.47 min, $[M+H]^+$=182.05.

2-Isopropylamino-6-methyl-pyrimidine-4-carboxylic acid

The title compound is obtained as a yellow solid (244 mg) in analogy to 6-methyl-2-propylamino-pyrimidine-4-carboxylic acid starting from 2-chloro-6-methylpyrimidine-4-carboxylic acid (265 mg, 1.54 mmol) and isopropylamine; LC-MS: $t_R$=0.55 min, $[M+H]^+$=196.05.

2-Isobutylamino-6-methyl-pyrimidine-4-carboxylic acid

The title compound is obtained as a yellow solid (271 mg) in analogy to 6-methyl-2-propylamino-pyrimidine-4-carboxylic acid starting from 2-chloro-6-methylpyrimidine-4-carboxylic acid (265 mg, 1.54 mmol) and isobutylamine; LC-MS: $t_R$=0.64 min, $[M+H]^+$=210.08.

2-Dimethylamino-6-methyl-pyrimidine-4-carboxylic acid

The title compound is obtained as a yellow solid (238 mg) in analogy to 6-methyl-2-propylamino-pyrimidine-4-carboxylic acid starting from 2-chloro-6-methylpyrimidine-4-carboxylic acid (265 mg, 1.54 mmol) and 2M dimethylamine in THF; LC-MS: $t_R$=0.44 min, $[M+H]^+$=182.08.

2-Diethylamino-6-methyl-pyrimidine-4-carboxylic acid

The title compound is obtained as a yellow solid (192 mg) in analogy to 6-methyl-2-propylamino-pyrimidine-4-carboxylic acid starting from 2-chloro-6-methylpyrimidine-4-carboxylic acid (265 mg, 1.54 mmol) and diethylamine; LC-MS: $t_R$=0.64 min, $[M+H]^+$=210.07.

2-(Ethyl-methyl)amino-6-methyl-pyrimidine-4-carboxylic acid

The title compound is obtained as a yellow solid (235 mg) in analogy to 6-methyl-2-propylamino-pyrimidine-4-carboxylic acid starting from 2-chloro-6-methylpyrimidine-4-carboxylic acid (265 mg, 1.54 mmol) and N-ethylmethylamine; LC-MS: $t_R$=0.54 min, $[M+H]^+$=196.08.

2-N-Isobutyl-N-methyl-amino-6-methyl-pyrimidine-4-carboxylic acid

The title compound is obtained as a yellow solid (235 mg) in analogy to 6-methyl-2-propylamino-pyrimidine-4-carboxylic acid starting from 2-chloro-6-methylpyrimidine-4-carboxylic acid (300 mg, 1.74 mmol) and N-isobutylmethylamine; LC-MS: $t_R$=0.80 min, $[M+H]^+$=224.21.

6-Methyl-2-pyrrolidin-1-yl-pyrimidine-4-carboxylic acid

The title compound is obtained as a yellow solid (200 mg) in analogy to 6-methyl-2-propylamino-pyrimidine-4-carboxylic acid starting from 2-chloro-6-methylpyrimidine-4-carboxylic acid (200 mg, 1.16 mmol) and pyrrolidine; LC-MS: $t_R$=0.50 min, [M+H]$^+$=208.00.

2-Cyclopropylamino-6-methyl-pyrimidine-4-carboxylic acid

The title compound is obtained as a yellow solid (336 mg) in analogy to 6-methyl-2-propylamino-pyrimidine-4-carboxylic acid starting from 2-chloro-6-methylpyrimidine-4-carboxylic acid (500 mg, 2.90 mmol) and cyclopropylamine; LC-MS: $t_R$=0.44 min, [M+H]$^+$=193.98. $^1$H NMR (D$_6$-DMSO) δ 0.47 (m, 2H), 0.66 (m, 2H), 2.35 (s, 3H), 2.79 (m, 1H), 6.99 (s, 1H), 7.55 (s br, 1H).

2-(Cyclopropylmethyl-amino)-6-methyl-pyrimidine-4-carboxylic acid

The title compound is obtained as a yellow oil (230 mg) in analogy to 6-methyl-2-propylamino-pyrimidine-4-carboxylic acid starting from 2-chloro-6-methylpyrimidine-4-carboxylic acid (250 mg, 1.45 mmol) and cyclopropylmethylamine; LC-MS: $t_R$=0.57 min, [M+H]$^+$=208.00.

2-Methoxy-6-methyl-pyrimidine-4-carboxylic acid

A suspension of methyl-2-chloro-6-methylpyrimidine-4-carboxylate (5.0 g) in 2N aq. NaOH (67 mL) and methanol (67 mL) is stirred at rt for 24 h. Methanol is evaporated and the aq. phase is acidified with 25% aq. HCl at 0° C. A beige crystalline solid crushes out. It is filtered, rinsed with water and heptane and dried (3.0 g); LC-MS: $t_R$=0.55 min, [M+H]$^+$=169.01; $^1$H NMR (D$_6$-DMSO): δ 2.50 (s, 3H), 3.94 (s, 3H), 7.52 (s, 1H), 13.7 (s br, 1H).

2-Ethoxy-6-methyl-pyrimidine-4-carboxylic acid

A solution of 2-chloro-6-methylpyrimidine-4-carboxylic acid (265 mg, 1.54 mmol) and Hünig's base (0.8 mL) in ethanol (1.79 mL) is stirred at 70° C. for 24 h. Ethanol is evaporated and the aq. phase is acidified with 25% aq. HCl at 0° C., concentrated and purified by prep. HPLC (X-Bridge) to give 2-ethoxy-6-methyl-pyrimidine-4-carboxylic acid (201 mg) as a yellow solid; LC-MS: $t_R$=0.63 min, [M+H]$^+$=183.04.

6-Methyl-2-propoxy-pyrimidine-4-carboxylic acid

The title compound is obtained as a yellow solid (174 mg) in analogy to 2-ethoxy-6-methyl-amino-pyrimidine-4-carboxylic acid starting from 2-chloro-6-methylpyrimidine-4-carboxylic acid (265 mg, 1.54 mmol) and n-propanol; LC-MS: $t_R$=0.72 min, [M+H]$^+$=197.06.

2-Isopropoxy-6-methyl-pyrimidine-4-carboxylic acid

The title compound is obtained as a yellow solid (47 mg) in analogy to 2-ethoxy-6-methyl-amino-pyrimidine-4-carboxylic acid starting from 2-chloro-6-methylpyrimidine-4-carboxylic acid (265 mg, 1.54 mmol) and isopropanol; LC-MS: $t_R$=0.71 min, [M+H]$^+$=197.07.

2-Isobutoxy-6-methyl-pyrimidine-4-carboxylic acid

The title compound is obtained as a yellow solid (16 mg) in analogy to 2-ethoxy-6-methyl-amino-pyrimidine-4-carboxylic acid starting from 2-chloro-6-methylpyrimidine-4-carboxylic acid (265 mg, 1.54 mmol) and isobutanol; LC-MS: $t_R$=0.80 min, [M+H]$^+$=211.03.

6-Ethyl-2-methylsulfanyl-pyrimidine-4-carboxylic acid ethyl ester

A solution of S-methylisothiourea sulphate (874 mg, 4.65 mmol) and 2,4-dioxohexanoic acid ethyl ester (800 mg, 4.65 mmol) in ethanol (4 mL) is heated to 80° C. for 48 h. The reaction mixture is then filtered, evaporated and purified by prep. TLC (using heptane/EA 1/1 as eluent) to give 590 mg of 6-ethyl-2-methylsulfanyl-pyrimidine-4-carboxylic acid ethyl ester as a yellow oil; LC-MS: $t_R$=0.91 min, [M+H]$^+$=227.22. $^1$H NMR (D$_6$-DMSO): δ 1.24 (t, J=7.5 Hz, 3H), 1.34 (t, J=7.0 Hz, 3H), 2.56 (s, 3H), 2.81 (q, J=7.5 Hz, 2H), 4.37 (q, J=7.0 Hz, 2H), 7.58 (s, 1H).

6-Ethyl-2-methanesulfonyl-pyrimidine-4-carboxylic acid ethyl ester

To a solution of 6-ethyl-2-methylsulfanyl-pyrimidine-4-carboxylic acid ethyl ester (600 mg, 2.65 mmol) in DCM (20 mL) at 0° C., mCPBA (1.37 g, 5.57 mmol) is added. The reaction mixture is stirred for 12 h at rt, then quenched with 10% aq. Na$_2$S$_2$O$_3$ and extracted with DCM (3×40 mL). The combined org. layers are washed with sat. aq. NaHCO$_3$, dried over MgSO$_4$, filtered and evaporated under reduced pressure. The crude material is then purified by CC (EA/Heptane 1/9) to give 333 mg of the title compound as a yellow oil; LC-MS: $t_R$=0.80 min, [M+H]$^+$=259.07.

6-Ethyl-2-methanesulfonyl-pyrimidine-4-carboxylic acid a) To a solution of 6-ethyl-2-methylsulfanyl-pyrimidine-4-carboxylic acid ethyl ester (590 mg, 2.61 mmol) in ethanol (12 mL) and THF (12 mL), 2M aq. LiOH (4 mL) is added. The mixture is stirred for 12 h at rt before neutralizing with 1N aq. HCl. The aq. solution is extracted 3 times with ethylacetate and the combined org. layers are evaporated to dryness to give 510 mg of 6-ethyl-2-methylsulfanyl-pyrimidine-4-carboxylic acid as a white solid; LC-MS: $t_R$=0.75 min, [M+H]$^+$=199.02.

b) To a solution of 6-ethyl-2-methylsulfanyl-pyrimidine-4-carboxylic acid (510 mg, 2.57 mmol) in DCM (15 mL) at 0° C., mCPBA (1.33 g, 5.40 mmol) is added. The reaction mixture is stirred for 12 h at rt, then quenched with 10% aq. Na$_2$S$_2$O$_3$ and extracted with DCM (3×20 mL). The combined org. layers are washed with sat. aq. NaHCO$_3$, dried over MgSO$_4$, filtered and evaporated under reduced pressure. The crude material is then purified by prep. TLC (DCM/MeOH 4/1) to give 325 mg of the title compound as a yellow oil; LC-MS: $t_R$=0.54 min, [M+H]$^+$=231.05.

2-Methylsulfanyl-6-propyl-pyrimidine-4-carboxylic acid ethyl ester

The title compound is obtained as a yellow oil (3.35 g) in analogy to 6-ethyl-2-methylsulfanyl-pyrimidine-4-carboxylic acid ethyl ester starting from 2,4-dioxo-heptanoic acid ethyl ester (4.0 g) and S-methyl-isothiourea sulfate; LC-MS: $t_R$=0.99 min, [M+H]$^+$=240.97. $^1$H NMR (CDCl$_3$) δ 1.00 (m, 3H), 1.44 (m, 3H), 1.82 (m, 2H), 2.64 (s, 3H), 2.77 (m, 2H), 4.47 (q, J=7.3 Hz, 2H), 7.47 (s, 1H).

2-Methanesulfonyl-6-propyl-pyrimidine-4-carboxylic acid ethyl ester

The title compound is obtained as a yellow solid (107 mg) in analogy to 6-ethyl-2-methanesulfonyl-pyrimidine-4-carboxylic acid ethyl ester starting from 2-methylsulfanyl-6-propyl-pyrimidine-4-carboxylic acid ethyl ester; LC-MS: $t_R$=0.85 min, $[M+H]^+$=272.96.

2-Methanesulfonyl-6-propyl-pyrimidine-4-carboxylic acid

The title compound is obtained as a yellow solid (371 mg) in analogy to 6-ethyl-2-methanesulfonyl-pyrimidine-4-carboxylic acid starting from 2-methylsulfanyl-6-propyl-pyrimidine-4-carboxylic acid ethyl ester; LC-MS: $t_R$=0.65 min, $[M+H]^+$=244.95.

6-Isobutyl-2-methylsulfanyl-pyrimidine-4-carboxylic acid ethyl ester

The title compound is obtained as a yellow oil (2.31 g) in analogy to 6-ethyl-2-methylsulfanyl-pyrimidine-4-carboxylic acid ethyl ester starting from 6-methyl-2,4-dioxo-heptanoic acid ethyl ester (3.5 g) and S-methyl-isothiourea sulfate; LC-MS: $t_R$=1.03 min, $[M+H]^+$=254.98. $^1$H NMR (CDCl$_3$) δ 0.98 (d, J=6.8 Hz, 6H), 1.45 (t, J=7.0 Hz, 3H), 2.20 (m, 1H), 2.64 (s, 3H), 2.67 (d, J=7.0 Hz, 2H), 4.48 (q, J=7.0 Hz, 2H), 7.44 (s, 1H).

6-Isobutyl-2-methanesulfonyl-pyrimidine-4-carboxylic acid ethyl ester

The title compound is obtained as a yellow solid (107 mg) in analogy to 6-ethyl-2-methanesulfonyl-pyrimidine-4-carboxylic acid ethyl ester starting from 6-isobutyl-2-methylsulfanyl-pyrimidine-4-carboxylic acid ethyl ester; LC-MS: $t_R$=0.91 min, $[M+H]^+$=286.97.

6-Isobutyl-2-methanesulfonyl-pyrimidine-4-carboxylic acid

The title compound is obtained as a beige solid (610 mg) in analogy to 6-ethyl-2-methanesulfonyl-pyrimidine-4-carboxylic acid starting from 6-isobutyl-2-methylsulfanyl-pyrimidine-4-carboxylic acid ethyl ester; LC-MS: $t_R$=0.72 min, $[M+H]^+$=258.93.

6-Ethyl-2-ethylamino-pyrimidine-4-carboxylic acid

To a solution of 6-ethyl-2-methanesulfonyl-pyrimidine-4-carboxylic acid (325 mg, 1.41 mmol) in THF (5 mL) is added 70% ethylamine in water (2.0 mL). The mixture is stirred at 70° C. overnight. It is then evaporated to dryness and purified by prep. TLC (DCM/7N NH$_3$ in MeOH 4/1) to give 6-ethyl-2-ethylamino-pyrimidine-4-carboxylic acid as a yellow oil (200 mg); LC-MS: $t_R$=0.58 min, $[M+H]^+$=194.07. $^1$H NMR (CDCl$_3$): δ 1.34 (m, 6H), 2.84 (d, J=7.5 Hz, 2H), 3.64 (m, 2H), 7.26 (s, 1H), 11.0 (s br, 1H).

2-Methylamino-6-propyl-pyrimidine-4-carboxylic acid

A solution of 40% aq. methylamine (5 mL) and 2-methanesulfonyl-6-propyl-pyrimidine-4-carboxylic acid (150 mg, 0.614 mmol) is heated to 70° C. for 2 h. The reaction mixture is then evaporated and the crude compound is dissolved in 3N NaOH solution (10 mL). The aq. solution is washed with EtOAc (5 mL), is then adjusted to pH 3 with 25% aq. HCl and finally extracted with DCM (3×15 mL). The combined DCM extracts are dried over MgSO$_4$, filtered and evaporated to give 2-methylamino-6-propyl-pyrimidine-4-carboxylic acid as a beige powder (128 mg); LC-MS: $t_R$=0.56 min, $[M+H]^+$=196.00.

6-Isobutyl-2-methylamino-pyrimidine-4-carboxylic acid

The title compound is obtained as a beige solid (84 mg) in analogy to 2-methylamino-6-propyl-pyrimidine-4-carboxylic acid starting from 6-isobutyl-2-methanesulfonyl-pyrimidine-4-carboxylic acid; LC-MS: $t_R$=0.63 min, $[M+H]^+$=209.99.

2-Dimethylamino-6-isobutyl-pyrimidine-4-carboxylic acid

The title compound is obtained as a beige solid (132 mg) in analogy to 2-methylamino-6-propyl-pyrimidine-4-carboxylic acid starting from 6-isobutyl-2-methanesulfonyl-pyrimidine-4-carboxylic acid and 40% aq. dimethylamine; LC-MS: $t_R$=0.78 min, $[M+H]^+$=224.03.

6-Isobutyl-2-isopropylamino-pyrimidine-4-carboxylic acid

The title compound is obtained as a beige solid (103 mg) in analogy to 2-methylamino-6-propyl-pyrimidine-4-carboxylic acid starting from 6-isobutyl-2-methanesulfonyl-pyrimidine-4-carboxylic acid and isopropylamine; LC-MS: $t_R$=0.77 min, $[M+H]^+$=238.04.

2-Ethoxy-6-ethyl-pyrimidine-4-carboxylic acid

To a solution of 6-ethyl-2-methanesulfonyl-pyrimidine-4-carboxylic acid ethyl ester (100 mg, 0.39 mmol) in ethanol (4 mL), sodium ethylate (134 mg, 1.94 mmol) is added. The reaction mixture is stirred for 2 h, ethanol is evaporated and the residue is dissolved in EtOAc (25 mL). The org. solution is washed with 1M aq. KHSO$_4$, followed by brine, dried over MgSO$_4$, filtered and evaporated give 2-ethoxy-6-ethyl-pyrimidine-4-carboxylic acid as a yellow oil (35 mg); LC-MS: $t_R$=0.72 min, $[M+H]^+$=197.07.

2-Methoxy-6-propyl-pyrimidine-4-carboxylic acid

The title compound is obtained as a beige solid (84 mg) in analogy to 2-ethoxy-6-ethyl-pyrimidine-4-carboxylic acid starting from 2-methanesulfonyl-6-propyl-pyrimidine-4-carboxylic acid ethyl ester, KOtBu and methanol; LC-MS: $t_R$=0.71 min, $[M+H]^+$=196.96.

6-Isobutyl-2-methoxy-pyrimidine-4-carboxylic acid

The title compound is obtained as a yellow oil (82 mg) in analogy to 2-ethoxy-6-ethyl-pyrimidine-4-carboxylic acid starting from 6-isobutyl-2-methanesulfonyl-pyrimidine-4-carboxylic acid ethyl ester, KOtBu and methanol; LC-MS: $t_R$=0.77 min, $[M+H]^+$=210.96.

3-Ethyl-4-hydroxy-5-methyl-benzaldehyde

3-Ethyl-4-hydroxy-5-methyl-benzaldehyde is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); $^1$H NMR (CDCl$_3$): δ 1.28 (t, J=7.6 Hz, 3H), 2.32 (s, 3H), 2.69 (q, J=7.6 Hz, 2H), 5.30 (s br, 1H), 7.58-7.53 (m, 2H), 9.83 (s, 1H).

4-Benzyloxy-3-ethyl-5-methyl-benzaldehyde

Potassium carbonate (4.38 g, 32 mmol) is added to a stirred solution of 3-ethyl-4-hydroxy-5-methyl-benzaldehyde (2.6 g, 16 mmol) in acetone (70 mL). Benzylbromide (2.07 mL, 17 mmol) is then added dropwise and the reaction mixture is heated to 60° C. for 3 h. The suspension is filtered, the filtrate is evaporated and the crude product is purified by CC on silica gel eluting with heptane:EA 9:1 to give 4-benzyloxy-3-ethyl-5-methyl-benzaldehyde (3.66 g) as a colorless oil; $^1$H NMR (CDCl$_3$): δ 1.28 (t, J=7.5 Hz, 3H), 2.40 (s, 3H), 2.76 (q, J=7.5 Hz, 2H), 4.90 (s, 2H), 7.50-7.35 (m, 5H), 7.62 (s, 1H), 7.65 (s, 1H), 9.94 (s, 1H).

4-Benzyloxy-3-ethyl-5-methyl-benzoic acid

4-Benzyloxy-3-ethyl-5-methyl-benzaldehyde (1.4 g, 5.5 mmol) is dissolved in acetone (20 mL) and is slowly added to a cold solution of KMnO$_4$ (1.74 g, 11 mmol) in 20% aq. acetone (25 mL). The reaction mixture is stirred at rt for 3 h, and then acetone is evaporated. The remaining aq. phase is acidified with 10% citric acid (60 mL) and is extracted with DCM (80 mL, 60 mL, 60 mL). The combined org. extracts are washed with brine, dried over MgSO$_4$, filtered and evaporated. The crude product is purified by CC on silica gel eluting with heptane:EA (5:1 to 2:1) to give 4-benzyloxy-3-ethyl-5-methyl-benzoic acid (1.16 g) as an off-white solid; LC-MS: $t_R$=0.56 min*; $^1$H NMR (CDCl$_3$): δ 1.29 (t, J=7.5 Hz, 3H), 2.39 (s, 3H), 2.75 (q, J=7.5 Hz, 2H), 4.90 (s, 2H), 7.53-7.36 (m, 5H), 7.86 (s, 1H), 7.89 (s, 1H), 12.0 (s br, 1H).

3-Ethyl-4-hydroxy-5-methyl-benzonitrile

The title compound is prepared from 3-ethyl-4-hydroxy-5-methyl-benzaldehyde following literature procedures (A. K. Chakraborti, G. Kaur, *Tetrahedron* 55 (1999) 13265-13268); LC-MS: $t_R$=0.90 min; $^1$H NMR (CDCl$_3$): δ 1.24 (t, J=7.6 Hz, 3H), 2.26 (s, 3H), 2.63 (q, J=7.6 Hz, 2H), 5.19 (s, 1H), 7.30 (s, 2H).

(S)-4-(3-Amino-2-hydroxypropoxy)-3-ethyl-5-methylbenzonitrile a) To a solution of 3-ethyl-4-hydroxy-5-methyl-benzonitrile (5.06 g, 31.4 mmol) in THF (80 mL), PPh$_3$ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane:EA 7:3 to give 3-ethyl-5-methyl-4-oxiranylmethoxy-benzonitrile (5.85 g) as a yellow oil; LC-MS: $t_R$=0.96 min; [M+42]$^+$=259.08.

b) The above epoxide is dissolved in 7 N NH$_3$ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g) as a yellow oil; LC-MS: $t_R$=0.66 min; [M+H]$^+$=235.11.

N—((S)-3-[2-Ethyl-4-(N-hydroxycarbamimidoyl)-6-methyl-phenoxy]-2-hydroxy-propyl)-2-hydroxy-acetamide a) To a solution of (S)-4-(3-amino-2-hydroxypropoxy)-3-ethyl-5-methylbenzonitrile (6.23 g, 26.59 mmol), glycolic acid (2.43 g, 31.9 mmol), HOBt (4.31 g, 31.9 mmol) and EDC hydrochloride (6.12 g, 31.9 mmol) are added. The mixture is stirred at rt for 18 h before it is diluted with sat. aq. NaHCO$_3$ and extracted twice with EA. The combined org. extracts are dried over MgSO$_4$, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g) as a yellow oil; LC-MS: $t_R$=0.74 min; [M+H]$^+$=293.10; $^1$H NMR (CDCl$_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (s, br, 3H), 7.06 (m, 1H), 7.36 (s, 1H), 7.38 (s, 1H).

b) The above nitrile is converted to the N-hydroxy-benzamidine according to literature procedures (e.g. E. Meyer, A. C. Joussef, H. Gallardo, *Synthesis* 2003, 899-905); LC-MS: $t_R$=0.51 min; [M+H]$^+$=326.13; $^1$H NMR (D$_6$-DMSO): δ 1.17 (t, J=7.4 Hz, 3H), 2.24 (s, 3H), 2.62 (q, J=7.4 Hz, 2H), 3.23 (m, 1H), 3.43 (m, 1H), 3.67 (m, 2H), 3.83 (s, 2H), 3.93 (m, 1H), 5.27 (s br, 1H), 5.58 (s br, 1H), 5.70 (s, 2H), 7.34 (s, 1H), 7.36 (s, 1H), 7.67 (m, 1H), 9.46 (s br, 1H).

rac-4-(2,2-Dimethyl-[1,3]dioxolan-4-ylmethoxy)-N-hydroxy-3,5-dimethyl-benzamidine The title compound is prepared by O-alkylating commercially available 4-hydroxy-3,5-dimethyl-benzonitrile with D,L-alpha-beta-isopropyliden glycerol under Mitsunobu conditions in the presence of PPh$_3$ and DEAD in THF. The nitrile is then transformed to the hydroxyamidine according to literature procedures (e.g. E. Meyer, A. C. Joussef, H. Gallardo, *Synthesis* 2003, 899-905); LC-MS: $t_R$=0.67 min; [M+H]$^+$=295.06; $^1$H NMR (CDCl$_3$): δ 1.32 (s, 3H), 1.36 (s, 3H), 2.27 (s, 6H), 3.75-3.85 (m, 2H), 3.89 (m, 1H), 4.10 (m, 1H), 4.41 (m, 1H), 7.54 (s, 2H).

4-Bromo-2-ethyl-6-methyl-aniline

The title compound is prepared from commercially available 2-ethyl-6-methyl-aniline following literature procedures (R. A. Benkeser, R. A. Hickner, D. I. Hoke, O. H. Thomas *J. Am. Chem. Soc.* 80 (1958) 5289-5293); $^1$H NMR (CDCl$_3$): δ 1.27 (t, J=7.3 Hz, 3H), 2.18 (s, 3H), 2.51 (q, J=7.3 Hz, 2H), 3.61 (s br, 2H), 7.09 (s, 2H).

4-Amino-3-ethyl-5-methyl-benzonitrile

The title compound is prepared from 4-bromo-2-ethyl-6-methyl-aniline following literature procedures (J. Zanon, A. Klapars, S. Buchwald *J. Am. Chem. Soc.* 125 (2003) 2890-2891); $^1$H NMR (CDCl$_3$): δ 1.29 (t, J=7.5 Hz, 3H), 2.19 (s, 3H), 2.52 (q, J=7.5 Hz, 2H), 4.10 (s br, 2H), 7.25 (s br, 2H).

4-Bromo-3-ethyl-5-methyl-benzonitrile

The title compound is prepared from 4-amino-3-ethyl-5-methyl-benzonitrile and copper(II) bromide following literature procedures (M. P. Doyle, B. Siegfried, J. F. Dellaria Jr., *J. Org. Chem.* 42 (1977) 2426-2429); $^1$H NMR (CDCl$_3$): δ 1.26 (t, J=7.5 Hz, 3H), 2.47 (s, 3H), 2.83 (q, J=7.5 Hz, 2H), 7.36 (s, 1H), 7.37 (s, 1H).

3-(4-Cyano-2-ethyl-6-methyl-phenyl)-propionic acid ethyl ester

The title compound is prepared from 4-bromo-3-ethyl-5-methyl-benzonitrile and commercially available acrolein diethyl acetal following literature procedures (G. Battistuzzi, S. Cacchi, G. Fabrizi, R. Bernini, *Synlett* 8 (2003) 1133-1136); LC-MS: $t_R$=0.91 min; $^1$H NMR (CDCl$_3$): δ 1.2 (m, 6H), 2.38 (s, 3H), 2.44 (m, 2H), 2.70 (q, J=7.5 Hz, 2H), 3.03 (m, 2H), 4.18 (q, J=7.3 Hz, 2H), 7.30 (s, 1H), 7.34 (s, 1H).

3-[2-Ethyl-4-(N-hydroxycarbamimidoyl)-6-methyl-phenyl]-propionic acid ethyl ester 3-(4-Cyano-2-ethyl-6-methyl-phenyl)-propionic acid ethyl ester is transformed to the corresponding hydroxyamidine according to literature procedures using triethylamine as base (e.g. E. Meyer, A. C. Joussef, H. Gallardo, *Synthesis* 2003, 899-905); LC-MS: $t_R$=0.77 min; [M+H]$^+$=279.52; $^1$H NMR (D$_6$-DMSO): δ 1.19 (m, 6H), 2.29 (s, 3H), 2.41 (m, 2H), 2.62 (q, J=7.5 Hz, 2H), 2.88 (m, 2H), 4.09 (q, J=7.0 Hz, 2H), 5.68 (s br, 2H), 7.31 (s, 1H), 7.33 (s, 1H), 9.47 (s, 1H).

4-Hydroxy-3-methoxy-5-methyl-benzonitrile

The title compound is prepared from commercially available 2-hydroxy-3-methoxy-toluene in analogy to literature procedures (see 3-ethyl-4-hydroxy-5-methyl-benzonitrile); LC-MS: $t_R$=0.84 min. $^1$H NMR (CDCl$_3$): δ 2.27 (s, 3H), 3.93 (s, 3H), 6.24 (s, 1H), 6.97 (d, J=1.3 Hz, 1H), 7.12 (s, 1H).

3-Chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile); LC-MS: $t_R$=0.85 min. $^1$H NMR (CDCl$_3$): δ2.33 (s, 3H), 6.10 (s, 1H), 7.38 (s, 1H), 7.53 (d, J=1.8 Hz, 1H).

4-Hydroxy-2-methoxy-benzonitrile

The title compound is prepared from commercially available 4-hydroxy-2-methoxy-benzaldehyde in analogy to literature procedures (see 3-ethyl-4-hydroxy-5-methyl-benzonitrile); LC-MS: $t_R$=0.74 min. $^1$H NMR (D$_6$-DMSO): δ 3.84 (s, 3H), 6.47 (d, J=8.5 Hz, 1H), 6.54 (s, 1H), 7.49 (d, J=8.5 Hz, 1H), 10.6 (s, 1H).

4-Hydroxy-2-methyl-benzonitrile

A solution of 4-methoxy-2-methylbenzonitrile (5.0 g, 33.97 mmol) in DCM (150 mL) is cooled down to 0° C. before adding dropwise a 1M BBr$_3$ in DCM solution (136 mL, 136 mmol). The reaction mixture is allowed to reach rt and stirring is then continued at 45° C. for 5 days. Ice water (500 mL) is then added and the reaction mixture is stirred for 1 h before sat. aq. NaHCO$_3$ (250 mL) is added. The mixture is extracted with DCM (200 mL then 4×100 mL) and the combined org. extracts are dried over MgSO$_4$, filtered and evaporated to give the title compound as a brown solid (4.7 g); LC-MS: $t_R$=0.76 min. $^1$H NMR (D$_6$-DMSO): δ 2.38 (s, 3H), 6.73 (dd, J=8.5, 2.0 Hz, 1H), 6.79 (d, J=2.0 Hz, 1H), 7.55 (d, J=8.5 Hz, 1H), 10.49 (s, 1H).

N—((R)-3-[2-Ethyl-4-(N-hydroxycarbamimidoyl)-6-methyl-phenoxy]-2-hydroxy-propyl)-2-hydroxy-acetamide The title compound is obtained as a yellow oil (1.36 g) in analogy to N—((S)-3-[2-ethyl-4-(N-hydroxycarbamimidoyl)-6-methyl-phenoxy]-2-hydroxy-propyl)-2-hydroxy-acetamide starting from 3-ethyl-4-hydroxy-5-methyl-benzonitrile and (S)-glycidol; LC-MS: $t_R$=0.51 min, [M+H]$^+$=326.00.

(S)-2-Hydroxy-N-{2-hydroxy-3-[4-(N-hydroxycarbamimidoyl)-2,6-dimethyl-phenoxy]-propyl}-acetamide The title compound is obtained as a white solid (0.90 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3,5-methyl-benzonitrile and (R)-glycidol; LC-MS: $t_R$=0.47 min, [M+H]$^+$=311.98.

(R)-2-Hydroxy-N-{2-hydroxy-3-[4-(N-hydroxycarbamimidoyl)-2,6-dimethyl-phenoxy]-propyl}-acetamide The title compound is obtained as a yellow oil (0.60 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3,5-methyl-benzonitrile and (S)-glycidol; LC-MS: $t_R$=0.47 min, [M+H]$^+$=311.99.

(S)-2-Hydroxy-N-(2-hydroxy-3-[4-(N-hydroxycarbamimidoyl)-2-methoxy-6-methyl-phenoxy]-propyl)-acetamide The title compound is obtained as a reddish oil (1.3 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3-methoxy-5-methyl-benzonitrile; LC-MS: $t_R$=0.49 min, [M+H]$^+$=327.98.

(S)—N—(-3-[2-Chloro-4-(N-hydroxycarbamimidoyl)-6-methyl-phenoxy]-2-hydroxy-propyl)-2-hydroxy-acetamide The title compound is obtained as a beige wax (1.1 g) in analogy to N—((S)-3-[2-ethyl-4-(N-hydroxycarbamimidoyl)-6-methyl-phenoxy]-2-hydroxy-propyl)-2-hydroxy-acetamide starting from 3-chloro-4-hydroxy-5-methyl-benzonitrile; LC-MS: $t_R$=0.48 min, [M+H]$^+$=331.94.

(S)-2-Hydroxy-N-(2-hydroxy-3-[4-(N-hydroxycarbamimidoyl)-3-methoxy-phenoxy]-propyl)-acetamide The title compound is obtained as a beige wax (0.52 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-2-methoxy-benzonitrile; LC-MS: $t_R$=0.45 min, [M+H]$^+$=313.91.

(S)-2-Hydroxy-N-(2-hydroxy-3-[4-(N-hydroxycarbamimidoyl)-3-methyl-phenoxy]-propyl)-acetamide The title compound is obtained as a beige oil (1.0 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-2-methyl-benzonitrile; LC-MS: $t_R$=0.35 min, [M+H]$^+$=297.99.

(R)-4-(2,2-Dimethyl-[1,3]dioxolan-4-ylmethoxy)-N-hydroxy-3,5-dimethyl-benzamidine The title compound is obtained as a white solid (0.81 g) in analogy to rac-4-(2,2-dimethyl-[1,3]dioxolan-4-ylmethoxy)-

N-hydroxy-3,5-dimethyl-benzamidine using L-alpha-beta-isopropylidene glycerol; LC-MS: $t_R$=0.66 min, $[M+H]^+$=295.00.

(R)-4-(2,2-Dimethyl-[1,3]dioxolan-4-ylmethoxy)-N-hydroxy-3,5-dimethyl-benzamidine The title compound is obtained as a yellow foam (0.34 g) in analogy to rac-4-(2,2-dimethyl-[1,3]dioxolan-4-ylmethoxy)-N-hydroxy-3,5-dimethyl-benzamidine using D-alpha-beta-isopropyliden glycerol; LC-MS: $t_R$=0.67 min, $[M+H]^+$=295.01.

(R)-4-(2,2-Dimethyl-[1,3]dioxolan-4-ylmethoxy)-3-ethyl-N-hydroxy-5-methyl-benzamidine The title compound is obtained as a beige oil (0.86 g) in analogy to rac-4-(2,2-dimethyl-[1,3]dioxolan-4-ylmethoxy)-N-hydroxy-3,5-dimethyl-benzamidine starting from 3-ethyl-4-hydroxy-5-methyl-benzonitrile and L-alpha-beta-isopropyliden glycerol; LC-MS: $t_R$=0.67 min, $[M+H]^+$=308.99.

(S)-4-(2,2-Dimethyl-[1,3]dioxolan-4-ylmethoxy)-3-ethyl-N-hydroxy-5-methyl-benzamidine The title compound is obtained as a yellow oil (0.77 g) in analogy to rac-4-(2,2-dimethyl-[1,3]dioxolan-4-ylmethoxy)-N-hydroxy-3,5-dimethyl-benzamidine starting from 3-ethyl-4-hydroxy-5-methyl-benzonitrile and D-alpha-beta-isopropyliden glycerol; LC-MS: $t_R$=0.68 min, $[M+H]^+$=308.99.

(R)-3-Chloro-4-(2,2-dimethyl-[1,3]dioxolan-4-ylmethoxy)-N-hydroxy-5-methyl-benzamidine The title compound is obtained as a colorless oil (1.39 g) in analogy to rac-4-(2,2-dimethyl-[1,3]dioxolan-4-ylmethoxy)-N-hydroxy-3,5-dimethyl-benzamidine starting from 3-chloro-4-hydroxy-5-methyl-benzonitrile and L-alpha-beta-isopropyliden glycerol; LC-MS: $t_R$=0.66 min, $[M+H]^+$=314.96.

(R)-4-(2,2-Dimethyl-[1,3]dioxolan-4-ylmethoxy)-N-hydroxy-3-methoxy-5-methyl-benzamidine The title compound is obtained as a beige oil (1.16 g) in analogy to rac-4-(2,2-dimethyl-[1,3]dioxolan-4-ylmethoxy)-N-hydroxy-3,5-dimethyl-benzamidine starting from 4-hydroxy-3-methoxy-5-methyl-benzonitrile and L-alpha-beta-isopropyliden glycerol; LC-MS: $t_R$=0.65 min, $[M+H]^+$=311.0.

(R)-4-(2,2-Dimethyl-[1,3]dioxolan-4-ylmethoxy)-N-hydroxy-2-methoxy-benzamidine The title compound is obtained as a beige oil (2.46 g) in analogy to rac-4-(2,2-dimethyl-[1,3]dioxolan-4-ylmethoxy)-N-hydroxy-3,5-dimethyl-benzamidine starting from 4-hydroxy-2-methoxy-benzonitrile and L-alpha-beta-isopropyliden glycerol; LC-MS: $t_R$=0.62 min, $[M+H]^+$=296.97.

(R)-4-(2,2-Dimethyl-[1,3]dioxolan-4-ylmethoxy)-N-hydroxy-2-methyl-benzamidine The title compound is obtained as a beige oil (0.65 g) in analogy to rac-4-(2,2-dimethyl-[1,3]dioxolan-4-ylmethoxy)-N-hydroxy-3,5-dimethyl-benzamidine starting from 4-hydroxy-2-methyl-benzonitrile and L-alpha-beta-isopropyliden glycerol; LC-MS: $t_R$=0.62 min, $[M+H]^+$=281.0.

4-Benzyloxy-3-ethyl-N-hydroxy-5-methyl-benzamidine a) 3-Ethyl-4-hydroxy-5-methyl-benzonitrile (6.0 g, 37 mmol) is dissolved in acetonitrile (80 mL) and $K_2CO_3$ (10.1 g, 73 mmol) and benzyl bromide (6.56 g, 38 mmol) are added. The resulting suspension is stirred at 60° C. for 18 h, then water is added (100 mL) and the org. phase is collected. The aq. phase is extracted with EtOAc (100 mL) and the combined org. extracts are washed with water followed by brine, dried over $MgSO_4$, filtered, evaporated and purified by CC (eluting with Heptane/EtOAc 9:1) to give 4-benzyloxy-3-ethyl-5-methyl-benzonitrile as a yellow oil (7.02 g); LC-MS: $t_R$=1.11 min, $[M+H]^+$=293.16.

b) To a solution of the above benzonitrile intermediate (540 mg, 2.15 mmol) in MeOH (120 mL), hydroxylamine hydrochloride (448 mg, 6.45 mmol) and $NaHCO_3$ (632 mg, 7.52 mmol) are added. The reaction mixture is stirred at 60° C. for 18 h and then then cooled down to rt prior to filtration. The filtrate is evaporated and dissolved in DCM, washed with water followed by brine, dried over $MgSO_4$, filtered and evaporated to give the title compound (420 mg) as a yellow oil; LC-MS: $t_R$=0.79 min, $[M+H]^+$=285.14.

4-Benzyloxy-3-ethyl-5-methyl-benzoic acid hydrazide

To a solution of 4-benzyloxy-3-ethyl-3-methyl-benzoic acid (8.3 g, 30.7 mmol) in DCM (300 mL) is added DIPEA (10.7 mL) and the mixture is cooled to 0° C. before PyBOP (14.5 g, 33.8 mmol) is added. After 10 min, a solution of 1M hydrazine in THF (100 mL) is added dropwise and the mixture is slowly warmed to rt during 2 h. The reaction mixture is then washed with sat. aq. $NaHCO_3$ followed by brine. The org. phase is collected, dried over $MgSO_4$, filtered and evaporated to give the title compound (24 g, 40% purity) as a yellow wax; LC-MS: $t_R$=0.82 min; $[M+H]^+$=285.10.

N-Hydroxy-4-vinyl-benzamidine

4-Cyanostyrene is transformed to the corresponding hydroxyamidine according to literature procedures using hydroxylamine hydrochloride and $NaHCO_3$ as base (e.g. E. Meyer, A. C. Joussef, H. Gallardo, *Synthesis* 2003, 899-905); LC-MS: $t_R$=0.55 min; $[M+H]^+$=163.04; $^1$H NMR ($D_4$-methanol): δ 4.86 (s br, 3H), 5.30 (d, J=11.0 Hz, 1H), 5.85 (d, J=17.6 Hz, 1H), 6.77 (dd, J=17.6, 10.8 Hz, 1H), 7.48 (d, J=8.3 Hz, 2H), 7.63 (d, J=8.0 Hz, 2H).

4-Allyl-N-hydroxy-benzamidine

The title compound is obtained in analogy to N-hydroxy-4-vinyl-benzamidine starting from 3-(4-cyanophenyl)-1-propene; LC-MS: $t_R$=0.59 min, $[M+H]^+$=177.03.

N-Hydroxy-4-(2-hydroxy-ethyl)-benzamidine

The title compound is obtained in analogy to N-hydroxy-4-vinyl-benzamidine starting from 4-(2-hydroxyethyl)-benzonitrile; LC-MS: $t_R$=0.51 min, $[M+H]^+$=181.27.

[4-(N-Hydroxycarbamimidoyl)-phenyl]-acetic acid methyl ester

The title compound is obtained in analogy to N-hydroxy-4-vinyl-benzamidine starting from methyl-4-(cyanophenyl) acetate; LC-MS: $t_R$=0.59 min, $[M+H]^+$=209.07.

2,2-Dimethyl-[1,3]dioxan-5-yl)-methanol

The title compound is prepared following the procedure given in B. Xu, A. Stephens, G. Kirschenheuter, A. F. Crealin, X. Cheng, J. Sennelo, M: Cattaneo, M. L. Zighetti, A. Chen, S.-A. Kim, H. S. Kim, N. Bischofberger, G. Cook, K. A. Jacobson, *J. Med. Chem.* 45 (2002), 5694-5709.

4-(2,2-Dimethyl-[1,3]dioxan-5-ylmethoxy)-3-ethyl-N-hydroxy-5-methyl-benzamidine The title compound is prepared in analog to 4-(2,2-dim-ethyl-[1,3]dioxolan-4-ylmethoxy)-N-hydroxy-3,5-dim-ethyl-benzamidine by O-alkylating 3-ethyl-4-hydroxy-5-methyl-benzonitrile with 2,2-dimethyl-[1,3]dioxan-5-yl)-methanol under Mitsunobu conditions; LC-MS: $t_R$=0.71 min; [M+H]$^+$=323.03.

N-Hydroxy-2-isopropylamino-6-methyl-pyrimidine-4-carboxamidine a) To a solution of 2-isopropylamino-6-methyl-pyrimidine-4-carboxylic acid (1.27 g, 6.53 mmol) in ethanol (20 mL), concentrated H$_2$SO$_4$ (4 mL) is added. The reaction mixture is stirred at 80° C. for 18 h and is then evaporated. The residue is dissolved in EtOAc, washed with sat. aq. NaHCO$_3$ and water, dried over MgSO$_4$, filtered and evaporated. The crude compound is purified by CC on silica gel (eluting with Heptane/EtOAc 4:1) to give 2-isopropylamino-6-methyl-pyrimidine-4-carboxylic acid ethyl ester as a yellow oil (1.46 g); LC-MS: $t_R$=0.97; [M+H]$^+$=224.49.

b) A solution of 2-isopropylamino-6-methyl-pyrimidine-4-carboxylic acid ethyl ester (1.46 g, 6.54 mmol) in 3M NH$_3$ in MeOH (50 mL) is stirred at 60° C. for 1 day. Volatiles are evaporated to give the crude 2-isopropylamino-6-methyl-pyrimidine-4-carboxylic acid amide as a pale yellow solid (1.24 g); LC-MS: $t_R$=0.59; [M+H]$^+$=195.0.

c) To a suspension of 2-isopropylamino-6-methyl-pyrimidine-4-carboxylic acid amide (1.24 g, 6.4 mmol) in DCM (20 mL), pyridine (2.53 mL, 25.6 mmol) is added followed by TFFA (2.7 mL, 19.2 mmol). The reaction mixture is stirred for 4 h, and then is quenched with water. The mixture is extracted with DCM. The org. phase is washed with sat. aq. NaHCO$_3$ and dried over MgSO$_4$, filtered and evaporated. Purification by CC on silica gel (eluting with Heptane/EtOAc 4:1) affords the 2-isopropylamino-6-methyl-pyrimidine-4-carbonitrile as a yellow oil (2.81 g); LC-MS: $t_R$=0.89; [M+H]$^+$=177.04.

d) 2-Isopropylamino-6-methyl-pyrimidine-4-carbonitrile (2.8 g, 16.0 mmol) is added to a suspension of NaHCO$_3$ (4.71 g, 56.1 mmol) and hydroxylamine hydrochloride (3.34 g, 48.1 mmol) in MeOH (20 mL). The reaction mixture is stirred at rt for 1 day and is filtered and evaporated. The residue is dissolved in DCM, washed with water followed by brine and dried to give N-hydroxy-2-isopropylamino-6-methyl-pyrimidine-4-carboxamidine as a yellow oil (1.38 g); LC-MS: $t_R$=0.55; [M+H]$^+$=209.96.

2-Ethyl-4-[5-(2-isopropylamino-6-methyl-pyrimidin-4-yl)-[1,3,4]oxadiazol-2-yl]-6-methyl-phenol (Intermediate 1)

a) To a solution of 2-isopropylamino-6-methyl-pyrimidine-4-carboxylic acid (200 mg, 1.02 mmol) and DIPEA (0.43 mL) in DMF (100 mL) is added TBTU (395 mg, 1.23 mmol). The reaction mixture is stirred at 0° C. for 15 min before adding 4-benzyloxy-3-ethyl-5-methyl-benzoic acid hydrazide. Stirring is continued for 1 h and the reaction mixture is then diluted with EtOAc and washed with sat. aq. NaHCO$_3$. The aq. phase is extracted with EtOAc and the combined org. phases are dried over MgSO$_4$, filtered and evaporated to give a brown oil. The oil is dissolved in THF (5.0 mL) and Burgess reagent (155 mg, 0.65 mmol) is added. The reaction mixture is heated to 110° C. for 15 min under microwave conditions. The reaction mixture is evaporated and purified by prep. TLC (eluting with Heptane/EA 9:1) to afford {4-[5-(4-benzyloxy-3-ethyl-5-methyl-phenyl)-[1,3,4]oxadiazol-2-yl]-6-methyl-pyrimidin-2-yl}-isopropyl-amine as a yellow oil (125 mg, 56%); LC-MS: $t_R$=1.16; [M+H]$^+$=444.08.

b) The above benzyloxy derivative (360 mg, 0.813 mmol) is dissolved in EtOAc (3.0 mL) and a solution of 33% HBr in AcOH (1 mL) is added. The reaction mixture is stirred at rt for 18 h, and is then diluted with EtOAc and neutralized with sat. aq. NaHCO$_3$. The org. phase is collected and washed with sat. aq. NaHCO$_3$ again, dried over MgSO$_4$, filtered and evaporated to give a residue that is purified by prep. HPLC to give the title compound (140 mg) as a beige solid; LC-MS: $t_R$=1.00; [M+H]$^+$=354.42.

2-Ethyl-4-[5-(2-isobutylamino-6-methyl-pyrimidin-4-yl)-[1,3,4]oxadiazol-2-yl]-6-methyl-phenol (Intermediate 2)

The title compound is obtained in analogy to 2-ethyl-4-[5-(2-isopropylamino-6-methyl-pyrimidin-4-yl)-[1,3,4]oxadiazol-2-yl]-6-methyl-phenol starting from 2-isobutylamino-6-methyl-pyrimidine-4-carboxylic acid; LC-MS: $t_R$=1.05 min, [M+H]$^+$=368.24.

2-Ethyl-4-[5-(2-isopropoxy-6-methyl-pyrimidin-4-yl)-[1,3,4]oxadiazol-2-yl]-6-methyl-phenol (Intermediate 3)

The title compound is obtained in analogy to 2-ethyl-4-[5-(2-isopropylamino-6-methyl-pyrimidin-4-yl)-[1,3,4]oxadiazol-2-yl]-6-methyl-phenol starting from 2-isopropoxy-6-methyl-pyrimidine-4-carboxylic acid; LC-MS: $t_R$=1.03 min, [M+H]$^+$=355.05.

2-Ethyl-4-[5-(2-isobutoxy-6-methyl-pyrimidin-4-yl)-[1,3,4]oxadiazol-2-yl]-6-methyl-phenol (Intermediate 4)

The title compound is obtained in analogy to 2-ethyl-4-[5-(2-isopropylamino-6-methyl-pyrimidin-4-yl)-[1,3,4]oxadiazol-2-yl]-6-methyl-phenol starting from 2-isobutoxy-6-methyl-pyrimidine-4-carboxylic acid; LC-MS: $t_R$=1.08 min, [M+H]$^+$=369.08.

2-Ethyl-4-[5-(2-isopropylamino-6-methyl-pyrimidin-4-yl)-[1,3,4]thiadiazol-2-yl]-6-methyl-phenol (Intermediate 5)

The title compound is obtained in analogy to 2-ethyl-4-[5-(2-isopropylamino-6-methyl-pyrimidin-4-yl)-[1,3,4]oxadiazol-2-yl]-6-methyl-phenol (Intermediate 1) using the Lawesson reagent (1.3 eq.) in place of the Burgess reagent for the cyclization under microwave conditions (30 min, 110° C.); LC-MS: $t_R$=1.03 min, [M+H]$^+$=370.31.

2-Ethyl-4-[5-(2-isobutylamino-6-methyl-pyrimidin-4-yl)-[1,3,4]thiadiazol-2-yl]-6-methyl-phenol (Intermediate 6)

The title compound is obtained in analogy to 2-ethyl-4-[5-(2-isopropylamino-6-methyl-pyrimidin-4-yl)-[1,3,4]thiadiazol-2-yl]-6-methyl-phenol (Intermediate 5) starting from 2-isobutylamino-6-methyl-pyrimidine-4-carboxylic acid; LC-MS: $t_R$=1.06 min, [M+H]$^+$=383.85.

2-Ethyl-4-[5-(2-isobutoxy-6-methyl-pyrimidin-4-yl)-[1,3,4]thiadiazol-2-yl]-6-methyl-phenol (Intermediate 7)

The title compound is obtained in analogy to 2-ethyl-4-[5-(2-isopropylamino-6-methyl-pyrimidin-4-yl)-[1,3,4]thiadiazol-2-yl]-6-methyl-phenol (Intermediate 5) starting from 2-isobutoxy-6-methyl-pyrimidine-4-carboxylic acid; LC-MS: $t_R$=1.14 min, [M+H]$^+$=385.00.

Isopropyl-{4-methyl-6-[3-(4-vinyl-phenyl)-[1,2,4]oxadiazol-5-yl]-pyrimidin-2-yl}-amine (Intermediate 8)

To a suspension of 2-isopropylamino-6-methyl-pyrimidine-4-carboxylic acid (1.9 g, 11.8 mmol) in DMF (25 mL) is added HOBt (1.8 g, 13.4 mmol) followed by EDC (2.6 g, 13.4 mmol). The reaction mixture is stirred for 40 min until a clear solution is obtained and a solution of N-hydroxy-4-vinyl-benzamidine (2.09 g, 10.7 mmol) in DMF (20 mL) is added. After 2 h, EtOAc (320 mL) is added to the reaction mixture and the solution is then washed with sat. aq. NaHCO$_3$ (3×100 mL), with brine, dried over MgSO$_4$, filtered and evaporated to give a red oil. The oil is dissolved in dioxane (50 mL) and the solution is heated to 95° C. for 2 h. The reaction mixture is evaporated and purification by CC on silica gel affords the title compound as a yellow oil (2.79 g); LC-MS: $t_R$=1.12; [M+H]$^+$=321.95.

{4-[3-(4-Allyl-phenyl)-[1,2,4]oxadiazol-5-yl]-6-methyl-pyrimidin-2-yl}-isopropyl-amine (Intermediate 9)

The title compound is obtained in analogy to isopropyl-{4-methyl-6-[3-(4-vinyl-phenyl)-[1,2,4]oxadiazol-5-yl]-pyrimidin-2-yl}-amine starting from 4-allyl-N-hydroxy-benzamidine; LC-MS: $t_R$=1.14 min, [M+H]$^+$=336.04.

3-{2-Ethyl-4-[5-(2-isopropylamino-6-methyl-pyrimidin-4-yl)-[1,2,4]oxadiazol-3-yl]-6-methyl-phenyl}-propionic acid hydrochloride (Intermediate 10)

a) 2-Isopropylamino-6-methyl-pyrimidine-4-carboxylic acid (500 mg, 2.56 mmol) dissolved in DMF (10 mL) is coupled to 3-[2-ethyl-4-(N-hydroxycarbamimidoyl)-6-methyl-phenyl]-propionic acid ethyl ester (786 mg, 2.79 mmol) under standard conditions using EDC (1.5 eq.), HOBt (1.5 eq.) and DIPEA (2.0 eq.) to give the hydroxyamidine ester intermediate. This material is dissolved in dioxane (20 mL) and the resulting solution is stirred at 85° C. for 18 h. The solvent is removed in vacuo and the crude product is purified by CC on silica gel to give the desired 3-{2-ethyl-4-[5-(2-isopropylamino-6-methyl-pyrimidin-4-yl)[1,2,4]oxadiazol-3-yl]-6-methyl-phenyl}-propionic acid ethyl ester (0.87 g).

b) The above ethyl ester is hydrolyzed with 6N aq. HCl (69 mL) to give 3-{2-ethyl-4-[5-(2-isopropylamino-6-methyl-pyrimidin-4-yl)-[1,2,4]oxadiazol-3-yl]-6-methyl-phenyl}-propionic acid hydrochloride as a yellow powder (825 mg); LC-MS: $t_R$=1.05 min; [M+H]$^+$=410.02.

4-[5-(2-Diethylamino-6-methyl-pyrimidin-4-yl)-[1,2,4]oxadiazol-3-yl]-2-ethyl-6-methyl-phenol (Intermediate 11)

a) To a solution of 2-diethylamino-6-methyl-pyrimidine-4-carboxylic acid (5.56 g, 27.0 mmol mmol) and 4-benzyloxy-3-ethyl-N-hydroxy-5-methyl-benzamidine (7.69 g, 27 mmol) in DMF (80 mL), EDC (6.74 g, 35.2 mmol) and HOBt (4.75 g, 35.2 mmol) are added at 0° C. Stirring is continued at rt for 2 h and the reaction mixture is then diluted with EtOAc and washed with sat. aq. NaHCO$_3$. The aq. phase is extracted with EtOAc and the combined org. extracts are dried over MgSO$_4$, filtered and evaporated to give a brown oil. The oil is dissolved in dioxane (30 mL) and the solution is heated to 85° C. for 18 h. The reaction mixture is evaporated and purified by CC (eluting with Heptane/EA 9:1) to afford {4-[3-(4-benzyloxy-3-ethyl-5-methyl-phenyl)-[1,2,4]oxadiazol-5-yl]-6-methyl-pyrimidin-2-yl}-diethyl-amine as a yellow oil (4.3 g, 35%); LC-MS: $t_R$=1.35; [M+H]$^+$=458.48.

b) The above benzyloxy derivative (4.3 g, 9.4 mmol) is dissolved in THF (300 mL) and Pd/C (600 mg) is added followed by AcOH (5 mL). The reaction mixture is stirred for 1 h under H$_2$ atmosphere, then filtered and evaporated. The residue is purified by CC (eluting with Heptane/EtOAc 9:1) to give the title compound (2.61 g) as a yellow crystalline solid; LC-MS: $t_R$=1.17; [M+H]$^+$=368.10. $^1$H NMR (D$_6$-DMSO) δ 1.19 (m, 9H), 2.28 (s, 3H), 2.44 (s, 3H), 2.68 (q, J=7.5 Hz, 2H), 3.67 (q, J=7.0 Hz, 4H), 7.29 (s, 1H), 7.68 (s, 2H), 8.96 (s br, 1H).

(S)-Diethyl-{4-[3-(3-ethyl-5-methyl-4-oxiranylmethoxy-phenyl)-[1,2,4]oxadiazol-5-yl]-6-methyl-pyrimidin-2-yl}-amine (Intermediate 12)

To a solution of 4-[5-(2-diethylamino-6-methyl-pyrimidin-4-yl)-[1,2,4]oxadiazol-3-yl]-2-ethyl-6-methyl-phenol (700 mg, 1.90 mmol) in isopropanol (12 mL), are added 3M aq. NaOH (4 mL) and R-epichlorohydrine (1.49 mL, 19.0 mmol). The reaction mixture is stirred at rt for 15 h, then is diluted with EtOAc and washed with 1M aq. NaOH followed by brine. The org. phase is dried over Na$_2$SO$_4$, filtered, evaporated and purified by CC (eluting with Heptane/EtOAc 4:1) to give the title compound as a yellow oil (882 mg); LC-MS: $t_R$=1.23; [M+H]$^+$=424.04. $^1$H NMR (CDCl$_3$) δ 1.25 (t, J=7.0 Hz, 6H), 1.33 (t, J=7.5 Hz, 3H), 2.41 (s, 3H), 2.47 (s, 3H), 2.79 (m, 3H), 2.94 (t, J=4.5 Hz, 1H), 3.42 (m, 1H), 3.76 (q, J=7.0 Hz, 4H), 3.83 (dd, J=11.0, 5.8 Hz, 1H), 4.13 (dd, J=11.0, 3.0 Hz, 1H), 7.23 (s, 1H), 7.89 (d, J=5.5 Hz, 2H).

2-{4-[5-(2-Diethylamino-6-methyl-pyrimidin-4-yl)-[1,2,4]oxadiazol-3-yl]-phenyl}-ethanol (Intermediate 13)

To a suspension of 2-diethylamino-6-methylpyrimidine-4-carboxylic acid (1.31 g, 6.28 mmol) in DMF (20 mL) is added DIPEA (3.23 mL, 18.8 mmol) followed by TBTU (2.62 g, 8.17 mmol). The mixture is stirred at rt for 10 min before N-hydroxy-4-(2-hydroxy-ethyl)-benzamidine (1.24 g, 6.91 mmol) is added. After stirring for 1 h, the reaction mixture is diluted with EtOAc and the solution is washed with sat. aq. NaHCO$_3$. The aq. phase is extracted with EtOAc and the combined org. extracts are dried over MgSO$_4$, filtered and concentrated to give the crude hydroxyamidine ester intermediate (3.56 g). This material is dissolved in dioxane (50 mL) and the resulting solution is stirred at 85° C. for 16 h. The solvent is evaporated and the crude product is purified by CC (eluting with EtOAc/Heptane 1:4) to give 2-{4-[5-(2-diethylamino-6-methyl-pyrimidin-4-yl)-[1,2,4]oxadiazol-3-yl]-phenyl}-ethanol as a yellow solid (1.30 g); LC-MS: $t_R$=1.07 min; [M+H]$^+$=354.07. $^1$H NMR (CDCl$_3$): δ 1.25 (t, J=7.0 Hz, 6H), 1.45 (m, 1H), 2.47 (s, 3H), 2.98 (t, J=6.5 Hz, 2H), 3.75

(q, J=7.0 Hz, 4H), 3.95 (m, 2H), 7.23 (s, 1H), 7.41 (d, J=7.8 Hz, 2H), 8.15 (d, J=7.5 Hz, 2H).

(4-{3-[4-(2-Amino-ethyl)-phenyl]-[1,2,4]oxadiazol-5-yl}-6-methyl-pyrimidin-2-yl)-diethyl-amine (Intermediate 14)

a) To a solution of 2-{4-[5-(2-diethylamino-6-methyl-pyrimidin-4-yl)-[1,2,4]oxadiazol-3-yl]-phenyl}-ethanol (1.2 g, 3.40 mmol) in DCM (20 mL) is added DIPEA (5.09 mmol) followed by methanesulfonylchloride (466 mg, 4.07 mmol). The reaction mixture is stirred for 1 h, then diluted with EtOAc and washed with sat. aq. NaHCO$_3$. The aq. phase is extracted with EtOAc and the combined org. phases are dried over MgSO$_4$, filtered and evaporated to give the mesylate intermediate as a light brown solid (1.46 g); LC-MS: $t_R$=1.13 min; [M+H]$^+$=432.00.

b) The mesylate intermediate (1.46 g, 3.40 mmol) is dissolved in DMF (10 mL) and NaN$_3$ is added (1.13 g, 16.97 mmol). The reaction mixture is stirred at rt for 24 h and is then diluted with EtOAc and washed with water and brine. The org. phase is dried over MgSO$_4$, filtered and evaporated to give the azide intermediate as a yellow oil (1.45 g); LC-MS: $t_R$=1.20 min; [M+H]$^+$=379.07.

c) Triphenylphosphine (1.33 g, 5.09 mmol) is added to a solution of the azide derivative (1.28 g) in THF (30 mL). The reaction mixture is stirred at rt for 4 days, is then evaporated and the residue is purified by prep. HLPC to give (4-{3-[4-(2-amino-ethyl)-phenyl]-[1,2,4]oxadiazol-5-yl}-6-methyl-pyrimidin-2-yl)-diethyl-amine as a yellow oil (435 mg); LC-MS: $t_R$=0.80 min; [M+H]$^+$=353.1. $^1$H NMR (CDCl$_3$) δ 1.25 (t, J=7.0 Hz, 6H), 2.88 (t, J=6.8 Hz, 2H), 3.07 (t, J=7.0 Hz, 2H), 3.75 (q, J=7.0 Hz, 4H), 7.22 (s, 1H), 7.37 (d, J=8.3 Hz, 2H), 8.13 (d, J=8.3 Hz, 2H).

{4-[5-(2-Diethylamino-6-methyl-pyrimidin-4-yl)-[1,2,4]oxadiazol-3-yl]-phenyl}-acetic acid (Intermediate 15)

The title compound is obtained in analogy to 3-{2-ethyl-4-[5-(2-isopropylamino-6-methyl-pyrimidin-4-yl)-[1,2,4]oxadiazol-3-yl]-6-methyl-phenyl}-propionic acid hydrochloride (Intermediate 10) starting from 2-diethylamino-6-methyl-pyrimidine-4-carboxylic acid and [4-(N-hydroxycarbamimidoyl)-phenyl]-acetic acid ethyl ester; LC-MS: $t_R$=1.05 min, [M+H]$^+$=368.04.

Example 1

N—((S)-3-{2-Ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide To a solution of 2-ethylamino-6-methyl-pyrimidine-4-carboxylic acid (40 mg, 0.221 mmol) in DMF (3.0 mL), HOBt (36 mg, 0.266 mmol) and EDC.HCl (47 mg, 0.243 mmol) are added.

The reaction mixture is stirred for 5 min before adding (S)—N-(3-[2-ethyl-4-(N-hydroxycarbamimidoyl)-6-methyl-phenoxy]-2-hydroxy-propyl)-2-hydroxy-acetamide (72 mg, 0.221 mmol). The mixture is stirred at rt for 1 h before it is diluted with ethylacetate, washed with sat. aq. NaHCO$_3$ and brine, dried over Na$_2$SO$_4$, filtered and concentrated to give the hydroxyamidine ester intermediate. This material is dissolved in dioxane (3 mL) and the resulting solution is stirred at 85° C. for 16 h. The solvent is evaporated and the crude product is purified by prep. HPLC (X-Bridge) to give N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide (31 mg) as a yellow crystalline solid; LC-MS: $t_R$=0.88 min; [M+H]$^+$=471.30. $^1$H NMR (D$_6$-DMSO): δ 1.16 (t, J=7.3 Hz, 3H), 1.22 (t, J=7.5 Hz, 3H), 2.34 (s, 3 H), 2.41 (s, 3H), 2.73 (q, J=7.5 Hz, 2H), 3.25 (m, 1H), 3.34-3.50 (m, 3H), 3.75 (m, 2H), 3.84 (d, J=5.8 Hz, 2H), 3.96 (m, 1H), 5.31 (d, J=5.8 Hz, 1H), 5.55 (t, J=5.8 Hz, 1H), 7.29 (s, 1H), 7.62 (s br, 1H), 7.69 (t, J=5.8 Hz, 1H), 7.78 (s, 2H).

Example 2

N—((S)-3-{2-Ethyl-4-[5-(2-isobutylamino-6-methyl-pyrimidin-4-yl)-[1,2,4]oxadiazol-3-yl]-6-methyl-phenoxy}-2-hydroxy-propyl)-2-hydroxy-acetamide N—((S)-3-{2-Ethyl-4-[5-(2-isobutylamino-6-methyl-pyrimidin-4-yl)-[1,2,4]oxadiazol-3-yl]-6-methyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-isobutylamino-6-methyl-pyrimidine-4-carboxylic acid; LC-MS: $t_R$=0.96 min; [M+H]$^+$=499.25. $^1$H NMR (D$_6$-DMSO): δ 0.92 (d, J=6.5 Hz, 6H), 1.22 (t, J=7.5 Hz, 3H), 1.91 (m, 1H), 2.35 (s, 3H), 2.41 (s, 3H), 2.73 (q, J=7.5 Hz, 2H), 3.15-3.28 (m, 3H), 3.43 (m, 1H), 3.70-3.80 (m, 2H), 3.84 (d, J=4.8 Hz, 2H), 3.96 (m, 1H), 5.30 (d, J=5.0 Hz, 1H), 5.55 (m, 1H), 7.29 (s, 1H), 7.69 (m, 2H), 7.78 (s, 2H).

Example 3

N—((S)-3-{4-[5-(2-Diethylamino-6-methyl-pyrimidin-4-yl)-[1,2,4]oxadiazol-3-yl]-2-ethyl-6-methyl-phenoxy}-2-hydroxy-propyl)-2-hydroxy-acetamide N((S)-3-{4-[5-(2-Diethylamino-6-methyl-pyrimidin-4-yl)-[1,2,4]oxadiazol-3-yl]-2-ethyl-6-methyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-diethylamino-6-methyl-pyrimidine-4-carboxylic acid; LC-MS: $t_R$=1.03 min; [M+H]$^+$=499.23. $^1$H NMR (D$_6$-DMSO): δ 1.18 (t, J=7.0 Hz, 6H), 1.22 (t, J=7.3 Hz, 3H), 2.35 (s, 3H), 2.44 (s, 3H), 2.73 (q, J=7.3 Hz, 2 H), 3.25 (m, 1H), 3.44 (m, 1H), 3.67 (q, J=7.0 Hz, 4H), 3.76 (m, 2H), 3.84 (d, J=5.8 Hz, 2H), 3.96 (m, 1H), 5.31 (d, J=5.0 Hz, 1H), 5.55 (t, J=5.5 Hz, 1H), 7.30 (s, 1H), 7.69 (t, J=5.5 Hz, 1H), 7.78 (s, 2H).

Example 4 rac-N-(3-{4-[5-(2-Ethylamino-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Ethylamino-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-ethylamino-6-methyl-pyrimidine-4-carboxylic acid and 2-hydroxy-N-{2-hydroxy-3-[4-(N-hydroxycarbamimidoyl)-2,6-dimethyl-phenoxy]-propyl}-acetamide; LC-MS: $t_R$=0.86 min;

[M+H]⁺=457.27. ¹H NMR (D₆-DMSO): δ 1.16 (t, J=7.0 Hz, 3H), 2.34 (s, 6H), 2.41 (s, 3H), 3.25 (m, 1H), 3.35-3.50 (m, 3H), 3.70-3.80 (m, 2H), 3.84 (d, J=5.3 Hz, 2H), 3.96 (m, 1H), 5.29 (d, J=5.0 Hz, 1H), 5.55 (t, J=5.8 Hz, 1H), 7.28 (s, 1H), 7.63 (s br, 1H), 7.69 (t, J=5.3 Hz, 1H), 7.76 (s, 2H).

Example 5 rac-N-(3-{2,6-Dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide rac-N-(3-{2,6-Dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 6-methyl-2-methylamino-pyrimidine-4-carboxylic acid and 2-hydroxy-N-{2-hydroxy-3-[4-(N-hydroxycarbamimidoyl)-2,6-dimethyl-phenoxy]-propyl}-acetamide; LC-MS: $t_R$=0.85 min; [M+H]⁺=443.21.

Example 6 rac-N-(3-{2,6-Dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide rac-N-(3-{2,6-Dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 6-methyl-2-propylamino-pyrimidine-4-carboxylic acid and 2-hydroxy-N-{2-hydroxy-3-[4-(N-hydroxycarbamimidoyl)-2,6-dimethyl-phenoxy]-propyl}-acetamide; LC-MS: $t_R$=0.92 min, [M+H]⁺=471.25.

Example 7 rac-N-(3-{4-[5-(2-Isopropylamino-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Isopropylamino-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-isopropylamino-6-methyl-pyrimidine-4-carboxylic acid and 2-hydroxy-N-{2-hydroxy-3-[4-(N-hydroxycarbamimidoyl)-2,6-dimethyl-phenoxy]-propyl}-acetamide; LC-MS: $t_R$=0.92 min, [M+H]⁺=471.25.

Example 8 rac-N-(3-{4-[5-(2-Isobutylamino-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Isobutylamino-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-isobutylamino-6-methyl-pyrimidine-4-carboxylic acid and 2-hydroxy-N-{2-hydroxy-3-[4-(N-hydroxycarbamimidoyl)-2,6-dimethyl-phenoxy]-propyl}-acetamide; LC-MS: $t_R$=0.96 min; [M+H]⁺=485.31.

Example 9 rac-N-(3-{4-[5-(2-(Ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-(Ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-ethyl-methylamino-6-methyl-pyrimidine-4-carboxylic acid and 2-hydroxy-N-{2-hydroxy-3-[4-(N-hydroxycarbamimidoyl)-2,6-dimethyl-phenoxy}-propyl]-acetamide; LC-MS: $t_R$=0.98 min; [M+H]⁺=471.26.

Example 10 rac-N-(3-{4-[5-(2-Diethylamino-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Diethylamino-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-diethylamino-6-methyl-pyrimidine-4-carboxylic acid and 2-hydroxy-N-{2-hydroxy-3-(N-hydroxycarbamimidoyl)-2,6-dimethyl-phenoxy]-propyl}-acetamide; LC-MS: $t_R$=1.01 min; [M+H]⁺=485.30. ¹H NMR (D₆-DMSO): δ 1.18 (t, J=6.8 Hz, 6H), 2.34 (s, 6H), 2.43 (s, 3H), 3.25 (m, 1H), 3.45 (m, 1H), 3.67 (q, J=6.8 Hz, 4H), 3.70-3.82 (m, 2H), 3.84 (d, J=5.5 Hz, 2H), 3.96 (m, 1H), 5.29 (d, J=5.3 Hz, 1H), 5.55 (t, J=5.5 Hz, 1H), 7.27 (s, 1H), 7.69 (t, J=5.5 Hz, 1H), 7.76 (s, 2H).

Example 11 rac-N-(3-{4-[5-(2-Dimethylamino-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Dimethylamino-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 6-methyl-2-methylamino-pyrimidine-4-carboxylic acid and 2-hydroxy-N-{2-hydroxy-3-(N-hydroxycarbamimidoyl)-2,6-dimethyl-phenoxy]-propyl}-acetamide; LC-MS: $t_R$=0.94 min; [M+H]⁺=457.31.

Example 12 rac-N-(3-{4-[5-(2-Methoxy-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Methoxy-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-methoxy-6-methyl-pyrimidine-4-carboxylic acid and 2-hydroxy-N-{2-hydroxy-3-[4-(N-hydroxycarbamimioyl)-2,6-dimethyl-phenoxy]-propyl}-acetamide; LC-MS: $t_R$=0.84 min; [M+H]$^+$=444.19.

Example 13 rac-N-(3-{4-[5-(2-Ethoxy-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Ethoxy-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-ethoxy)-6-methyl-pyrimidine-4-carboxylic acid and 2-hydroxy-N-{2-hydroxy-3-[4-(N-hydroxycarbamimioyl)-2,6-dimethyl-phenoxy]-propyl}-acetamide; LC-MS: $t_R$=0.92 min; [M+H]$^+$=458.20.

Example 14 rac-N-(3-{4-[5-(6-Methyl-2-propoxy-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(6-Methyl-2-propoxy-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 6-methyl-2-propoxy-pyrimidine-4-carboxylic acid and 2-hydroxy-N-{2-hydroxy-3-[4-(N-hydroxycarbamimioyl)-2,6-dimethyl-phenoxy]-propyl}-acetamide; LC-MS: $t_R$=0.96 min; [M+H]$^+$=472.23.

Example 15 rac-N-(3-{4-[5-(2-Isopropoxy-6-methyl-pyrimidin-4-yl)-[1,2,4]oxadiazol-3-yl]-2,6-dimethyl-phenoxy}-2-hydroxy-propyl)-2-hydroxy-acetamide rac-N-(3-{4-[5-(2-Isopropoxy-6-methyl-pyrimidin-4-yl)-[1,2,4]oxadiazol-3-yl]-2,6-dimethyl-phenoxy}-2-hydroxy-propyl)-2-hydroxy-acetamide is prepared in analogy to N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide using 2-isopropoxy-6-methyl-pyrimidine-4-carboxylic acid and 2-hydroxy-N-{2-hydroxy-3-[4-(N-hydroxycarbamimioyl)-2,6-dimethyl-phenoxy]-propyl}-acetamide; LC-MS: $t_R$=0.95 min; [M+H]$^+$=472.21.

Example 16 rac-3-{4-[5-(2-Ethylamino-6-methyl-pyrimidin-4-yl)-[1,2,4]oxadiazol-3-yl]-2,6-dimethyl-phenoxy}-propane-1,2-diol Method A a) 2-Ethylamino-6-methyl-pyrimidine-4-carboxylic acid and 4-(2,2-dimethyl-[1,3]dioxolan-4-ylmethoxy)-N-hydroxy-3,5-dimethyl-benzamidine are coupled followed by cyclisation in analogy to Example 1 to give (4-{3-[4-(2,2-dimethyl-[1,3]dioxolan-4-ylmethoxy)-3,5-dimethyl-phenyl]-[1,2,4]-oxadiazol-5-yl}-6-methyl-pyrimidin-2-yl)-ethyl-amine; LC-MS: $t_R$=1.12 min; [M+H]$^+$=440.21.

b) The above intermediate is dissolved in acetonitrile/methanol 1:1 before adding 5N HCl in propanol. The mixture is stirred at rt for 1 h, then basified with ammonium hydroxide, concentrated and purified by prep. HPLC (X-Bridge) to give rac-3-{4-[5-(2-ethylamino-6-methyl-pyrimidin-4-yl)-[1,2,4]oxadiazol-3-yl]-2,6-dimethyl-phenoxy}-propane-1,2-diol as a white crystalline solid; LC-MS: $t_R$=0.80 min*; [M+H]$^+$=400.06; $^1$H NMR (D$_6$-DMSO): δ 1.17 (t, J=7.0 Hz, 3H), 2.35 (s, 6H), 2.42 (s, 3H), 3.37 (m, 2H), 3.50 (t, J=5.3 Hz, 2H), 3.75 (dd, J=5.5 and 8.8 Hz, 1H), 3.80-3.90 (m, 2H), 4.64 (t, J=5.3 Hz, 1H), 4.94 (d, J=5.0 Hz, 1H), 7.29 (s, 1H), 7.65 (s br, 1H), 7.76 (s, 2H).

Method B a) To a solution of 2-chloro-6-methylpyrimidine-4-carboxylic acid (293 mg, 1.70 mmol) in DMF (10 mL), HOBt (275 mg, 2.04 mmol) and EDC.HCl (358 mg, 1.87 mmol) are added at 5° C. The reaction mixture is stirred for 5 min before adding 4-(2,2-dimethyl-[1,3]dioxolan-4-ylmethoxy)-N-hydroxy-3,5-dimethyl-benzamidine (500 mg, 1.70 mmol). The mixture is stirred at rt for 1 h before it is diluted with ethylacetate, washed with sat. aq. NaHCO$_3$ and brine, dried over Na$_2$SO$_4$, filtered and concentrated to give the hydroxyamidine ester intermediate. This material is dissolved in dioxane (3 mL) and the resulting solution is stirred at 85° C. for 16 h. The solvent is evaporated and the crude product is purified by prep. HPLC (X-Bridge) to give 2-chloro-4-{3-[4-(2,2-dimethyl-[1,3]dioxolan-4-ylmethoxy)-3,5-dimethyl-phenyl]-[1,2,4]oxadiazol-5-yl}-6-methyl-pyrimidine (93 mg) as a yellow solid.

b) To a solution of the above 2-chloro-6-methyl-pyrimidine intermediate (22 mg, 0.052 mmol) in dioxane (1 mL), ethylamine 70% in water (0.21 mL, 2.61 mmol) and 2M aq. NaOH (0.15 mL) are added. The mixture is stirred at 70° C. for 18 h, then concentrated and purified by prep. HPLC (X-Bridge) to give (4-{3-[4-(2,2-dimethyl-[1,3]dioxolan-4-ylmethoxy)-3,5-dimethyl-phenyl]-[1,2,4]-oxadiazol-5-yl}-6-methyl-pyrimidin-2-yl)-ethyl-amine (16 mg) as a pale yellow solid; LC-MS: $t_R$=1.12 min; [M+H]$^+$=440.21.

c) The above ispropylidenglycerol derivative is hydrolysed as described in Method A b) to give rac-3-{4-[5-(2-ethylamino-6-methyl-pyrimidin-4-yl)-[1,2,4]oxadiazol-3-yl]-2,6-dimethyl-phenoxy}-propane-1,2-diol.

Example 17 rac-3-{2,6-Dimethyl-4-[5-(6-methyl-2-methylamino-pyrimidin-4-yl)-[1,2,4]oxadiazol-3-yl]-phenoxy}-propane-1,2-diol rac-3-{2,6-Dimethyl-4-[5-(6-methyl-2-methylamino-pyrimidin-4-yl)-[1,2,4]oxadiazol-3-yl]-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 6-methyl-2-methylamino-pyrimidine-4-carboxylic acid; LC-MS: $t_R$=0.75 min*; [M+H]$^+$=386.15.

Example 18 rac-3-{2,6-Dimethyl-4-[5-(6-methyl-2-propylamino-pyrimidin-4-yl)-[1,2,4]oxadiazol-3-yl]-phenoxy}-propane-1,2-diol rac-3-{2,6-Dimethyl-4-[5-(6-methyl-2-propylamino-pyrimidin-4-yl)-[1,2,4]oxadiazol-3-yl]-phenoxy}-propane-1, 2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 6-methyl-2-propylamino-pyrimidine-4-carboxylic acid; LC-MS: $t_R$=0.85 min*; [M+H]$^+$=414.15.

Example 19 rac-3-{4-[5-(2-Isopropylamino-6-methyl-pyrimidin-4-yl)-[1,2,4]oxadiazol-3-yl]-2,6-dimethyl-phenoxy}-propane-1,2-diol rac-3-{4-[5-(2-Isopropylamino-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-isopropylamino-6-methyl-pyrimidine-4-carboxylic acid; LC-MS: $t_R$=0.85 min*; [M+H]$^+$=414.12.

Example 20 rac-3-{4-[5-(2-Isobutylamino-6-methyl-pyrimidin-4-yl)-[1,2,4]oxadiazol-3-yl]-2,6-dimethyl-phenoxy}-propane-1,2-diol rac-3-{4-[5-(2-Isobutylamino-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-isobutylamino-6-methyl-pyrimidine-4-carboxylic acid; white crystalline solid; LC-MS: $t_R$=0.90 min*; [M+H]$^+$=428.25; $^1$H NMR (D$_6$-DMSO): δ 0.93 (d, J=6.8 Hz, 6H), 1.91 (m, 1H), 2.35 (s, 6H), 2.41 (s, 3H), 3.18 (m, 2H), 3.50 (t, J=5.5 Hz, 2H), 3.75 (dd, J=5.5 and 8.8 Hz, 1H), 3.79-3.91 (m, 2H), 4.64 (t, J=5.5 Hz, 1H), 4.96 (d, J=5.0 Hz, 1H), 7.28 (s, 1H), 7.65 (s br, 1H), 7.76 (s, 2H).

Example 21 rac-3-{4-[5-(2-Dimethylamino-6-methyl-pyrimidin-4-yl)-[1,2,4]oxadiazol-3-yl]-2,6-dimethyl-phenoxy}-propane-1,2-diol rac-3-{4-[5-(2-Dimethylamino-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-dimethylamino-6-methyl-pyrimidine-4-carboxylic acid; LC-MS: $t_R$=0.89 min*; [M+H]$^+$=400.11.

Example 22 rac-3-{4-[5-(2-Diethylamino-6-methyl-pyrimidin-4-yl)-[1,2,4]oxadiazol-3-yl]-2,6-dimethyl-phenoxy}-propane-1,2-diol rac-3-{4-[5-(2-Diethylamino-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-diethylamino-6-methyl-pyrimidine-4-carboxylic acid; LC-MS: $t_R$=1.02 min*; [M+H]$^+$=428.02.

Example 23 rac-3-{4-[5-(2-(Ethyl-methylamino)-6-methyl-pyrimidin-4-yl)-[1,2,4]oxadiazol-3-yl]-2,6-dimethyl-phenoxy}-propane-1,2-diol rac-3-{4-[5-(2-(Ethyl-methylamino)-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-(ethyl-methyl)amino-6-methyl-pyrimidine-4-carboxylic acid; LC-MS: $t_R$=0.96 min*; [M+H]$^+$=414.10.

Example 24 rac-3-{4-[5-(2-Ethoxy-6-methyl-pyrimidin-4-yl)-[1,2,4]oxadiazol-3-yl]-2,6-dimethyl-phenoxy}-propane-1,2-diol rac-3-{4-[5-(2-Ethoxy-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-ethoxy-6-methyl-pyrimidine-4-carboxylic acid; LC-MS: $t_R$=0.81 min*; [M+H]$^+$=401.07.

Example 25 rac-3-{2,6-Dimethyl-4-[5-(6-methyl-2-propoxy-pyrimidin-4-yl)-[1,2,4]oxadiazol-3-yl]-phenoxy}-propane-1,2-diol rac-3-{2,6-Dimethyl-4-[5-(6-methyl-2-propoxy-pyrimidin-4-yl)-[1,2,4]oxadiazol-3-yl]-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 6-methyl-2-propoxy-pyrimidine-4-carboxylic acid; LC-MS: $t_R$=0.87 min*; [M+H]$^+$=415.08.

Example 26 rac-3-{4-[5-(2-Isopropoxy-6-methyl-pyrimidin-4-yl)-[1,2,4]oxadiazol-3-yl]-2,6-dimethyl-phenoxy}-propane-1,2-diol rac-3-{4-[5-(2-Isopropoxy-6-methyl-pyrimidin-4-yl)-[1,2,4]oxadiazol-3-yl]-2,6-dimethyl-phenoxy}-propane-1,2-diol is prepared in analogy to rac-3-{4-[5-(2-ethylamino-6-methyl-pyrimidin-4-yl)-[1,2,4]oxadiazol-3-yl]-2,6-dimethyl-phenoxy}-propane-1,2-diol using 2-isopropoxy-6-methyl-pyrimidine-4-carboxylic acid; LC-MS: $t_R$=0.86 min*; [M+H]$^+$=415.09.

Examples 27 to 43

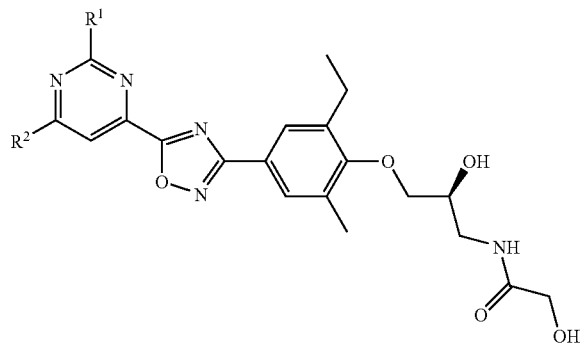

The following Examples are prepared starting from N—((S)-3-[2-ethyl-4-(N-hydroxycarbamimidoyl)-6-methyl-phenoxy]-2-hydroxy-propyl)-2-hydroxy-acetamide and the appropriate pyrimidine-4-carboxylic acid in analogy to the procedure given in Example 1.

| Ex. No. | R¹ | R² | LC-MS $t_R$ [min] | [M + H]⁺ | Amount Form |
|---|---|---|---|---|---|
| 27 | NHMe | Me | 0.80 | 457.13 | 28 mg white solid |
| 28 | NH-iPr | Me | 0.91 | 485.14 | 86 mg yellow solid |
| 29 | N(Me)(iBu) | Me | 1.05 | 513.16 | 47 mg yellow solid |
| 30 | pyrrolidinyl | Me | 0.95 | 497.16 | 11 mg white solid |
| 31 | NH-cyclopropyl | Me | 0.87 | 483.06 | 8 mg white solid |
| 32 | NH-CH₂-cyclopropyl | Me | 0.92 | 497.16 | 37 mg yellow solid |
| 33 | NHEt | Et | 0.93 | 485.28 | 72 mg yellow solid |
| 34 | NHMe | nPr | 0.91 | 485.09 | 23 mg white solid |
| 35 | NHMe | iBu | 0.93 | 498.77 | 23 mg yellow solid |
| 36 | NH-iPr | iBu | 1.02 | 527.2 | 28 mg colorless wax |
| 37 | NMe₂ | iBu | 1.06 | 513.12 | 40 mg yellow wax |
| 38 | OMe | Me | 0.86 | 458.05 | 12 mg white solid |
| 39 | O-iPr | Me | 0.94 | 486.31 | 15 mg colorless wax |
| 40 | O-iBu | Me | 0.99 | 500.33 | 79 mg yellow solid |
| 41 | OEt | Et | 0.94 | 486.10 | 8 mg white solid |
| 42 | OMe | nPr | 0.94 | 486.13 | 8 mg beige wax |
| 43 | OMe | iBu | 0.97 | 500.08 | 47 mg colorless wax |

Example 28

¹H NMR (CDCl₃): δ 1.31 (m, 9H), 2.38 (s, 3H), 2.50 (s, 3H), 2.56 (m, 1H), 2.74 (q, J=7.5 Hz, 2H), 3.34 (d, J=2.8 Hz, 1H), 3.55 (m, 1H), 3.81 (m, 2H), 3.91 (m, 1H), 4.21 (m, 3H), 4.32 (m, 1H), 5.28 (m, 1H), 6.99 (m, 1H), 7.30 (s, 1H), 7.91 (s, 1H), 7.92 (s, 1H).

Example 32

¹H NMR (CDCl₃): δ 0.32 (m, 2H), 0.57 (m, 2H), 1.13 (m, 1H), 1.31 (t, J=7.5 Hz, 3H), 2.38 (s, 3H), 2.50 (s, 3H), 2.74 (q, J=7.5 Hz, 2H), 3.41 (t, J=5.8 Hz, 2H), 3.55 (m, 1H), 3.81 (m, 2H), 3.90 (m, 1H), 4.20 (m, 3H), 5.60 (m, 1H), 7.04 (m, 1H), 7.32 (s, 1H), 7.89 (s, 1H), 7.90 (s, 1H).

Example 36

¹H NMR (CDCl₃): δ 1.01 (d, J=6.5 Hz, 6H), 1.30 (m, 9H), 2.22 (m, 1H), 2.38 (m, 3H), 2.59 (d, J=7.3 Hz, 2H), 2.74 (q, J=7.5 Hz, 2H), 3.05 (s br, 1H), 3.52 (m, 2H), 3.81 (m, 2H), 3.90 (m, 1H), 4.20 (m, 3H), 4.29 (m, 1H), 5.31 (m, 1H), 7.09 (s, 1H), 7.29 (s, 1H), 7.89 (s, 1H), 7.90 (s, 1H).

Example 38

¹H NMR (CDCl₃): δ 1.31 (t, J=7.5 Hz, 3H), 2.37 (m, 3H), 2.64 (m, 3H), 2.74 (q, J=7.5 Hz, 2H), 3.55 (dd, J=7.0, 5.5 Hz, 1H), 3.81 (m, 2H), 3.91 (m, 1H), 4.16 (m, 3H), 4.20 (m, 3H), 7.13 (m, 1H), 7.74 (s, 1H), 7.88 (s, 1H), 7.89 (s, 1H).

Example 42

¹H NMR (CDCl₃): δ 1.05 (t, J=7.5 Hz, 3H), 1.32 (t, J=7.5 Hz, 3H), 1.88 (m, 2H), 2.39 (m, 3H), 2.75 (m, 2H), 2.85 (m,

2H), 3.54 (m, 1H), 3.82 (m, 2H), 3.91 (m, 1H), 4.17 (m, 3H), 4.20 (m, 3H), 7.03 (m, 1H), 7.73 (s, 1H), 7.90 (s, 1H), 7.91 (s, 1H).

Examples 44 to 45

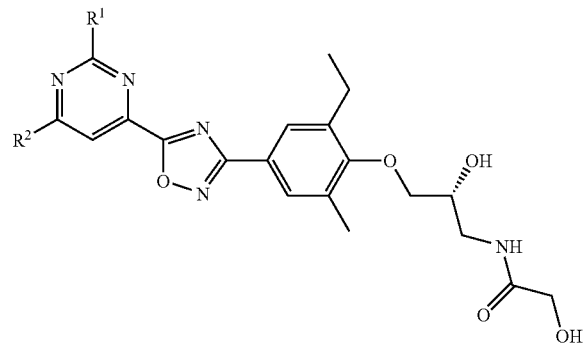

The following Examples are prepared starting from N—((R)-3-[2-ethyl-4-(N-hydroxycarbamimidoyl)-6-methyl-phenoxy]-2-hydroxy-propyl)-2-hydroxy-acetamide and the appropriate pyrimidine-4-carboxylic acid in analogy to the procedure given in Example 1.

| Ex. No. | R¹ | R² | LC-MS $t_R$ [min] | [M + H]⁺ | Amount Form |
|---|---|---|---|---|---|
| 44 | ⋯O⟨iBu⟩ | Me | 1.02 | 500.49 | 15 mg yellow solid |
| 45 | ⋯O⟨Et⟩ | Et | 0.95 | 486.11 | 7 mg yellow solid |

Examples 46 to 47

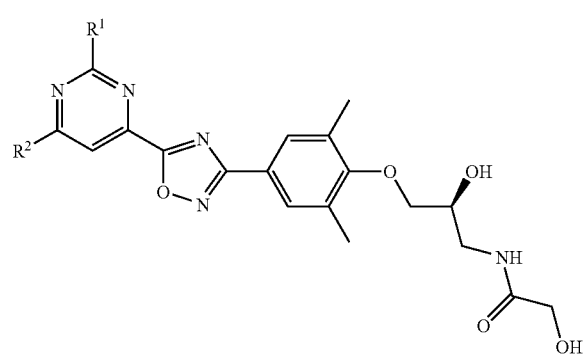

The following Examples are prepared starting from (S)-2-hydroxy-N-{2-hydroxy-3-[4-(N-hydroxycarbamimidoyl)-2,6-dimethyl-phenoxy]-propyl}-acetamide and the appropriate pyrimidine-4-carboxylic acid in analogy to the procedure given in Example 1.

| Ex. No. | R¹ | R² | LC-MS $t_R$ [min] | [M + H]⁺ | Amount Form |
|---|---|---|---|---|---|
| 46 | ⋯O⟨iBu⟩ | Me | 0.99 | 486.53 | 12 mg yellow foam |
| 47 | ⋯O⟨Et⟩ | Et | 0.92 | 472.11 | 9 mg white solid |

Example 46

¹H NMR (CDCl₃): δ 1.09 (d, J=6.8 Hz, 6H), 2.18 (m, 1H), 2.33 (s, 6H), 2.61 (s, 3H), 3.54 (m, 1H), 3.74 (m, 1H), 3.85 (m, 2H), 4.07 (s, 1H), 4.17 (m, 4H), 4.27 (d, J=6.5 Hz, 2H), 7.36 (t, J=5.8 Hz, 1H), 7.67 (s, 1H), 7.81 (s, 2H).

Examples 48 to 49

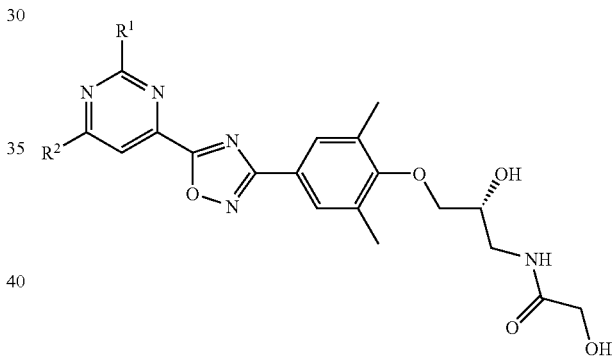

The following Examples are prepared starting from (R)-2-hydroxy-N-{2-hydroxy-3-[4-(N-hydroxycarbamimidoyl)-2,6-dimethyl-phenoxy]-propyl}-acetamide and the appropriate pyrimidine-4-carboxylic acid in analogy to the procedure given in Example 1.

| Ex. No. | R¹ | R² | LC-MS $t_R$ [min] | [M + H]⁺ | Amount Form |
|---|---|---|---|---|---|
| 48 | ⋯O⟨iBu⟩ | Me | 0.99 | 486.36 | 9 mg yellow solid |
| 49 | ⋯O⟨Et⟩ | Et | 0.92 | 472.09 | 4 mg white solid |

Examples 50 to 57

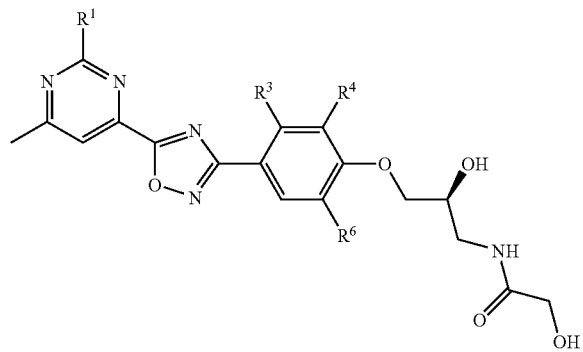

The following Examples are prepared starting from (S)—N—(-3-[2-chloro-4-(N-hydroxycarbamimidoyl)-6-methyl-phenoxy]-2-hydroxy-propyl)-2-hydroxy-acetamide (Ex. 50 and 54) or (S)-2-hydroxy-N-(2-hydroxy-3-[4-(N-hydroxy-carbamimidoyl)-2-methoxy-6-methyl-phenoxy]-propyl)-acetamide (Ex. 51 and 55) or (S)-2-hydroxy-N-(2-hydroxy-3-[4-(N-hydroxycarbamimidoyl)-3-methyl-phenoxy]-propyl)-acetamide (Ex. 52 and 56) or (S)-2-hydroxy-N-(2-hydroxy-3-[4-(N-hydroxycarbamimidoyl)-3-methoxy-phenoxy]-propyl)-acetamide (Ex. 53 and 57) and the appropriate pyrimidine-4-carboxylic acid in analogy to the procedure given in Example 1.

| Ex. No. | $R^1$ | $R^3$ | $R^4$ | $R^6$ | LC-MS $t_R$ [min] | $[M+H]^+$ | Amount Form |
|---|---|---|---|---|---|---|---|
| 50 | H-N-iPr | H | Me | Cl | 0.92 | 490.781 | 188 mg yellow solid |
| 51 | H-N-iPr | H | OMe | Me | 0.88 | 487.07 | 13 mg beige solid |
| 52 | H-N-iPr | Me | H | H | 0.86 | 457.02 | 40 mg beige solid |
| 53 | H-N-iPr | OMe | H | H | 0.80 | 473.06 | 9 mg beige solid |
| 54 | O-iPr | H | Me | Cl | 0.93 | 492.01 | 19 mg white solid |
| 55 | O-iPr | H | OMe | Me | 0.90 | 488.11 | 2.4 mg white solid |
| 56 | O-iPr | Me | H | H | 0.88 | 457.95 | 17 mg beige solid |
| 57 | O-iPr | OMe | H | H | 0.82 | 473.97 | 7 mg yellow glass |

Example 51

$^1$H NMR (CDCl$_3$): δ 1.29 (d, J=6.3 Hz, 6H), 2.35 (s, 3H), 2.48 (s, 3H), 3.47 (m, 1H), 3.73 (m, 1H), 3.96 (m, 4H), 4.09 (m, 2H), 4.17 (m, 2H), 4.30 (m, 1H), 5.30 (m, 1H), 7.17 (m, 1H), 7.28 (s, 1H), 7.56 (d, J=1.5 Hz, 1H), 7.67 (s, 1H).

Example 54

$^1$H NMR (CDCl$_3$): δ 1.47 (d, J=6.3 Hz, 6H), 2.43 (s, 3H), 2.63 (s, 3H), 2.82 (s br, 1H), 3.57 (m, 2H), 3.81 (ddd, J=14.1, 6.5, 3.3 Hz, 1H), 4.00 (m, 1H), 4.06 (m, 1H), 4.23 (m, 3H), 5.48 (m, 1H), 7.08 (m, 1H), 7.69 (s, 1H), 7.95 (d, J=1.5 Hz, 1H), 8.09 (d, J=2.3 Hz, 1H).

Example 56

$^1$H NMR (CDCl$_3$): δ 1.47 (d, J=6.0 Hz, 6H), 2.61 (s, 3H), 2.68 (s, 3H), 3.53 (m, 1H), 3.72 (m, 1H), 4.05 (d, J=4.5 Hz, 2H), 4.19 (m, 3H), 5.48 (m, 1H), 6.87 (m, 2H), 7.15 (m, 1H), 7.67 (s, 1H), 8.06 (d, J=8.8 Hz, 1H).

Examples 58 to 73

The following Examples are prepared starting from (R)-4-(2,2-dimethyl-[1,3]dioxolan-4-ylmethoxy)-3-ethyl-N-hydroxy-5-methyl-benzamidine or (R)-4-(2,2-dimethyl-[1,3]dioxolan-4-ylmethoxy)-N-hydroxy-3,5-dimethyl-benzamidine and the appropriate pyrimidine-4-carboxylic acid in analogy to Method A given in Example 16.

| Ex. No. | $R^1$ | $R^2$ | $R^4$ | LC-MS $t_R$ [min] | $[M+H]^+$ | Amount Form |
|---|---|---|---|---|---|---|
| 58 | NHMe | Me | Et | 0.87 | 400.07 | 6 mg white solid |

-continued

| Ex. No. | R¹ | R² | R⁴ | LC-MS $t_R$ [min] | [M + H]⁺ | Amount Form |
|---|---|---|---|---|---|---|
| 59 | -NH-CH(CH₃)CH₂CH₃ | Me | Et | 0.96 | 428.09 | 30 mg yellow solid |
| 60 | -NH-CH₂CH(CH₃)₂ | Me | Et | 1.00 | 442.04 | 23 mg yellow oil |
| 61 | -N(Me)-CH₂CH(CH₃)₂ | Me | Et | 1.11 | 456.10 | 24 mg yellow oil |
| 62 | pyrrolidinyl | Me | Et | 1.00 | 440.06 | 23 mg yellow solid |
| 63 | -NH-cyclopropyl | Me | Et | 0.92 | 425.99 | 16 mg yellow wax |
| 64 | -NH-CH₂-cyclopropyl | Me | Et | 0.97 | 440.07 | 18 mg white solid |
| 65 | -NH-Et | Et | Et | 0.96 | 428.09 | 63 mg yellow solid |
| 66 | NHMe | iBu | Et | 0.98 | 442.02 | 11 mg yellow solid |
| 67 | NHMe | nPr | Et | 0.96 | 428.11 | 12 mg yellow solid |
| 68 | OMe | Me | Et | 0.91 | 401.02 | 5 mg beige solid |
| 69 | -O-CH(CH₃)₂ | Me | Et | 0.98 | 429.05 | 15 mg white solid |
| 70 | -O-CH₂CH(CH₃)₂ | Me | Et | 1.03 | 442.87 | 61 mg yellow solid |
| 71 | OMe | nPr | Et | 0.99 | 429.08 | 18 mg beige wax |
| 72 | OMe | iBu | Et | 1.02 | 442.91 | 14 mg white solid |
| 73 | -NH-Et | Et | Me | 0.93 | 428.01 | 4 mg yellow solid |

Example 60

¹H NMR (CDCl₃): δ 1.09 (d, J=6.5 Hz, 6H), 1.31 (t, J=7.5 Hz, 3H), 2.07 (m, 1H), 2.37 (s, 3H), 2.73 (m, 5H), 3.56 (t, J=5.8 Hz, 2H), 3.82 (m, 1H), 3.89 (m, 3H), 4.16 (m, 1H), 7.40 (s, 1H), 7.77 (s, 1H), 7.79 (s, 1H), 8.85 (s, 1H).

Example 65

¹H NMR (CDCl₃): δ 1.24-1.37 (m, 9H), 2.37 (s, 3H), 2.74 (m, 5H), 3.20 (s br, 1H), 3.57 (quint, J=6.8 Hz, 2H), 3.83 (m, 1H), 3.91 (m, 3H), 4.17 (m, 1H), 5.53 (s, 1H), 7.30 (s, 1H), 7.87 (s, 1H), 7.89 (s, 1H).

Example 69

¹H NMR (CDCl₃): δ 1.32 (t, J=7.5 Hz, 3H), 1.47 (d, J=6.3 Hz, 6H), 2.18 (m, 1H), 2.40 (s, 3H), 2.62 (s, 3H), 2.76 (q, J=7.5 Hz, 2H), 2.81 (s br, 1H), 3.85 (m, 1H), 3.94 (m, 3H), 4.17 (m, 1H), 5.49 (hept, J=6.0 Hz, 1H), 7.70 (s, 1H), 7.89 (s, 1H), 7.90 (s, 1H).

Example 71

¹H NMR (CDCl₃): δ 1.05 (t, J=7.3 Hz, 3H), 1.33 (t, J=7.5 Hz, 3H), 1.88 (h, J=7.5 Hz, 2H), 2.09 (m, 1H), 2.41 (s, 3H), 2.74 (s br, 1H), 2.77 (q, J=7.8 Hz, 2H), 2.85 (m, 2H), 3.85 (m, 1H), 3.92 (m, 1H), 3.96 (m, 2H), 4.17 (s, 4H), 7.74 (s, 1H), 7.91 (s, 1H), 7.92 (s, 1H).

Example 74 rac-3-{4-[5-(2-Methoxy-6-methyl-pyrimidin-4-yl)-[1,2,4]oxadiazol-3-yl]-2,6-dimethyl-phenoxy}-propane-1,2-diol The title compound is prepared in analogy to Example 16 (Method A) starting from 2-methoxy-6-methyl-pyrimidine-4-carboxylic acid; LC-MS: $t_R$=0.88 min; [M+H]⁺=387.11.

Examples 75 to 76

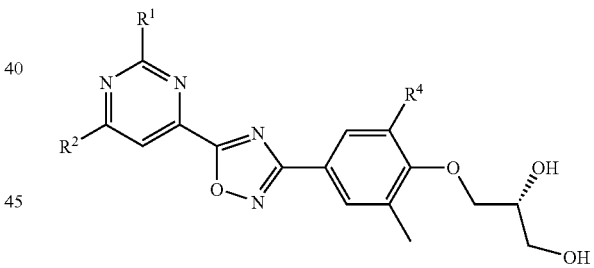

The following Examples are prepared starting from (S)-4-(2,2-dimethyl-[1,3]dioxolan-4-ylmethoxy)-3-ethyl-N-hydroxy-5-methyl-benzamidine or (S)-4-(2,2-dimethyl-[1,3]dioxolan-4-ylmethoxy)-N-hydroxy-3,5-dimethyl-benzamidine and 6-ethyl-2-ethylamino-pyrimidine-4-carboxylic acid in analogy to Method A given in Example 16.

| Ex. No. | R¹ | R² | R⁴ | LC-MS $t_R$ [min] | [M + H]⁺ | Amount Form |
|---|---|---|---|---|---|---|
| 75 | -NH-Et | Et | Et | 0.96 | 428.09 | 11 mg yellow solid |
| 76 | -NH-Et | Et | Me | 0.93 | 414.07 | 15 mg yellow solid |

Example 75

¹H NMR (CDCl₃): δ 1.25-1.37 (m, 9H), 2.39 (s, 3H), 2.61 (s, 1H), 2.75 (m, 4H), 2.89 (s br, 1H), 3.58 (quint, J=7.0 Hz, 2H), 3.87 (m, 2H), 3.96 (m, 2H), 4.17 (m, 1H), 5.42 (s br, 1H), 7.32 (s, 1H), 7.90 (s, 1H), 7.91 (s, 1H).

Examples 77 to 84

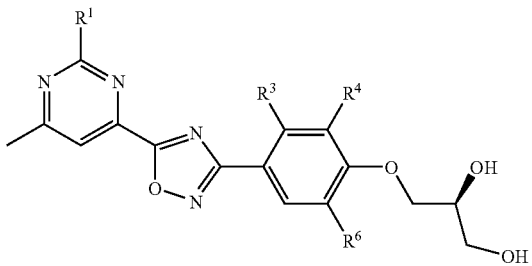

The following Examples are prepared starting from (R)-3-chloro-4-(2,2-dimethyl-[1,3]dioxolan-4-ylmethoxy)-N-hydroxy-5-methyl-benzamidine (Ex. 77 and 81) or (R)-4-(2,2-dimethyl-[1,3]dioxolan-4-ylmethoxy)-N-hydroxy-3-methoxy-5-methyl-benzamidine (Ex. 78 and 82) or (R)-4-(2,2-dimethyl-[1,3]dioxolan-4-ylmethoxy)-N-hydroxy-2-methoxy-benzamidine (Ex. 79 and 83) or (R)-4-(2,2-dimethyl-[1,3]dioxolan-4-ylmethoxy)-N-hydroxy-2-methyl-benzamidine (Ex. 80 and 84) and the appropriate pyrimidine-4-carboxylic acid in analogy to Method A given in Example 16.

| Ex. No. | R¹ | R³ | R⁴ | R⁶ | $t_R$ [min] | [M + H]⁺ | Amount Form |
|---|---|---|---|---|---|---|---|
| 77 | ⋯NH-iPr | H | Me | Cl | 0.96 | 433.94 | 12 mg yellow solid |
| 78 | ⋯NH-iPr | H | OMe | Me | 0.92 | 430.05 | 16 mg white solid |
| 79 | ⋯NH-iPr | Me | H | H | 0.90 | 400.06 | 8 mg beige solid |
| 80 | ⋯NH-iPr | OMe | H | H | 0.83 | 415.99 | 16 mg colorless wax |
| 81 | ⋯O-iPr | H | Me | Cl | 0.97 | 434.91 | 7.5 mg white solid |
| 82 | ⋯O-iPr | H | OMe | Me | 0.94 | 430.98 | 14 mg white solid |
| 83 | ⋯O-iPr | Me | H | H | 0.92 | 401.04 | 15 mg beige solid |
| 84 | ⋯O-iPr | OMe | H | H | 0.85 | 417.00 | 15 mg yellow solid |

Example 78

¹H NMR (CDCl₃): δ 1.30 (d, J=6.5 Hz, 6H), 2.29 (m, 1H), 2.39 (s, 3H), 2.50 (s, 3H), 3.41 (d, J=4.3 Hz, 1H), 3.83 (m, 2H), 3.99 (m, 3H), 4.06 (m, 2H), 4.16 (m, 1H), 4.31 (m, 1H), 5.27 (m, 1H), 7.30 (s, 1H), 7.60 (d, J=1.5 Hz, 1H), 7.71 (d, J=1.3 Hz, 1H).

Example 83

¹H NMR (CDCl₃): δ 1.47 (d, J=6.3 Hz, 6H), 2.07 (t, J=5.8 Hz, 1H), 2.62 (s, 3H), 2.65 (d, J=4.0 Hz, 1H), 2.70 (s, 3H), 3.81 (m, 1H), 3.90 (m, 1H), 4.16 (m, 3H), 5.48 (m, 1H), 6.90 (s, 1H), 7.69 (s, 2H), 8.10 (d, J=8.8 Hz, 1H).

Example 85

(S)—N-(3-{2-Ethyl-4-[3-(2-isopropylamino-6-methyl-pyrimidin-4-yl)-[1,2,4]oxadiazol-5-yl]-6-methyl-phenoxy}-2-hydroxy-propyl)-2-hydroxy-acetamide a) To a solution of 4-benzyloxy-3-ethyl-5-methyl-benzoic acid (893 mg, 3.30 mmol) in DMF (20 mL), DIPEA (1.70 mL, 9.9 mmol) is added followed by TBTU (1.27 g, 3.96 mmol). The reaction mixture is stirred for 15 min before adding N-hydroxy-2-isopropylamino-6-methyl-pyrimidine-4-carboxamidine (691 mg, 3.30 mmol). After 3 h, the reaction mixture is diluted with EtOAc, and the org. solution is washed with sat. aq. NaHCO₃, dried over MgSO₄, filtered and evaporated to give the hydroxyamidine ester intermediate. This material is dissolved in dioxane (10 mL) and the resulting solution is stirred at 95° C. for 7 days. The solvent is removed in vacuo and the crude compound is purified by CC on silica gel to give the desired {4-[5-(4-benzyloxy-3-ethyl-5-methyl-phenyl)-[1,2,4]oxadiazol-3-yl]-6-methyl-pyrimidin-2-yl}-isopropyl-amine (322 mg) as a yellow oil; LC-MS: $t_R$=1.19 min; [M+H]⁺=444.09.

b) The above benzyloxy derivative (321 mg, 0.72 mmol) is dissolved in EtOAc (3 mL) and a solution of 33% HBr in acetic acid (1 mL) is added. The reaction mixture is stirred at rt for 18 h, then is diluted with EtOAc and neutralized with sat. aq. NaHCO₃. The org. phase is dried over MgSO₄, filtered, and evaporated to give 2-ethyl-4-[3-(2-isopropylamino-6-methyl-pyrimidin-4-yl)-[1,2,4]oxadiazol-5-yl]-6-methyl-phenol (278 mg) as a yellow solid; LC-MS: $t_R$=0.99; [M+H]⁺=354.05.

c) 2-Ethyl-4-[3-(2-isopropylamino-6-methyl-pyrimidin-4-yl)-[1,2,4]oxadiazol-5-yl]-6-methyl-phenol is reacted with R-epichlorohydrine in analogy to Intermediate 1 to give (S)-{4-[5-(3-ethyl-5-methyl-4-oxiranyl methoxy-phenyl)-[1,2,4]oxadiazol-3-yl]-6-methyl-pyrimidin-2-yl}-iso-propyl-amine as a yellow oil; LC-MS: $t_R$=1.10 min; $[M+H]^+$=410.55.

d) A solution of (S)-{4-[5-(3-ethyl-5-methyl-4-oxiranyl-methoxy-phenyl)-[1,2,4]oxadiazol-3-yl]-6-methyl-pyrimidin-2-yl}-iso-propyl-amine (48 mg, 0.12 mmol) in 7M $NH_3$ in MeOH (5 mL) is stirred at 65° C. for 24 h. Volatiles are removed in vacuo to give the crude 1-amino-3-{2-ethyl-4-[3-(2-isopropylamino-6-methyl-pyrimidin-4-yl)-[1,2,4]oxadiazol-5-yl]-6-methyl-phenoxy}-propan-2-ol as a yellow oil (43 mg); LC-MS: $t_R$=0.76 min; $[M+H]^+$=426.80.

e) To a solution of crude 1-amino-3-{2-ethyl-4-[3-(2-isopropylamino-6-methyl-pyrimidin-4-yl)-[1,2,4]oxadiazol-5-yl]-6-methyl-phenoxy}-propan-2-ol (43 mg, 97 μmol) in DMF, glycolic acid (11 mg, 146 μmol), HOBt (20 mg, 146 μmol), and EDC hydrochloride (28 mg, 146 μmol) are added. The mixture is stirred at rt for 18 h before it is diluted with sat. aq. $NaHCO_3$ and extracted twice with EtOAc. The combined org. extracts are dried over $MgSO_4$, filtered and concentrated. The crude product is purified by prep. TLC plates with DCM containing 10% of 7M $NH_3$ in MeOH to give (S)—N-(3-{2-ethyl-4-[3-(2-isopropylamino-6-methyl-pyrimidin-4-yl)-[1,2,4]oxadiazol-5-yl]-6-methyl-phenoxy}-2-hydroxy-propyl)-2-hydroxy-acetamide (21 mg) as a white solid; LC-MS: $t_R$=0.85 min; $[M+H]^+$=485.14; $^1$H NMR ($CDCl_3$): δ 1.29 (m, 9H), 2.35 (m, 3H), 2.46 (s, 3H), 2.72 (q, J=7.5 Hz, 2H), 3.52 (m, 1H), 3.76 (m, 1H), 3.87 (m, 3H), 4.20 (m, 3H), 4.31 (m, 1H), 5.31 (m, 1H), 7.22 (s, 1H), 7.25 (t, J=6.0 Hz, 1H), 7.89 (s, 1H), 7.91 (s, 1H).

Example 86

(S)—N-[3-(2-Ethyl-4-{3-[2-(isobutyl-methyl-amino)-6-methyl-pyrimidin-4-yl]-[1,2,4]oxadiazol-5-yl}-6-methyl-phenoxy)-2-hydroxy-propyl]-2-hydroxy-acetamide The title compound is prepared in analogy to Example 85 using 2-N-isobutyl-N-methyl-amino-6-methyl-pyrimidine-4-carboxylic acid; LC-MS: $t_R$=1.0 min; $[M+1]^+$=513.16.

Examples 87 to 94

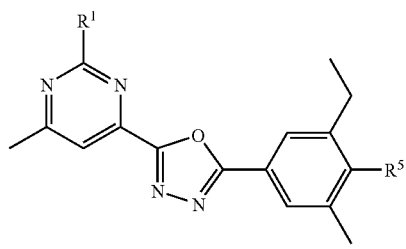

Examples 87, 88, 89 and 90 are prepared from Intermediate 1, 2, 3 and 4, respectively, following the procedures described for Example 85 (paragraph c) to e)).

Examples 91, 92, 93 and 94 are prepared from Intermediate 1, 2, 3 and 4, respectively, as described below:

To a solution of 1 eq. of Intermediate 1, 2, 3, or 4 (concentration: 0.02 mol/L) in iPrOH, 3M aq. NaOH followed by S-3-chloro-1,2-propanediol (10 eq.) is added. The reaction mixture is stirred at rt for 15-48 h (monitored by LC-MS), and is then diluted with EtOAc and washed with 1M aq. NaOH followed by brine. The org. solution is dried over $Na_2SO_4$, filtered, and evaporated. The crude compound is purified by prep. HPLC or prep. TLC.

| Ex. No. | Prepared from Intermediate | $R^1$ | $R^5$ | LC-MS $t_R$ [min] | $[M + H]^+$ | Amount Form |
|---|---|---|---|---|---|---|
| 87 | 1 | | ----O-CH2-CH(OH)-CH2-NH-C(O)-CH2-OH | 0.83 | 485.2 | 15 mg yellow solid |
| 88 | 2 | | ----O-CH2-CH(OH)-CH2-NH-C(O)-CH2-OH | 0.87 | 498.83 | 19 mg yellow solid |
| 89 | 3 | | ----O-CH2-CH(OH)-CH2-NH-C(O)-CH2-OH | 0.88 | 486.14 | 20 mg yellow solid |

-continued

| Ex. No. | Prepared from Intermediate | R¹ | R⁵ | LC-MS $t_R$ [min] | $[M + H]^+$ | Amount Form |
|---|---|---|---|---|---|---|
| 90 | 4 | (isobutoxy) | (glycerol-NH-CO-CH₂-OH) | 0.96 | 500.32 | 13 mg yellow solid |
| 91 | 1 | (isopropylamino) | (glycerol-OH) | 0.87 | 428.11 | 7 mg white solid |
| 92 | 2 | (isobutylamino) | (glycerol-OH) | 0.91 | 442.04 | 5 mg white solid |
| 93 | 3 | (isopropoxy) | (glycerol-OH) | 0.92 | 429.09 | 6 mg yellow solid |
| 94 | 4 | (isobutoxy) | (glycerol-OH) | 1.01 | 443.21 | 6 mg yellow oil |

Example 89

$^1$H NMR (CDCl$_3$): δ 1.29 (t, J=7.3 Hz, 3H), 1.47 (d, J=6.3 Hz, 6H), 2.38 (s, 3H), 2.60 (s, 3H), 2.74 (q, J=7.5 Hz, 2H), 3.55 (m, 2H), 3.77 (m, 1H), 3.87 (m, 2H), 4.18 (m, 3H), 5.47 (m, 1H), 5.70 (m, 1H), 7.22 (m, 1H), 7.69 (s, 1H), 7.88 (s, 1H), 7.89 (s, 1H).

Example 91

$^1$H NMR (CDCl$_3$): δ 1.31 (d, J=6.5 Hz, 6H), 1.33 (t, J=7.0 Hz, 3H), 2.41 (s, 3H), 2.48 (s, 3H), 2.72 (m, 1H), 2.77 (q, J=7.5 Hz, 2H), 3.85 (m, 1H), 3.91 (m, 1H), 3.96 (m, 2H), 4.18 (m, 1H), 4.32 (m, 1H), 5.21 (m, 1H), 7.89 (s, 1H), 7.91 (m, 1H).

Examples 95 to 99

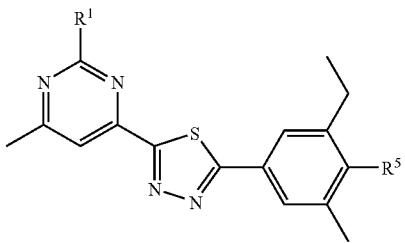

Examples 95 to 99 are prepared in analogy to Examples 87-94 starting from Intermediate 5, 6 and 7, respectively.

| Ex. No. | Prepared from Intermediate | R¹ | R⁵ | LC-MS $t_R$ [min] | $[M + H]^+$ | Amount Form |
|---|---|---|---|---|---|---|
| 95 | 5 | (isopropylamino) | (glycerol-NH-CO-CH₂-OH) | 0.85 | 501.13 | 15 mg yellow solid |

-continued

| Ex. No. | Prepared from Intermediate | R¹ | R⁵ | LC-MS $t_R$ [min] | [M + H]⁺ | Amount Form |
|---|---|---|---|---|---|---|
| 96 | 7 | (isobutoxy group) | (glycerol ether with NH-CO-CH₂OH) | 1.02 | 516.30 | 12 mg white solid |
| 97 | 5 | (isopropylamino) | (glycerol ether diol) | 0.89 | 444.08 | 9 mg yellow solid |
| 98 | 6 | (isobutylamino) | (glycerol ether diol) | 0.93 | 458.03 | 12 mg yellow solid |
| 99 | 7 | (isobutoxy) | (glycerol ether diol) | 1.07 | 459.73 | 7 mg yellow wax |

Example 96

¹H NMR (CDCl₃): δ 1.10 (d, J=6.8 Hz, 6H), 1.30 (t, J=7.5 Hz, 3H), 2.20 (m, 1H), 2.37 (s, 3H), 2.59 (s, 3H), 2.73 (q, J=7.8 Hz, 2H), 3.54 (m, 1H), 3.77 (m, 1H), 3.86 (m, 2H), 4.21 (m, 5H), 7.23 (t, J=5.8 Hz, 1H), 7.70 (d, J=1.8 Hz, 1H), 7.74 (d, J=2.0 Hz, 1H), 7.78 (s, 1H).

Example 97

¹H NMR (CDCl₃): δ 1.04 (d, J=6.5 Hz, 6H), 1.33 (t, J=7.5 Hz, 3H), 1.96 (m, 1H), 2.07 (s br, 1H), 2.41 (s, 3H), 2.47 (s, 3H), 2.72 (S br, 1H), 2.77 (q, J=7.3 Hz, 2H), 3.35 (t, J=6.3 Hz, 2H), 3.84 (m, 1H), 3.91 (m, 1H), 3.96 (m, 2H), 4.18 (m, 1H), 5.26 (m, 1H), 7.42 (s, 1H), 7.75 (d, J=2.0 Hz, 1H), 7.78 (d, J=2.0 Hz, 1H).

Example 100

2-{4-[5-(2-Diethylamino-6-methyl-pyrimidin-4-yl)-[1,2,4]oxadiazol-3-yl]-2-ethyl-6-methyl-phenoxy}-propane-1,3-diol To a solution of Intermediate 11 (150 mg, 0.41 mmol) in acetonitrile (10 mL) are added K₂CO₃ (80 mg, 0.61 mmol) and dimethylchloromalonate (82 mg, 0.49 mmol). The reaction mixture is stirred at 65° C. for 3 h, and is then diluted with EtOAc, washed with water, dried over MgSO₄, filtered and evaporated. The residue is purified by prep. TLC (eluting with Heptane/EA 4:1) and is then dissolved in ethanol (10 mL). NaBH₄ (60 mg, 1.59 mmol) is added and the reaction mixture is stirred at rt for 3 h. After cooling to 5° C., water is added and the compound is extracted twice with EtOAc. The org. phase is dried over MgSO₄, filtered, concentrated and purified by prep. TLC (eluting with Heptane/EA 1:1) to give the title compound as a yellow wax (54 mg); LC-MS: $t_R$=1.06 min; [M+H]⁺=442.0.

Example 101

2-{4-[5-(2-Diethylamino-6-methyl-pyrimidin-4-yl)-[1,2,4]oxadiazol-3-yl]-2-ethyl-6-methyl-phenoxymethyl}-propane-1,3-diol 2-Diethylamino-6-methyl-pyrimidine-4-carboxylic acid (180 mg, 0.86 mmol) is reacted with 4-(2,2-dimethyl-[1,3]dioxan-5-ylmethoxy)-3-ethyl-N-hydroxy-5-methyl-benzamidine (277 mg, 0.86 mmol) in analogy to isopropyl-{4-methyl-6-[3-(4-vinyl-phenyl)-[1,2,4]oxadiazol-5-yl]-pyrimidin-2-yl}-amine (Intermediate 8) using HOBt and EDC followed by cyclization in dioxane to give the oxadiazole intermediate (150 mg). The acetal function is then hydrolyzed with 4M HCl in dioxane (5 mL) to give the title compound as a yellow solid (92 mg) after purification by prep. TLC (eluting with DCM/MeOH 9:1); LC-MS: $t_R$=1.10 min; [M+H]⁺=456.14.

Example 102

2-{4-[5-(2-Diethylamino-6-methyl-pyrimidin-4-yl)-[1,2,4]oxadiazol-3-yl]-2-ethyl-6-methyl-phenoxy}-ethanol To a solution of Intermediate 11 (1.5 g, 4.08 mmol) in isopropanol (20 mL) is added 3M aq. NaOH (5 mL) followed by bromoethanol (2.90 mL, 40.8 mmol). The reaction mixture is stirred at rt for 15 h, and is then diluted with EtOAc. The org. solution is washed with 1M aq. NaOH followed by brine, dried over Na₂SO₄, filtered and concentrated. The crude compound is purified by CC (eluting with Heptane/EA 4:1) to give the title compound as a yellow oil (1.77 g); LC-MS: $t_R$=1.16 min; [M+H]⁺=412.09. ¹H NMR (CDCl₃) δ1.26 (t, J=7.0 Hz, 6H), 1.33 (t, J=7.5 Hz, 3H), 2.41 (s, 3H), 2.47 (s, 3H), 2.78 (q, J=7.5 Hz, 2H), 2.16 (t, J=5.5 Hz, 1H), 3.76 (q, J=7.0 Hz, 4H), 4.01 (m, 4H), 7.23 (s, 1H), 7.90 (d, J=5.8 Hz, 2H).

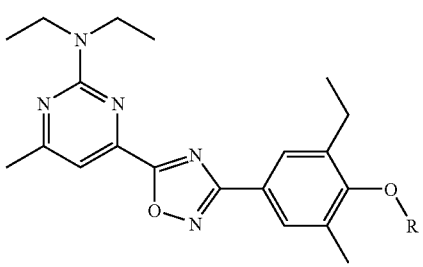

Examples 103 to 110

Examples 103 to 110 are prepared from Example 102 according to the general method described below:

a) To a solution of 2-{4-[5-(2-diethylamino-6-methyl-pyrimidin-4-yl)-[1,2,4]oxadiazol-3-yl]-2-ethyl-6-methyl-phenoxy}-ethanol (895 mg, 2.44 mmol) in DCM (20 mL) is added Et$_3$N (0.47 mL, 3.41 mmol). The reaction mixture is cooled down to 5° C. before adding methanesulfonylchloride (0.23 mL, 2.92 mmol) and stirring is continued at rt for 2 h. The mixture is then diluted with EtOAc and the org. solution is washed with sat. aq. NaHCO$_3$ followed by brine, is dried over MgSO$_4$, filtered and concentrated to give methanesulfonic acid 2-{4-[5-(2-diethylamino-6-methyl-pyrimidin-4-yl)-[1,2,4]oxadiazol-3-yl]-2-ethyl-6-methyl-phenoxy}-ethyl ester as a brown oil (1.07 g); LC-MS: $t_R$=1.19 min; [M+H]$^+$=489.89.

b) To a solution of the mesylate intermediate (1 eq.) in ethanol is added the appropriate nucleophile (4-5 eq.: ethanolamine or 3-azetidine carboxylic methylester, or S-proline methylester or 3-pyrrolidine carboxylic methylester or β-alanine). The reaction mixture is stirred at 80° C. for 2 h to 72 h (monitored by LC-MS), is then diluted with DCM and washed with sat. aq. NaHCO$_3$. The org. phase is dried, filtered and evaporated and the crude compound is purified by prep. TLC.

c) The amino acid derivatives 105, 107, and 109 are prepared by hydrolysis of their corresponding amino carboxylic esters 104, 106, and 108 using 20-30 eq. of 2M aq. LiOH in MeOH.

| Ex. No. | R | LC-MS $t_R$ [min] | [M + H]$^+$ | Amount Form |
|---|---|---|---|---|
| 103 | | 0.92 | 455.10 | 49 mg yellow oil |
| 104 | | 0.98 | 509.19 | 16 mg yellow oil |
| 105 | | 0.94 | 495.20 | 5 mg yellow oil |
| 106 | | 0.97 | 522.84 | 43 mg yellow oil |
| 107 | | 0.94 | 509.17 | 25 mg yellow oil |
| 108 | | 0.99 | 522.86 | 51 mg yellow oil |
| 109 | | 0.94 | 509.14 | 35 mg yellow oil |

-continued

| Ex. No. | R | LC-MS | | Amount Form |
|---|---|---|---|---|
| | | $t_R$ [min] | [M + H]⁺ | |
| 110 | ~~~N(H)~~~COOH | 0.68 | 483.00 | 2 mg yellow wax |

Example 103

¹H NMR (CDCl₃): δ 1.25 (t, J=7.0 Hz, 6H), 1.32 (t, J=7.5 Hz, 3H), 2.39 (s, 3H), 2.46 (s, 3H), 2.76 (q, J=7.5 Hz, 2H), 2.93 (m, 2H), 3.09 (t, J=5.0 Hz, 2H), 3.75 (m, 6H), 3.96 (t, J=5.3 Hz, 2H), 7.22 (s, 1H), 7.87 (s, 1H), 7.88 (s, 1H).

Example 105

¹H NMR (CDCl₃): δ 1.24 (t, J=7.0 Hz, 6H), 1.30 (t, J=7.8 Hz, 3H), 2.37 (s, 3H), 2.45 (s, 3H), 2.72 (m, 2H), 3.25 (s, 2H), 3.39 (m, 1H), 3.74 (q, J=6.8 Hz, 4H), 3.98 (m, 4H), 4.13 (m, 2H), 7.20 (s, 1H), 7.83 (s, 1H), 7.85 (s, 1H).

Examples 111 to 113

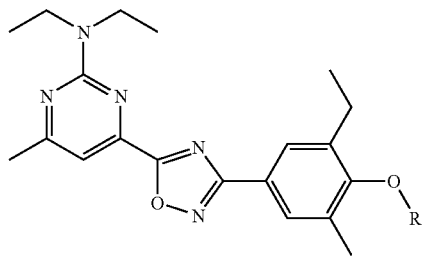

Examples 111 to 113 are prepared from Example 102 according to the general method described below:

a) A solution of methanesulfonic acid 2-{4-[5-(2-diethylamino-6-methyl-pyrimidin-4-yl)-[1,2,4]oxadiazol-3-yl]-2-ethyl-6-methyl-phenoxy}-ethyl ester (850 mg, 1.74 mmol), derived from Example 102, in 7M NH₃ in MeOH (20 mL) is stirred at 60° C. for 18 h. Volatiles are then evaporated and the residue is purified by CC (eluting with EA/MeOH 10:1) to give (4-{3-[4-(2-amino-ethoxy)-3-ethyl-5-methyl-phenyl]-[1,2,4]oxadiazol-5-yl}-6-methyl-pyrimidin-2-yl)-diethylamine as a yellow solid (700 mg); LC-MS: $t_R$=0.92 min; [M+H]⁺=410.95.

b) The above amino intermediate (1 eq.) is coupled to the appropriate carboxylic acid derivatives (1.2 eq.: glycolic acid or Boc-glycine or Boc-β-alanine) under standard conditions described before using DMF as solvent and EDC (1.5 eq.) and HOBt (1.5 eq.) as coupling agents. Completion of the reaction is monitored by LC-MS.

c) Examples 112 and 113 are obtained after a standard Boc cleavage in DCM using TFA.

| Ex. No. | R | LC-MS | | Amount Form |
|---|---|---|---|---|
| | | $t_R$ [min] | [M + H]⁺ | |
| 111 | ~~~N(H)C(O)CH₂OH | 1.10 | 469.11 | 21 mg yellow oil |
| 112 | ~~~N(H)C(O)CH₂NH₂ | 0.91 | 468.12 | 26 mg yellow solid |
| 113 | ~~~N(H)C(O)CH₂CH₂NH₂ | 0.91 | 482.09 | 10 mg yellow solid |

Example 111

¹H NMR (CDCl₃): δ 1.25 (t, J=7.0 Hz, 6H), 1.32 (t, J=7.5 Hz, 3H), 2.38 (s, 3H), 2.43 (m, 1H), 2.47 (s, 3H), 2.75 (m, 2H), 3.77 (m, 6H), 3.97 (t, J=4.8 Hz, 2H), 4.23 (d, J=2.0 Hz, 2H), 7.04 (m, 1H), 7.23 (s, 1H), 7.88 (s, 1H), 7.89 (s, 1H).

Example 114

N-(2-{4-[5-(2-Diethylamino-6-methyl-pyrimidin-4-yl)-[1,2,4]oxadiazol-3-yl]-2-ethyl-6-methyl-phenoxy}-ethyl)-N',N'-dimethyl-sulfamic acid amide To a solution of 4-{3-[4-(2-amino-ethoxy)-3-ethyl-5-methyl-phenyl]-[1,2,4]oxadiazol-5-yl}-6-methyl-pyrimidin-2-yl)-diethyl-amine (50 mg, 0.122 mmol) in DCM (5 mL) is added DIPEA (25 μL, 0.146 mmol) followed by N,N-dimethylsulfamoyl chloride (28 μL, 0.268 mmol). The reaction mixture is stirred at 40° C. for 18 h, is then evaporated and purified by prep. HPLC to give the title compound (13 mg); LC-MS: $t_R$=1.2 min; [M+H]⁺=518.13.

Examples 115 to 126

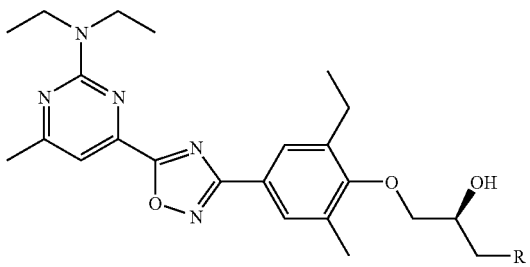

Examples 115 to 126 are prepared from Intermediate 12 following the general method described below:

a) To a solution of Intermediate 12 (1 eq.) in MeOH or DMF, the appropriate nucleophile is added (5 eq.: methanoate, or methylamine, or ethanolamine, or ethylsulfonamide, or amino acid carboxylic esters). The reaction mixture is stirred at 80° C. for 1 day (completion of the reaction is monitored by LC-MS), then diluted with DCM. The org. solution is washed with sat aq. NaHCO₃, followed by brine, dried over MgSO₄, filtered and evaporated to give the crude compound which is purified by standard method such as prep. HPLC or prep. TLC.

b) The esters 118, 120, 122 and 125 are hydrolyzed using 2M aq. LiOH in MeOH to give the Examples 119, 121, 123 and 126.

| Ex. No. | R | LC-MS $t_R$ [min] | [M + H]⁺ | Amount Form |
|---|---|---|---|---|
| 115 | OMe | 1.17 | 456.11 | 31 mg yellow oil |
| 116 | NHMe | 0.92 | 455.15 | 6.5 mg yellow oil |
| 117 | ----NH-S(O)₂-Et | 1.11 | 533.13 | 20 mg yellow oil |
| 118 | ----N(azetidine)-C(O)-OMe | 0.97 | 538.83 | 135 mg yellow oil |
| 119 | ----N(azetidine)-C(O)-OH | 0.92 | 525.2 | 22 mg yellow oil |
| 120 | MeO₂C-pyrrolidinyl | 0.97 | 553.21 | 143 mg yellow oil |
| 121 | HO₂C-pyrrolidinyl | 0.97 | 538.83 | 42 mg yellow oil |
| 122 | 3-CO₂Me-pyrrolidinyl | 0.96 | 553.20 | 145 mg yellow oil |
| 123 | 3-CO₂H-pyrrolidinyl | 0.93 | 538.74 | 88 mg yellow solid |
| 124 | ----NH-CH₂CH₂-OH | 0.89 | 485.15 | 19 mg yellow oil |
| 125 | ----NH-CH₂CH₂-OH (ethyl ester) | 0.95 | 527.18 | 57 mg yellow oil |
| 126 | ----NH-CH₂CH₂-C(O)-OH | 0.90 | 513.15 | 19 mg yellow solid |

Example 115

¹H NMR (CDCl₃): δ 1.26 (t, J=7.0 Hz, 6H), 1.32 (t, J=7.5 Hz, 3H), 2.40 (s, 3H), 2.47 (s, 3H), 2.59 (d, J=4.0 Hz, 1H), 2.77 (q, J=7.3 Hz, 2H), 3.47 (s, 3H), 3.66 (m, 2H), 3.76 (q, J=6.5 Hz, 4H), 3.92 (d, J=5.3 Hz, 2H), 4.23 (m, 1H), 7.23 (s, 1H), 7.88 (s, 1H), 7.89 (s, 1H).

Example 117

¹H NMR (CDCl₃): δ 1.26 (t, J=7.0 Hz, 6H), 1.33 (t, J=7.5 Hz, 3H), 1.44 (t, J=7.3 Hz, 3H), 2.39 (s, 3H), 2.48 (s, 3H), 2.75 (m, 2H), 3.14 (q, J=7.5 Hz, 2H), 3.35 (m, 1H), 3.50 (m, 1H), 3.76 (q, J=7.0 Hz, 4H), 3.91 (m, 2H), 4.24 (m, 1H), 4.78 (m, 1H), 7.23 (s, 1H), 7.89 (s, 1H), 7.90 (s, 1H).

Example 124

¹H NMR (CDCl₃): δ 1.25 (t, J=6.8 Hz, 6H), 1.31 (t, J=7.3 Hz, 3H), 2.38 (m, 4H), 2.46 (s, 3H), 2.74 (m, 2H), 3.06 (m,

2H), 3.11 (m, 1H), 3.75 (q, J=6.8 Hz, 4H), 3.86 (t, J=4.5 Hz, 2H), 3.90 (d, J=4.5 Hz, 2H), 4.33 (m, 1H), 7.22 (s, 1H), 7.86 (s, 1H), 7.88 (s, 1H).

Example 127

N-(2-{4-[5-(2-Diethylamino-6-methyl-pyrimidin-4-yl)-[1,2,4]oxadiazol-3-yl]-phenyl}-ethyl)-2-hydroxy-acetamide To a solution of glycolic acid (33 mg, 0.43 mmol) and DIPEA (146 μL, 0.85 mmol) in DMF (5 mL) is added EDC (82 mg, 0.43 mmol) followed by HOBt (58 mg, 0.43 mmol). The reaction mixture is stirred at rt for 10 min before adding Intermediate 12 (100 mg, 0.28 mmol). Stirring is continued for 18 h and the reaction mixture is then diluted with EtOAc, washed with sat. aq. NaHCO$_3$, dried over MgSO$_4$, filtered and evaporated. The residue is purified by prep. TLC (eluting with DCM/7M NH$_3$ in MeOH 10:1) to give the title compound (50 mg) as a yellow solid; $t_R$=1.05 min; [M+H]$^+$=411.75.

Example 128

N-(2-{4-[5-(2-Diethylamino-6-methyl-pyrimidin-4-yl)-[1,2,4]oxadiazol-3-yl]-phenyl}-ethyl)-methane-sulfonamide To a solution of Intermediate 12 (100 mg, 0.28 mmol) and DIPEA (97 μL, 0.57 mmol) in DCM (2 mL) at 0° C. is added dropwise a solution of methanesulfonyl chloride (33 μL, 0.43 mmol) in DCM (2 mL). The reaction mixture is stirred at rt for 1 h and is then diluted with EtOAc, and washed with sat. aq. NaHCO$_3$. The org. phase is dried over MgSO$_4$, filtered, evaporated and purified by prep. TLC (eluting with Heptane/EtOAc 1:1) to give the title compound (71 mg) as a yellow solid; LC-MS: $t_R$=1.07 min; [M+H]$^+$=431.07.

Example 129

N-(2-{4-[5-(2-Diethylamino-6-methyl-pyrimidin-4-yl)-[1,2,4]oxadiazol-3-yl]-phenyl}-ethyl)-N',N'-dimethyl-sulfamic acid amide Example 129 is prepared in analogy to Example 128 using N,N-dimethylsulfamoylchloride; LC-MS: $t_R$=1.12 min; [M+H]$^+$=460.01.

Examples 130 to 133

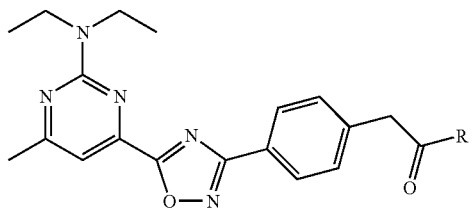

Examples 130 to 133 are prepared by coupling Intermediate 15 with the appropriate amino carboxylic esters or amine following the procedure described below.

To a suspension of {4-[5-(2-diethylamino-6-methyl-pyrimidin-4-yl)-[1,2,4]oxadiazol-3-yl]-phenyl}-acetic acid (Intermediate 15) in DMF are added TBTU (1.5 eq.) and DIPEA (3 eq.). The resulting solution is stirred for 5 min before adding the appropriate amine or amino carboxylic ester. The completion of the reaction is monitored by LC-MS. The reaction mixture is then diluted with EtOAc, washed with sat. aq. NaHCO$_3$, dried, filtered, concentrated and purified by prep. TLC.

The amino acid derivatives 131, 132 and 133 are prepared by hydrolysis of their corresponding amino carboxylic methyl esters using 20-30 eq. of 2M aq. LiOH in MeOH.

| Ex. No. | R | LC-MS $t_R$ [min] | [M + H]$^+$ | Amount Form |
|---|---|---|---|---|
| 130 | ![] | 1.07 | 395.09 | 35 mg yellow solid |
| 131 | ![] | 0.98 | 450.91 | 5 mg yellow solid |
| 132 | ![] | 1.02 | 465.01 | 47 mg yellow solid |
| 133 | ![] | 1.01 | 465.05 | 28 mg yellow oil |

Example 130

$^1$H NMR (CDCl$_3$): δ 1.11 (t, J=7.3 Hz, 3H), 1.26 (t, J=6.8 Hz, 6H), 2.48 (s, 3H), 3.30 (m, 2H), 3.65 (m, 2H), 3.77 (m, 4H), 5.36 (m, 1H), 7.22 (s, 1H), 7.43 (s, 1H), 7.45 (s, 1H), 8.18 (s, 1H), 8.20 (s, 1H).

Examples 134 to 140

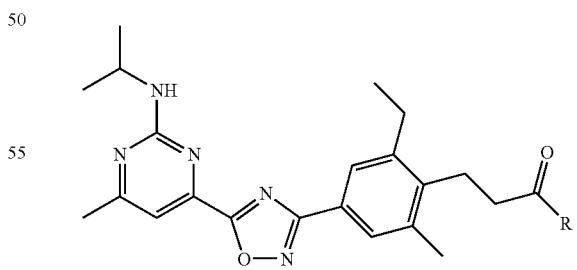

Examples 134 to 140 are prepared by coupling 3-{2-ethyl-4-[5-(2-isopropylamino-6-methyl-pyrimidin-4-yl)-[1,2,4]oxadiazol-3-yl]-6-methyl-phenyl}-propionic acid (Intermediate 10) with the appropriate amino carboxylic esters or aminoalcohols following the procedure described for Examples 130-133.

| Ex. No. | R | LC-MS $t_R$ [min] | [M + H]$^+$ | Amount Form |
|---|---|---|---|---|
| 134 | (H-N-CH2CH2-COOH) | 0.97 | 481.08 | 49 mg yellow solid |
| 135 | (azetidine-3-carboxylic acid, N-linked) | 0.97 | 493.11 | 10 mg yellow solid |
| 136 | (proline, N-linked, HO2C-) | 1.01 | 506.76 | 39 mg colorless wax |
| 137 | (pyrrolidine-3-carboxylic acid, N-linked) | 0.99 | 506.79 | 38 mg yellow solid |
| 138 | (H-N-CH2CH2-OH) | 0.96 | 453.15 | 54 mg white solid |
| 139 | (H-N-CH(CH2OH)2) | 0.91 | 482.90 | 60 mg white solid |
| 140 | (H-N-CH2-CH(OH)-CH2OH) | 0.91 | 482.93 | 68 mg white solid |

Example 137

$^1$H NMR (CDCl$_3$): δ 1.30 (m, 9H), 2.20 (m, 1H), 2.27 (m, 1H), 2.44 (d, J=2.0 Hz, 4H), 2.48 (m, 4H), 2.76 (qd, J=7.5, 1.5 Hz, 2H), 3.13 (m, 3H), 3.40 (m, 1H), 3.55 (m, 2H), 3.71 (m, 1H), 3.82 (m, 1H), 4.32 (m, 1H), 7.27 (s, 1H), 7.84 (s, 1H), 7.86 (s, 1H).

Example 139

$^1$H NMR (CDCl$_3$): δ 1.31 (m, 9H), 2.43 (m, 5H), 2.50 (s, 3H), 2.77 (m, 3H), 2.93 (s br, 1H), 3.10 (m, 2H), 3.45 (m, 2H), 3.58 (m, 2H), 3.79 (m, 1H), 4.32 (m, 1H), 5.28 (m, 1H), 5.88 (m, 1H), 7.31 (s, 1H), 7.86 (s, 1H), 7.88 (s, 1H).

Example 141

N-(2-amino-ethyl)-3-{2-ethyl-4-[5-(2-isopropylamino-6-methyl-pyrimidin-4-yl)-[1,2,4]oxadiazol-3-yl]-6-methyl-phenyl}-propionamide dihydrochloride To a suspension of Intermediate 10 (25 mg, 0.061 mmol) in DMF is added DIPEA (16 μL, 0.092 mmol) followed by TBTU (23.5 mg, 0.073 mmol). The reaction mixture is stirred for 5 min before adding N-Boc-ethylenediamine (12 μL, 0.073 mmol) and stirring is continued for 2 h. The reaction mixture is diluted with EtOAc (20 mL) and is washed with sat. aq. NaHCO$_3$ (15 mL). The org. phase is then dried over Na$_2$SO$_4$, filtered, and evaporated to give a yellow oil that is purified by prep. TLC (eluting with DCM/MeOH 95:5) to afford [2-(3-{2-ethyl-4-[5-(2-isopropylamino-6-methyl-pyrimidin-4-yl)-[1,2,4]oxadiazol-3-yl]-6-methyl-phenyl}-propionylamino)-ethyl]-carbamic acid tert-butyl ester (27 mg) as a white solid; LC-MS: $t_R$=1.09 min; [M+1]$^+$=552.30.

The above intermediate (23 mg, 0.042 mmol) is then dissolved in dioxane (0.5 mL) and 0.5 mL of 4N HCl in dioxane is added. The reaction mixture is stirred for 1.5 h and is evaporated to give a yellow solid which is sonicated in Et$_2$O (2 mL), filtered and dried to give 20 mg of N-(2-amino-ethyl)-3-{2-ethyl-4-[5-(2-isopropylamino-6-methyl-pyrimidin-4-yl)-[1,2,4]oxadiazol-3-yl]-6-methyl-phenyl}-propionamide dihydrochloride as a white solid; LC-MS: $t_R$=0.84 min; [M+H]$^+$=452.17.

Example 142

Reference Example rac-1-{4-[5-(2-Isopropylamino-6-methyl-pyrimidin-4-yl)-[1,2,4]oxadiazol-3-yl]-phenyl}-ethane-1,2-diol To a solution of isopropyl-{4-methyl-6-[3-(4-vinyl-phenyl)-[1,2,4]oxadiazol-5-yl]-pyrimidin-2-yl}-amine (Intermediate 8: 2.78 g, 8.67 mmol) in acetone (45 mL) are added water (4 mL) and a 2.5% aq. solution of OsO$_4$ (136 μL), followed by N-methyl-morpholine-N-oxide monohydrate (1.4 g, 10.4 mmol). The reaction mixture is stirred at rt for 18 h. Another 68 μL of 2.5% aq. solution of OsO$_4$ is added and stirring is continued for another 3 h. The mixture is then diluted with DCM (150 mL), and washed with water (3×50 mL), dried over MgSO$_4$, filtered and evaporated to give 0.97 g of racemic 1-{4-[5-(2-isopropylamino-6-methyl-pyrimidin-4-yl)-[1,2,4]oxadiazol-3-yl]-phenyl}-ethane-1,2-diol as a brown solid; LC-MS: $t_R$=0.84 min; [M+H]$^+$=356.04. $^1$H NMR (CDCl$_3$) δ 1.30 (d, J=6.5 Hz, 6H), 2.16 (s br, 1H), 2.49 (s, 3H), 2.74 (s br, 1H), 3.72 (dd, J=11.0, 8.0 Hz, 1H), 3.86 (dd, J=11.0, 3.3 Hz, 0H), 4.31 (m, 1H), 4.94 (dd, J=7.8, 3.3 Hz, 1H), 5.28 (s br, 1H), 7.30 (s, 1H), 7.55 (d, J=8.3 Hz, 2H), 8.20 (d, J=8.3 Hz, 2H).

Example 143 rac-2-(2-Hydroxy-ethylamino)-1-{4-[5-(2-isopropylamino-6-methyl-pyrimidin-4-yl)-[1,2,4]oxadiazol-3-yl]-phenyl}-ethanol a) A solution of Example 142 (868 mg, 2.44 mmol) and DIPEA (0.84 mL, 4.88 mmol) in THF (30 mL) is cooled down to −5° C. before adding a solution of methanesulfonyl chloride (152 μL, 1.95 mmol) in THF (1 mL). The reaction mixture is stirred at −5° C. for 1 h, then at rt for another hour. After dilution with DCM (250 mL) the org. solution is washed with sat. aq. NaHCO$_3$ (3×50 mL), dried over MgSO$_4$, filtered and evaporated to give the crude methanesulfonic acid 2-hydroxy-2-{4-[5-(2-isopropylamino-6-methyl-pyrimidin-4-yl)-[1,2,4]oxadiazol-3-yl]-phenyl}-ethyl ester as a grey oil (1.28 g); LC-MS: $t_R$=0.95 min; [M+H]$^+$=443.95.

b) Ethanolamine (3.0 mL, 49.85 mmol) is added to a solution of methanesulfonic acid 2-hydroxy-2-{4-[5-(2-isopropylamino-6-methyl-pyrimidin-4-yl)-[1,2,4]oxadiazol-3-yl]-phenyl}-ethyl ester (152 mg, 0.35 mmol) in dioxane (2.0 mL). The reaction mixture is stirred at 80° C. for 18 h, is then evaporated and purified by prep. TLC (eluting with DCM/MeOH 10:1) to give 99 mg of the title compound as a yellow oil; LC-MS: $t_R$=0.74 min; [M+H]$^+$=399.07. $^1$H NMR (CDCl$_3$) δ 1.29 (d, J=6.5 Hz, 6H), 2.48 (s, 3H), 2.84 (m, 3H), 2.97 (dd, J=12.3, 3.5 Hz, 1H), 3.73 (t, J=5.0 Hz, 1H), 4.31 (m, 1H), 4.85 (dd, J=8.8, 3.3 Hz, 1H), 5.30 (s br, 1H), 7.29 (s, 1H), 7.53 (d, J=8.3 Hz, 2H), 8.17 (d, J=8.0 Hz, 2H).

Example 144 rac-2-Amino-1-{4-[5-(2-isopropylamino-6-methyl-pyrimidin-4-yl)-[1,2,4]oxadiazol-3-yl]-phenyl}-ethanol A solution of 7M NH$_3$ in methanol (35 mL) is added to methanesulfonic acid 2-hydroxy-2-{4-[5-(2-isopropylamino-6-methyl-pyrimidin-4-yl)-[1,2,4]oxadiazol-3-yl]-phenyl}-ethyl ester (606 mg, 1.40 mmol, synthesis described for Example 143). The reaction mixture is stirred at 65° C. for 18 h and is then evaporated to give 293 mg of rac-2-amino-1-{4-[5-(2-isopropylamino-6-methyl-pyrimidin-4-yl)-[1,2,4]oxadiazol-3-yl]-phenyl}-ethanol as a yellow oil; LC-MS: t$_R$=0.73 min; [M+H]$^+$=355.06.

Example 145 rac-N-(2-Hydroxy-2-{4-[5-(2-isopropylamino-6-methyl-pyrimidin-4-yl)-[1,2,4]oxadiazol-3-yl]-phenyl}-ethyl)-methanesulfonamide To a solution of rac-2-amino-1-{4-[5-(2-isopropylamino-6-methyl-pyrimidin-4-yl)-[1,2,4]oxadiazol-3-yl]-phenyl}-ethanol (39 mg, 0.11 mmol) and DIPEA (30 μL, 0.176 mmol) in DCM (6 mL) at 0° C. is added dropwise a solution of mesylchloride (10 μL, 0.132 mmol) in DCM (2 mL). The reaction mixture is stirred at 0° C. for 1 h, and then at rt for another hour. The reaction mixture is evaporated and purified by prep. TLC eluting with DCM/7M NH$_3$ in MeOH 10:1 to give rac-N-(2-hydroxy-2-{4-[5-(2-isopropylamino-6-methyl-pyrimidin-4-yl)-[1,2,4]oxadiazol-3-yl]-phenyl}-ethyl)-methanesulfonamide (19 mg) as a white solid; t$_R$=0.89 min; [M+H]$^+$=432.99.

Example 146 rac-N-(2-Hydroxy-2-{4-[5-(2-isopropylamino-6-methyl-pyrimidin-4-yl)-[1,2,4]oxadiazol-3-yl]-phenyl}-ethyl)-N',N'-dimethyl-sulfamic acid amide Example 146 is prepared in analogy to Example 145 using dimethylsulfamoyl chloride; LC-MS: t$_R$=0.94 min; [M+H]$^+$=461.99.

Example 147 rac-2-Hydroxy-N-(2-hydroxy-2-{4-[5-(2-isopropylamino-6-methyl-pyrimidin-4-yl)-[1,2,4]oxadiazol-3-yl]-phenyl}-ethyl)-acetamide The title compound is prepared in analogy to Example 127 using rac-2-amino-1-{4-[5-(2-isopropylamino-6-methyl-pyrimidin-4-yl)-[1,2,4]oxadiazol-3-yl]-phenyl}-ethanol (Example 144) and glycolic acid; LC-MS: t$_R$=0.81 min; [M+H]$^+$=413.03.

Example 148 rac-2-Amino-N-(2-hydroxy-2-{4-[5-(2-isopropylamino-6-methyl-pyrimidin-4-yl)-[1,2,4]oxadiazol-3-yl]-phenyl}-ethyl)-acetamide Example 148 is prepared in analogy to Example 147 using Boc-glycine followed by standard Boc cleavage using TFA in DCM; LC-MS: t$_R$=0.73 min; [M+H]$^+$=412.07.

Example 149 rac-3-{4-[5-(2-Isopropylamino-6-methyl-pyrimidin-4-yl)-[1,2,4]oxadiazol-3-yl]-phenyl}-propane-1,2-diol Example 149 is prepared in analogy to Example 142 using 3-(4-cyanophenyl)-1-propene (Intermediate 9); LC-MS: t$_R$=0.73 min; [M+H]$^+$=412.07; $^1$H NMR (MeOH-D$_4$) δ 1.29 (d, J=6.5 Hz, 6H), 2.47 (s, 3H), 2.78 (dd, J=13.6, 7.8 Hz, 1H), 2.97 (dd, J=13.6, 5.0 Hz, 1H), 3.54 (m, 2H), 3.89 (m, 1H), 4.30 (m, 1H), 7.33 (s, 1H), 7.47 (d, J=8.3 Hz, 2H), 8.09 (d, J=8.3 Hz, 2H).

Examples 150 to 155

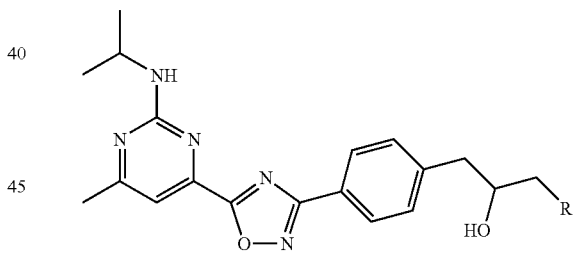

The following Examples are prepared starting from Example 149 in analogy to previous Examples 143-148.

| Ex. No. | prepared in analogy to Example | R | LC-MS t$_R$ [min] | [M + H]$^+$ | Amount | Form |
|---|---|---|---|---|---|---|
| 150 | 145 | ·····N(H)-S(=O)$_2$-CH$_3$ | 0.91 | 446.92 | 123 mg | beige solid |
| 151 | 146 | ·····N(H)-S(=O)$_2$-N(CH$_3$)$_2$ | 0.96 | 476.01 | 129 mg | white solid |

-continued

| Ex. No. | prepared in analogy to Example | R | LC-MS $t_R$ [min] | [M + H]$^+$ | Amount Form |
|---|---|---|---|---|---|
| 152 | 147 | ⋯N(H)–C(=O)–CH$_2$–OH | 0.83 | 426.88 | 109 mg beige solid |
| 153 | 148 | ⋯N(H)–C(=O)–CH$_2$–NH$_2$ | 0.76 | 425.99 | 115 mg white solid |
| 154 | 143 | ⋯N(H)–CH$_2$–CH$_2$–OH | 0.77 | 412.96 | 98 mg yellow solid |
| 155 | 144 | ⋯NH$_2$ | 0.76 | 369.06 | 1.15 g white solid |

Example 156

(S)-3-{2-Ethyl-4-[5-(2-isopropylamino-6-methyl-pyrimidin-4-yl)-oxazol-2-yl]-6-methyl-phenoxy}-propane-1,2-diol a) To a solution of 2-isopropylamino-6-methyl-pyrimidine-4-carboxylic acid (2.0 g, 10.2 mmol) in DCM (45 mL), DIPEA (8.8 mL, 51.2 mmol) followed by TBTU (3.9 g, 12.3 mmol) is added. The mixture is stirred at rt for 30 min before N,O-dimethylhydroxylamine (1.20 g, 12.3 mmol) is added. The mixture is stirred at rt for 18 h before it is diluted with DCM, washed with sat. aq. NaHCO$_3$, followed by water, dried over MgSO$_4$, filtered and concentrated. The crude product is purified by CC on silica gel eluting with heptane:EA 1:2 to give 2-isopropylamino-6-methyl-pyrimidine-4-carboxylic acid methoxy-methyl-amide (2.39 g) as a yellow oil; LC-MS: $t_R$=0.66 min, [M+H]$^+$=239.03; $^1$H NMR (D$_6$-DMSO): δ 1.14 (d, J=6.5 Hz, 6H), 2.28 (s, 3H), 3.23 (s, 3H), 3.67 (s, 3H), 4.05 (m, 1H), 6.50 (s br, 1H), 7.12 (s br, 1H).

b) To a solution of 2-isopropylamino-6-methyl-pyrimidine-4-carboxylic acid methoxy-methyl-amide (2.39 g, 10.0 mmol) in THF (50 mL), methyl magnesium bromide (7.0 mL of a 3 M solution in ether, 20.1 mmol) is added dropwise at 5° C. The mixture is stirred at 5° C. for 1.5 h. The reaction is quenched by adding NH$_4$Cl. The mixture is diluted with EtOAc (75 mL), washed with sat. aq. NaHCO$_3$, dried over Na$_2$SO$_4$, filtered and concentrated to give 1-(2-isopropylamino-6-methyl-pyrimidin-4-yl)-ethanone (1.71 g) as a yellow solid. LC-MS: $t_R$=0.75 min, [M+H]$^+$=194.01; $^1$H NMR (CDCl$_3$): δ 1.29 (d, J=6.5 Hz, 6H), 2.41 (s, 3H), 2.62 (s, 3H), 4.22 (m, 1H), 5.02 (m, 1H), 6.97 (s, 1H).

c) A solution of hydroxylamine hydrochloride (737 mg, 10.6 mmol) in water (3.0 mL) and 1 N aq. NaOH (11 mL) is added to 1-(2-isopropylamino-6-methyl-pyrimidin-4-yl)-ethanone (1.71 g, 8.85 mmol). The solution is stirred at 80° C. for 2 h and MeOH is added to maintain homogeneity of the mixture. The mixture is cooled to rt and the precipitate that forms is collected, washed with water and dried in vacuo to give 1-(2-isopropylamino-6-methyl-pyrimidin-4-yl)-ethanone oxime (1.54 g) as a yellow solid; LC-MS: $t_R$=0.72 min, [M+H]$^+$=209.52; $^1$H NMR (D$_6$-DMSO): δ 1.15 (d, J=6.5 Hz, 6H), 2.10 (s, 3H), 2.25 (s, 3H), 4.07 (m, 1H), 6.80 (s, 1H), 6.86 (d, J=7.5 Hz, 1H), 11.62 (s, 1H).

d) To a solution of 1-(2-isopropylamino-6-methyl-pyrimidin-4-yl)-ethanone oxime (920 mg, 4.42 mmol) in pyridine (5 mL), p-toluenesulfonyl chloride (1.43 g, 7.5 mmol) is added at 5° C. The mixture is stirred at 5° C. for 24 h. The solvent is evaporated and the remaining residue is partioned between water (40 mL) and EtOAc (100 mL). The org. phase is separated, washed with water, dried over MgSO$_4$, filtered and concentrated. The crude product is purified by CC on silica gel eluting with heptane:EA 0:1 to 1:1 to give 1-(2-isopropylamino-6-methyl-pyrimidin-4-yl)-ethanone oxime p-toluenesulfonic ester (1.46 g) as a pale brown solid; LC-MS: $t_R$=0.99 min, [M+H]$^+$=363.0.

e) A solution of potassium ethanolate (24% in water, 0.18 mL) is added to a solution of 1-(2-isopropylamino-6-methyl-pyrimidin-4-yl)-ethanone oxime p-toluenesulfonic ester (300 mg, 0.83 mmol) in ethanol (1.5 mL) at 5° C. The mixture is stirred at rt for 2 h. The mixture is diluted with ether and stirred for 30 min before it is filtered through celite. The filtrate is concentrated and dissolved in ether (20 mL). 2 N aq. HCl (10 mL) is added and the mixture is stirred at rt for 1 h. The org. phase is separated and extracted with 2 N aq. HCl (10 mL). The aq. extracts are combined and concentrated at 30° C. to give crude [4-(2-amino-1,1-diethoxy-ethyl)-6-methyl-pyrimidin-2-yl]-isopropyl-amine dihydrochloride (174 mg) as a yellow oil; LC-MS: $t_R$=0.85 min, [M+H]$^+$=283.03.

f) To a solution of 4-benzyloxy-3-ethyl-5-methyl-benzoic acid (224 mg, 0.83 mmol) in DMF (5 mL), EDC (175 mg, 0.91 mmol) and HOBt (124 mg, 0.91 mmol) are added. The mixture is stirred at rt for 15 min before DIPEA (0.57 mL, 3.3 mmol) and a solution of crude [4-(2-amino-1,1-diethoxy-ethyl)-6-methyl-pyrimidin-2-yl]-isopropyl-amine dihydrochloride (174 mg, 0.83 mmol) in DMF (2.0 mL) is added. The mixture is stirred at rt for 4 h, diluted with EtOAc (30 mL), and washed with sat. aq. NaHCO$_3$ (15 mL) and brine (15 mL). The org. extract is dried over Na$_2$SO$_4$, filtered and concentrated. The crude product is purified on prep. TLC plates with Heptane/EtOAc 1:1 to give 4-benzyloxy-N-[2,2-diethoxy-2-(2-isopropylamino-6-methyl-pyrimidin-4-yl)-ethyl]-3-ethyl-5-methyl-benzamide (348 mg) as a yellow oil; LC-MS: $t_R$=1.02 min, [M+H]$^+$=535.22.

g) To a solution of 4-benzyloxy-N-[2,2-diethoxy-2-(2-isopropylamino-6-methyl-pyrimidin-4-yl)-ethyl]-3-ethyl-5-methyl-benzamide (346 mg, 0.65 mmol) in THF (8 mL), 25% aq. HCl (500 μL) is added and the mixture is stirred at 65° C. for 18 h. The mixture is cooled to 0° C., neutralized by adding 1 N aq. NaOH solution and extracted twice with EtOAc. The combined org. extracts are dried over $Na_2SO_4$, filtered and concentrated to give crude 4-benzyloxy-3-ethyl-N-[2-(2-isopropylamino-6-methyl-pyrimidin-4-yl)-2-oxo-ethyl]-5-methyl-benzamide (325 mg) as a yellow oil; LC-MS: $t_R$=0.94 min, $[M+H]^+$=461.13.

h) To a solution of crude 4-benzyloxy-3-ethyl-N-[2-(2-isopropylamino-6-methyl-pyrimidin-4-yl)-2-oxo-ethyl]-5-methyl-benzamide (300 mg, 0.65 mmol) in THF (10 mL), Burgess reagent (775 mg, 3.3 mmol) is added. The mixture is stirred at 80° C. for 18 h before it is concentrated. The crude product is purified on prep. TLC plates with Heptane/EA 1:1 to give {4-[2-(4-benzyloxy-3-ethyl-5-methyl-phenyl)-oxazol-5-yl]-6-methyl-pyrimidin-2-yl}-isopropyl-amine (27 mg) as a yellow solid; LC-MS: $t_R$=1.05 min, $[M+H]^+$=442.81.

i) To a solution of {4-[2-(4-benzyloxy-3-ethyl-5-methyl-phenyl)-oxazol-5-yl]-6-methyl-pyrimidin-2-yl}-isopropyl-amine (27 mg, 61 μmol) in THF (2 mL) and MeOH (2 mL), 10% Pd/C is added (50 mg). The reaction mixture is stirred under $H_2$ atmosphere for 18 h, and is filtered through celite. The filtrate is evaporated to give 2-ethyl-4-[5-(2-isopropylamino-6-methyl-pyrimidin-4-yl)-oxazol-2-yl]-6-methyl-phenol (21 mg) as a yellow oil; LC-MS: $t_R$=0.88 min, $[M+H]^+$=353.03.

j) To a solution of 2-ethyl-4-[5-(2-isopropylamino-6-methyl-pyrimidin-4-yl)-oxazol-2-yl]-6-methyl-phenol (30 mg, 85 μmol) in iPrOH (4 mL), 3M aq. NaOH (1 mL) followed by (S)-3-chloro-propane-1,2-diol (67 μL, 0.85 mmol) is added. The reaction mixture is stirred at rt for 15 h, and is then diluted with EtOAc and washed with 1M aq. NaOH followed by brine. The org. solution is dried over $Na_2SO_4$, filtered and evaporated to give 3-{2-ethyl-4-[5-(2-isopropylamino-6-methyl-pyrimidin-4-yl)-oxazol-2-yl]-6-methyl-phenoxy}-propane-1,2-diol (9 mg) as a yellow solid; LC-MS: $t_R$=0.79 min, $[M+H]^+$=426.80.

Example 157

GTPγS assay to determine $EC_{50}$ values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM $MgCl_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

The compound of Example 132 showed $EC_{50}$ values above 10 μM. $EC_{50}$ values of all other exemplified compounds are in the range of 0.17 to 9360 nM with an average of 260 nM. Agonistic activities of some compounds of formula (I), determined according to the method described above, are displayed in Table 1.

TABLE 1

| Compound of Example | $EC_{50}$ [nM] |
| --- | --- |
| 1 | 1.15 |
| 2 | 1.20 |
| 4 | 0.46 |
| 7 | 0.88 |
| 14 | 26 |
| 19 | 2.27 |
| 31 | 0.17 |
| 35 | 1.37 |
| 41 | 4.5 |
| 43 | 0.97 |
| 46 | 3.7 |
| 54 | 1.0 |
| 63 | 0.25 |
| 78 | 5.8 |
| 81 | 7.4 |
| 86 | 5.7 |
| 89 | 39.4 |
| 99 | 3730 |
| 100 | 5.1 |
| 103 | 72.1 |
| 109 | 8.4 |
| 112 | 12.5 |
| 117 | 22.3 |
| 126 | 1.4 |
| 128 | 74.4 |
| 131 | 44.6 |
| 134 | 2.0 |
| 140 | 12.6 |
| 144 | 80.3 |
| 149 | 25 |
| 154 | 331 |

Example 158

Assessment of In vivo Efficacy

The efficacy of the compounds of formula (I) is assessed by measuring the circulating lymphocytes after oral administration of 3 to 30 mg/kg of a compound of formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 6 h after oral administration of 10 mg/kg of some compounds of the present invention to normotensive male Wistar rats as compared to a group of animals treated with vehicle only.

TABLE 2

| Compound of Example | Lymphocyte counts |
| --- | --- |
| 1 | −70 ± 3% |
| 3 | −70 ± 2% |
| 10 | −50 ± 2% |
| 16 | −74 ± 1% |
| 20 | −55 ± 1% |
| 29 | −73 ± 2% |
| 32 | −58 ± 2% |
| 33 | −65 ± 2% |
| 40 | −69 ± 2% |
| 51 | −61 ± 2% |
| 59 | −69 ± 2% |
| 65 | −60 ± 4% |
| 85 | −68 ± 1% |
| 138 | −74 ± 1% |

The invention claimed is:

1. A compound of the formula (I)

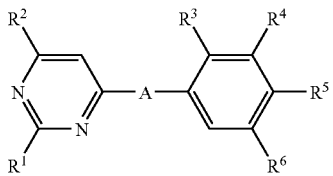

Formula (I)

wherein
A represents

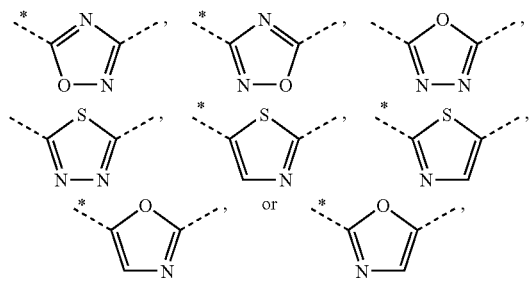

wherein the asterisks indicate the bond that is linked to the pyrimidine group of formula (I);

$R^1$ represents $C_{1-4}$-alkoxy, $C_{1-4}$-alkylamino, N—$C_{1-4}$-alkyl-N—$C_{1-3}$-alkylamino, $C_{3-5}$-cycloalkylamino, $C_{3-5}$-cycloalkylmethylamino, pyrrolidine, or piperidine;

$R^2$ represents $C_{1-2}$-alkyl or $C_{3-4}$-alkyl;

$R^3$ represents hydrogen, $C_{1-4}$-alkyl, or $C_{1-3}$-alkoxy;

$R^4$ represents hydrogen, $C_{1-4}$-alkyl, or $C_{1-3}$-alkoxy;

$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—NH-$COR^{54}$, —$CH_2$—$(CH_2)_n$—$CONR^{51}R^{52}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl] ethoxy, —$OCH_2$—$CH(OH)$—$CH_2$—$NR^{51}R^{52}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, or —$OCH_2$—$CH(OH)$—$CH_2$—$NHCOR^{54}$;

$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, ($C_{1-5}$-alkylcarboxy)methyl, 2-carboxyethyl, 2-($C_{1-5}$-alkylcarboxy)ethyl, or 2-aminoethyl;

$R^{52}$ represents hydrogen, methyl, or ethyl;

$R^{53}$ represents $C_{1-3}$-alkyl, methylamino, ethylamino, or dimethylamino;

$R^{54}$ represents hydroxy-$C_{1-2}$-alkyl or $R^{55}R^{56}N$—$C_{1-2}$-alkyl;

$R^{55}$ and $R^{56}$ independently represent hydrogen or methyl;

k represents the integer 1, 2, or 3;

m represents the integer 1 or 2;

n represents 0, 1, or 2; and $R^6$ represents hydrogen, $C_{1-4}$-alkyl, or halogen; or a salt of such a compound.

2. A compound according to claim 1, wherein A represents

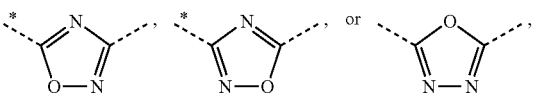

wherein the asterisks indicate the bond that is linked to the pyrimidine group of formula (I); or a salt of such a compound.

3. A compound according to claim 1, wherein A represents

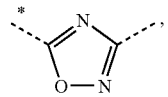

wherein the asterisk indicates the bond that is linked to the pyrimidine group of formula (I); or a salt of such a compound.

4. A compound according to claim 1, wherein $R^1$ represents $C_{1-4}$-alkylamino or N—$C_{1-4}$-alkyl-N—$C_{1-3}$-alkylamino; or a salt of such a compound.

5. A compound according to claim 1, wherein $R^1$ represents $C_{1-4}$-alkoxy; or a salt of such a compound.

6. A compound according to claim 1, wherein $R^2$ represents $C_{1-4}$-alkyl; or a salt of such a compound.

7. A compound according to claim 1, wherein $R^3$ represents hydrogen; or a salt of such a compound.

8. A compound according to claim 1, wherein $R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH$ (OH)—CH₂—NHCOR⁵⁴, —CH₂—(CH₂)ₙ—CONR⁵¹R⁵², —(CH₂)ₙCH(OH)—CH₂—NR⁵¹R⁵², hydroxy-C₂₋₅-alkoxy, di-(hydroxy-C₁₋₄-alkyl)-C₁₋₄-alkoxy, 2,3-dihydroxy-propoxy, 2-hydroxy-3-methoxy-propoxy, —OCH₂—(CH₂)ₘ—NR⁵¹R⁵², —OCH₂—CH(OH)—CH₂—NR⁵¹R⁵², —OCH₂—(CH₂)ₘ—NHSO₂R⁵³, —OCH₂—CH(OH)—CH₂—NHSO₂R⁵³, —OCH₂—(CH₂)ₘ—NHCOR⁵⁴, or —OCH₂—CH(OH)—CH₂—NHCOR⁵⁴; or a salt of such a compound.

9. A compound according to claim 1, wherein R⁵ represents 2,3-dihydroxy-propoxy or —OCH₂—CH(OH)—CH₂—NHCOR⁵⁴; or a salt of such a compound.

10. A compound according to claim 1, wherein A represents

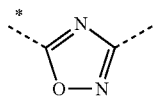

wherein the asterisk indicates the bond that is linked to the pyrimidine group of formula (I);
R¹ represents C₁₋₄ alkoxy;
R² represents C₁₋₂-alkyl or C₃₋₄-alkyl;
R³ represents hydrogen;
R⁴ represents C₁₋₄-alkyl, or C₁₋₃-alkoxy;
R⁵ represents —(CH₂)ₙCH(OH)—CH₂—NHCOR⁵⁴, —CH₂—(CH₂)ₙ—CONR⁵¹R⁵², hydroxy-C₂₋₅-alkoxy, di-(hydroxy-C₁₋₄-alkyl)-C₁₋₄-alkoxy, 2,3-dihydroxy-propoxy, —OCH₂—(CH₂)ₘ—NR⁵¹R⁵², 2-[(azetidine-3-carboxylic acid)-1-yl]-ethoxy, 2-[(pyrrolidine-3-carboxylic acid)-1-yl]-ethoxy, —OCH₂—CH(OH)—CH₂—NR⁵¹R⁵², 3-[(azetidine-3-carboxylic acid)-1-yl]-2-hydroxypropoxy, 2-hydroxy-3-[(pyrrolidine-3-carboxylic acid)-1-yl]-propoxy, 2-hydroxy-3-[(pyrrolidine-2-carboxylic acid)-1-yl]-propoxy, —OCH₂—CH(OH)—CH₂—NHSO₂R⁵³, —OCH₂—(CH₂)ₘ—NHCOR⁵⁴, or —OCH₂—CH(OH)—CH₂—NHCOR⁵⁴;
R⁵¹ represents hydrogen, C₁₋₃-alkyl, 2-hydroxyethyl, 2-hydroxy-1-hydroxymethyl-ethyl, 2,3-dihydroxypropyl, carboxymethyl, (C₁₋₅-alkylcarboxy)methyl, 2-carboxyethyl, 2-(C₁₋₅-alkylcarboxy)ethyl, or 2-aminoethyl;
R⁵² represents hydrogen, methyl, or ethyl;
R⁵³ represents C₁₋₃-alkyl, methylamino, ethylamino, or dimethylamino;
R⁵⁴ represents hydroxy-C₁₋₂-alkyl or R⁵⁵R⁵⁶N—C₁₋₂-alkyl;
R⁵⁵ and R⁵⁶ independently represent hydrogen or methyl;
m represents the integer 1 or 2;
n represents 0, 1, or 2; and
R⁶ represents hydrogen, C₁₋₄-alkyl, or halogen;
or a salt of such a compound.

11. A compound according to claim 1 selected from the group consisting of:
N-(3-{2,6-dimethyl-4-[5-(6-methyl-2-methylamino-pyrimidin-4-yl)-[1,2,4]oxadiazol-3-yl]-phenoxy}-2-hydroxy-propyl)-2-hydroxy-acetamide;
N-(3-{4-[5-(2-ethylamino-6-methyl-pyrimidin-4-yl)-[1,2,4]oxadiazol-3-yl]-2,6-dimethyl -phenoxy}-2-hydroxy-propyl)-2-hydroxy-acetamide;
N—((S)-3-{2-ethyl-4-[5-(2-ethylamino-6-methyl-pyrimidin-4-yl)-[1,2,4]oxadiazol-3-yl]-6-methyl-phenoxy}-2-hydroxy-propyl)-2-hydroxy-acetamide;
N-(3-{2,6-dimethyl-4-[5-(6-methyl-2-propylamino-pyrimidin-4-yl)-[1,2,4]oxadiazol-3-yl]-phenoxy}-2-hydroxy-propyl)-2-hydroxy-acetamide;
N-(3-{4-[5-(2-isopropylamino-6-methyl-pyrimidin-4-yl)-[1,2,4]oxadiazol-3-yl]-2,6-dimethyl -phenoxy}-2-hydroxy-propyl)-2-hydroxy-acetamide;
N—((S)-3-{2-ethyl-4-[5-(2-isobutylamino-6-methyl-pyrimidin-4-yl)-[1,2,4]oxadiazol-3-yl]-6-methyl-phenoxy}-2-hydroxy-propyl)-2-hydroxy-acetamide;
N-(3-{4-[5-(2-isobutylamino-6-methyl-pyrimidin-4-yl)-[1,2,4]oxadiazol-3-yl]-2,6-dimethyl -phenoxy}-2-hydroxy-propyl)-2-hydroxy-acetamide;
N—((S)-3-{4-[5-(2-diethylamino-6-methyl-pyrimidin-4-yl)-[1,2,4]oxadiazol-3-yl]-2-ethyl-6-methyl-phenoxy}-2-hydroxy-propyl)-2-hydroxy-acetamide;
N-(3-{4-[5-(2-diethylamino-6-methyl-pyrimidin-4-yl)-[1,2,4]oxadiazol-3-yl]-2,6-dimethyl -phenoxy}-2-hydroxy-propyl)-2-hydroxy-acetamide;
N-(3-{4-[5-(2-dimethylamino-6-methyl-pyrimidin-4-yl)-[1,2,4]oxadiazol-3-yl]-2,6-dimethyl -phenoxy}-2-hydroxy-propyl)-2-hydroxy-acetamide;
N-(3-{4-[5-(2-(ethyl-methylamino)-6-methyl-pyrimidin-4-yl)-[1,2,4]oxadiazol-3-yl]-2,6-dimethyl-phenoxy}-2-hydroxy-propyl)-2-hydroxy-acetamide;
N-(3-{4-[5-(2-isopropoxy-6-methyl-pyrimidin-4-yl)-[1,2,4]oxadiazol-3-yl]-2,6-dimethyl -phenoxy}-2-hydroxy-propyl)-2-hydroxy-acetamide;
3-{4-[5-(2-ethylamino-6-methyl-pyrimidin-4-yl)-[1,2,4]oxadiazol-3-yl]-2,6-dimethyl-phenoxy}-propane-1,2-diol;
3-{2,6-dimethyl-4-[5-(6-methyl-2-propylamino-pyrimidin-4-yl)-[1,2,4]oxadiazol-3-yl]-phenoxy}-propane-1,2-diol;
3-{4-[5-(2-isopropylamino-6-methyl-pyrimidin-4-yl)-[1,2,4]oxadiazol-3-yl]-2,6-dimethyl -phenoxy}-propane-1,2-diol;
3-{4-[5-(2-isobutylamino-6-methyl-pyrimidin-4-yl)-[1,2,4]oxadiazol-3-yl]-2,6-dimethyl -phenoxy}-propane-1,2-diol;
3-{4-[5-(2-diethylamino-6-methyl-pyrimidin-4-yl)-[1,2,4]oxadiazol-3-yl]-2,6-dimethyl -phenoxy}-propane-1,2-diol; and
3-{4-[5-(2-(ethyl-methylamino)-6-methyl-pyrimidin-4-yl)-[1,2,4]oxadiazol-3-yl]-2,6-dimethyl -phenoxy}-propane-1,2-diol;
or a salt of such a compound.

12. A compound according to claim 1 selected from the group consisting of:
N-(3-{2-ethyl-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;
N-[3-(2-ethyl-4-{5-[2-(isobutyl-methyl-amino)-6-methyl-pyrimidin-4-yl]-[1,2,4]oxadiazol-3-yl}-6-methyl-phenoxy)-2-hydroxy-propyl]-2-hydroxy-acetamide;
N-(3-{4-[5-(2-cyclopropylamino-6-methyl-pyrimidin-4-yl)-[1,2,4]oxadiazol-3-yl]-2-ethyl-6-methyl-phenoxy}-2-hydroxy-propyl)-2-hydroxy-acetamide;
N-[3-(4-{5-[2-(cyclopropylmethyl-amino)-6-methyl-pyrimidin-4-yl]-[1,2,4]oxadiazol-3-yl}-2-ethyl-6-methyl-phenoxy)-2-hydroxy-propyl]-2-hydroxy-acetamide;
N-(3-{2-ethyl-4-[5-(6-ethyl-2-ethylamino-pyrimidin-4-yl)-[1,2,4]oxadiazol-3-yl]-6-methyl -phenoxy}-2-hydroxy-propyl)-2-hydroxy-acetamide;
N-(3-{2-ethyl-6-methyl-4-[5-(2-methylamino-6-propyl-pyrimidin-4-yl)-[1,2,4]oxadiazol-3-yl]-phenoxy}-2-hydroxy-propyl)-2-hydroxy-acetamide;

N—((S)-3-{2-ethyl-4-[5-(6-isobutyl-2-methylamino-pyrimidin-4-yl)-[1,2,4]oxadiazol-3-yl]-6-methyl-phenoxy}-2-hydroxy-propyl)-2-hydroxy-acetamide;
N-(3-{2-ethyl-4-[5-(2-isopropoxy-6-methyl-pyrimidin-4-yl)-[1,2,4]oxadiazol-3-yl]-6-methyl -phenoxy}-2-hydroxy-propyl)-2-hydroxy-acetamide;
N-(3-{2-ethyl-4-[5-(2-isobutoxy-6-methyl-pyrimidin-4-yl)-[1,2,4]oxadiazol-3-yl]-6-methyl -phenoxy}-2-hydroxy-propyl)-2-hydroxy-acetamide;
N-(3-{4-[5-(2-ethoxy-6-ethyl-pyrimidin-4-yl)-[1,2,4]oxadiazol-3-yl]-2-ethyl-6-methyl -phenoxy}-2-hydroxy-propyl)-2-hydroxy-acetamide;
N-(3-{2-ethyl-4-[5-(2-methoxy-6-propyl-pyrimidin-4-yl)-[1,2,4]oxadiazol-3-yl]-6-methyl -phenoxy}-2-hydroxy-propyl)-2-hydroxy-acetamide;
N—((S)-3-{2-ethyl-4-[5-(6-isobutyl-2-methoxy-pyrimidin-4-yl)-[1,2,4]oxadiazol-3-yl]-6-methyl -phenoxy}-2-hydroxy-propyl)-2-hydroxy-acetamide;
N-(3-{2-chloro-4-[5-(2-isopropylamino-6-methyl-pyrimidin-4-yl)-[1,2,4]oxadiazol-3-yl]-6-methyl-phenoxy}-2-hydroxy-propyl)-2-hydroxy-acetamide;
2-hydroxy-N-(2-hydroxy-3-{4-[5-(2-isopropylamino-6-methyl-pyrimidin-4-yl)-[1,2,4]oxadiazol -3-yl]-2-methoxy-6-methyl-phenoxy}-propyl)-acetamide;
N-(3-{2-chloro-4-[5-(2-isopropoxy-6-methyl-pyrimidin-4-yl)-[1,2,4]oxadiazol-3-yl]-6-methyl -phenoxy}-2-hydroxy-propyl)-2-hydroxy-acetamide;
3-{2-ethyl-4-[5-(2-isopropylamino-6-methyl-pyrimidin-4-yl)-[1,2,4]oxadiazol-3-yl]-6-methyl -phenoxy}-propane-1,2-diol;
3-{2-ethyl-4-[5-(2-isobutylamino-6-methyl-pyrimidin-4-yl)-[1,2,4]oxadiazol-3-yl]-6-methyl -phenoxy}-propane-1,2-diol;
3-{4-[5-(2-cyclopropylamino-6-methyl-pyrimidin-4-yl)-[1,2,4]oxadiazol-3-yl]-2-ethyl-6-methyl -phenoxy}-propane-1,2-diol;
3-{2-ethyl-4-[5-(6-ethyl-2-ethylamino-pyrimidin-4-yl)-[1,2,4]oxadiazol-3-yl]-6-methyl -phenoxy}-propane-1,2-diol;
3-{2-ethyl-4-[5-(6-ethyl-2-ethylamino-pyrimidin-4-yl)-[1,2,4]oxadiazol-3-yl]-6-methyl -phenoxy}-propane-1,2-diol;
3-{2-ethyl-4-[5-(6-isobutyl-2-methoxy-pyrimidin-4-yl)-[1,2,4]oxadiazol-3-yl]-6-methyl -phenoxy}-propane-1,2-diol;
3-{4-[5-(6-ethyl-2-ethylamino-pyrimidin-4-yl)-[1,2,4]oxadiazol-3-yl]-2,6-dimethyl -phenoxy}-propane-1,2-diol;
3-{4-[5-(6-ethyl-2-ethylamino-pyrimidin-4-yl)-[1,2,4]oxadiazol-3-yl]-2,6-dimethyl -phenoxy}-propane-1,2-diol;
3-{2-chloro-4-[5-(2-isopropylamino-6-methyl-pyrimidin-4-yl)-[1,2,4]oxadiazol-3-yl]-6-methyl -phenoxy}-propane-1,2-diol;
3-{4-[5-(2-isopropylamino-6-methyl-pyrimidin-4-yl)-[1,2,4]oxadiazol-3-yl]-2-methoxy-6-methyl -phenoxy}-propane-1,2-diol;
3-{2-chloro-4-[5-(2-isopropoxy-6-methyl-pyrimidin-4-yl)-[1,2,4]oxadiazol-3-yl]-6-methyl -phenoxy}-propane-1,2-diol;
N—((S)-3-{2-ethyl-4-[3-(2-isopropylamino-6-methyl-pyrimidin-4-yl)-[1,2,4]oxadiazol-5-yl]-6-methyl-phenoxy}-2-hydroxy-propyl)-2-hydroxy-acetamide;
3-(3-{4-[5-(2-diethylamino-6-methyl-pyrimidin-4-yl)-[1,2,4]oxadiazol-3-yl]-2-ethyl-6-methyl -phenoxy}-2-hydroxy-propylamino)-propionic acid; and
3-{2-ethyl-4-[5-(2-isopropylamino-6-methyl-pyrimidin-4-yl)-[1,2,4]oxadiazol-3-yl]-6-methyl -phenyl}-N-(2-hydroxy-ethyl)propionamide;
or a salt of such a compound.

13. A pharmaceutical composition comprising a compound according to claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 8,299,086 B2  
APPLICATION NO. : 12/738110  
DATED : October 30, 2012  
INVENTOR(S) : Martin Bolli et al.

Page 1 of 1

It is certified that error appears in the above-identified patent and that said Letters Patent is hereby corrected as shown below:

In the Claims:

In claim 6, column 80, line 61, please replace "$C_{1-4}$-alkyl" with "$C_{1-2}$-alkyl".

Signed and Sealed this
Thirtieth Day of April, 2013

Teresa Stanek Rea
*Acting Director of the United States Patent and Trademark Office*